(12) United States Patent
Qi

(10) Patent No.: US 12,403,184 B2
(45) Date of Patent: Sep. 2, 2025

(54) COMPOSITIONS AND METHODS FOR TREATING NEURODEGENERATIVE DISRODERS

(71) Applicant: CASE WESTERN RESERVE UNIVERSITY, Cleveland, OH (US)

(72) Inventor: Xin Qi, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1199 days.

(21) Appl. No.: 17/264,923

(22) PCT Filed: Jul. 31, 2019

(86) PCT No.: PCT/US2019/044465
§ 371 (c)(1),
(2) Date: Feb. 1, 2021

(87) PCT Pub. No.: WO2020/028549
PCT Pub. Date: Feb. 6, 2020

(65) Prior Publication Data
US 2021/0322524 A1 Oct. 21, 2021

Related U.S. Application Data

(60) Provisional application No. 62/712,776, filed on Jul. 31, 2018.

(51) Int. Cl.
A61K 38/46 (2006.01)
A61K 38/16 (2006.01)
A61P 25/28 (2006.01)

(52) U.S. Cl.
CPC ............ *A61K 38/46* (2013.01); *A61K 38/162* (2013.01); *A61P 25/28* (2018.01)

(58) Field of Classification Search
CPC .... A61K 38/46; A61K 38/162; A61K 38/005; A61K 38/10; A61P 25/28; A61P 25/14
See application file for complete search history.

(56) References Cited

U.S. PATENT DOCUMENTS 10,245,297 B2 4/2019 Mochly-Rosen et al.
2017/0312332 A1* 11/2017 Mochly-Rosen ....... A61P 25/28

OTHER PUBLICATIONS

Guo et al., Inhibition of mitochondrial fragmentation diminishes Huntington's disease-associated neurodegeneration, The Journal of Clinical Investigation , vol. 123, p. 5371-5388. (Year: 2013).*
Fang, Hsin-Yuan, et al., "Atpase Family Aaa Domain-Containing 3A is a Novel Anti-Apoptotic Factor in Lung Adenocarcinoma Cells", Journal of Cell Science, Apr. 1, 2010, vol. 123, pp. 1171-1180.
Gilquin, Benoit, et al. "The AAA+ ATPASE ATAD3A Controls Mitochondrial Dynamics at the Interface of the Inner and Outer Membranes", Molecular and cellular biology, Feb. 12, 2010, vol. 30, No. 8, pp. 1984-1996.
Harel, Tamar, et al., "Recurrent De Novo Biallelic Variation ATAD3A, Encoding a Mitochondrial Membrane Protein, Results in Distinct Neurological Syndromes", Am J Hum Genet, Sep. 15, 2016, vol. 99, No. 4, pp. 831-845.

* cited by examiner

*Primary Examiner* — Adam Weidner
*Assistant Examiner* — Tiffany M Gough
(74) *Attorney, Agent, or Firm* — Tarolli, Sundheim, Covell & Tummino LLP

(57) ABSTRACT

A method of inhibiting aberrant ATAD3A activation and/or oligomerization in mitochondria of a cell includes administering to the cell a therapeutic agent that inhibits binding or complexing of ATAD3A with Drp1 in the mitochondria of the cell.

16 Claims, 54 Drawing Sheets
Specification includes a Sequence Listing.

a b a b

C

|  |  | 71 DA1 80 |
|---|---|---|
| O00429 | DNM1L-Human | SQEDKRKTTG |
| O35303 | DNM1L-Rat | SPEDKRKTTG |
| Q8K1M6 | DNM1L-Mouse | SPEDKRKTTG |
| Q2KIA5 | DNM1L-Bovin | APEDKRKTTG |
| Q7SXN5 | DNM1L-Danre | DPEDRRKTSE |

|  |  | DA2 |
|---|---|---|
| Q9NVI7 | ATAD3-Human | QAEERRKTLS |
| Q3KRE0 | ATAD3-Rat | QAEERRKTLN |
| Q925I1 | ATAD3-Mouse | QAEERRKTLT |
| A7YWC4 | ATAD3-Bovin | QAEERRKTLS |
| Q58E76 | ATAD3-Xenla | QAEERRKTLN |

Fig. 9C

SEQUENCE LISTING

<160> NUMBER OF SEQ ID NOS: 18

<210> SEQ ID NO 1

```
<211> LENGTH: 10
<212> TYPE: PRT
<213> ORGANISM: Homo sapiens

<400> SEQUENCE: 1

Ser Gln Glu Asp Lys Arg Lys Thr Thr Gly
1               5                   10

<210> SEQ ID NO 2
<211> LENGTH: 6
<212> TYPE: PRT
<213> ORGANISM: Homo sapiens

<400> SEQUENCE: 2

Glu Asp Lys Arg Lys Thr
1               5

<210> SEQ ID NO 3
<211> LENGTH: 10
<212> TYPE: PRT
<213> ORGANISM: Homo sapiens

<400> SEQUENCE: 3

Gln Ala Glu Glu Arg Arg Lys Thr Leu Ser
1               5                   10

<210> SEQ ID NO 4
<211> LENGTH: 6
<212> TYPE: PRT
<213> ORGANISM: Homo sapiens

<400> SEQUENCE: 4

Glu Glu Arg Arg Lys Thr
1               5

<210> SEQ ID NO 5
<211> LENGTH: 10
<212> TYPE: PRT
<213> ORGANISM: Rattus norvegicus

<400> SEQUENCE: 5

Ser Pro Glu Asp Lys Arg Lys Thr Thr Gly
1               5                   10

<210> SEQ ID NO 6
<211> LENGTH: 10
<212> TYPE: PRT
<213> ORGANISM: Mus musculus

<400> SEQUENCE: 6

Ser Pro Glu Asp Lys Arg Lys Thr Thr Gly
1               5                   10

<210> SEQ ID NO 7
<211> LENGTH: 10
<212> TYPE: PRT
<213> ORGANISM: Bovine adenovirus type 1

<400> SEQUENCE: 7

Ala Pro Glu Asp Lys Arg Lys Thr Thr Gly
1               5                   10

<210> SEQ ID NO 8
<211> LENGTH: 10
<212> TYPE: PRT
```

```
<213> ORGANISM: Danio rerio

<400> SEQUENCE: 8

Asp Pro Glu Asp Arg Arg Lys Thr Ser Glu
1               5                   10

<210> SEQ ID NO 9
<211> LENGTH: 10
<212> TYPE: PRT
<213> ORGANISM: Rattus norvegicus

<400> SEQUENCE: 9

Gln Ala Glu Glu Arg Arg Lys Thr Leu Asn
1               5                   10

<210> SEQ ID NO 10
<211> LENGTH: 10
<212> TYPE: PRT
<213> ORGANISM: Mus musculus

<400> SEQUENCE: 10

Gln Ala Glu Glu Arg Arg Lys Thr Leu Thr
1               5                   10

<210> SEQ ID NO 11
<211> LENGTH: 10
<212> TYPE: PRT
<213> ORGANISM: Bovine adenovirus type 1

<400> SEQUENCE: 11

Gln Ala Glu Glu Arg Arg Lys Thr Leu Ser
1               5                   10

<210> SEQ ID NO 12
<211> LENGTH: 10
<212> TYPE: PRT
<213> ORGANISM: Xenopus laevis

<400> SEQUENCE: 12

Gln Ala Glu Glu Arg Arg Lys Thr Leu Asn
1               5                   10

<210> SEQ ID NO 13
<211> LENGTH: 19
<212> TYPE: RNA
<213> ORGANISM: Artificial Sequence
<220> FEATURE:
<223> OTHER INFORMATION: Synthetic Construct

<400> SEQUENCE: 13
uucuccgaac gugucacgu                                              19

<210> SEQ ID NO 14
<211> LENGTH: 19
<212> TYPE: RNA
<213> ORGANISM: Artificial Sequence
<220> FEATURE:
<223> OTHER INFORMATION: Synthetic Construct

<400> SEQUENCE: 14
agauggagcu gaggcauaa                                              19

<210> SEQ ID NO 15
<211> LENGTH: 11
<212> TYPE: PRT
```

```
<213> ORGANISM: Artificial Sequence
<220> FEATURE:
<223> OTHER INFORMATION: Synthetic Construct

<400> SEQUENCE: 15

Tyr Gly Arg Lys Lys Arg Arg Gln Arg Arg
1               5                   10

<210> SEQ ID NO 16
<211> LENGTH: 19
<212> TYPE: PRT
<213> ORGANISM: Artificial Sequence
<220> FEATURE:
<223> OTHER INFORMATION: Synthetic Construct

<400> SEQUENCE: 16

Tyr Gly Arg Lys Lys Arg Arg Gln Arg Arg Gly Gly Glu Asp Lys
1               5                   10                  15

Arg Lys Thr

<210> SEQ ID NO 17
<211> LENGTH: 19
<212> TYPE: PRT
<213> ORGANISM: Artificial Sequence
<220> FEATURE:
<223> OTHER INFORMATION: Synthetic Construct

<400> SEQUENCE: 17

Tyr Gly Arg Lys Lys Arg Arg Gln Arg Arg Gly Gly Glu Glu Arg
1               5                   10                  15

Arg Lys Thr

<210> SEQ ID NO 18
<211> LENGTH: 9
<212> TYPE: PRT
<213> ORGANISM: Mus musculus

<400> SEQUENCE: 18

Ala Gln Tyr Gln Asp Lys Leu Ala Arg
1               5
```

COMPOSITIONS AND METHODS FOR TREATING NEURODEGENERATIVE DISRODERS

RELATED APPLICATION

This application claims priority from U.S. Provisional Application No. 62/712,776 filed Jul. 31, 2018, the subject matter of which is incorporated herein by reference in its entirety.

GOVERNMENT FUNDING

This invention was made with government support under Grant Nos. R01 NS088192, R01 GM121583, 1S10OD023436-01, awarded by The National Institutes of Health. The United States government has certain rights to the invention.

BACKGROUND

Defects in mitochondrial fusion/fission and mitochondrial bioenergetics have been implicated in the pathogenesis of many neurodegenerative diseases, such as Alzheimer's, Parkinson's, and Huntington's diseases. Dynamin-related protein 1 (Drp1), a cytosolic GTPase, mediates mitochondrial fission. Upon activation, Drp1 is recruited from the cytosol to the surface of mitochondria, where it assembles by self-oligomerization to initiate mitochondrial division. Mitochondrial nucleoids, which contain mitochondrial DNA (mtDNA)-protein complex, facilitate mtDNA maintenance, and gene expression and are essential for mitochondrial biogenesis and cellular energy homeostasis.

Recent studies suggest that the distribution and organization of mitochondrial nucleoids are associated with mitochondrial division. Mitochondrial nucleoids are found adjacent to Drp1 at the tips of newly divided mitochondria. Knockout of Drp1 causes severe mtDNA nucleoid clustering, which leads to mitochondrial respiration deficiency in both cultured cells and mouse hearts. Despite these observations, the factors that couple mitochondrial dynamics with mtDNA maintenance and bioenergetics remain poorly understood. In particular, it is unclear how dysregulation in the signaling pathways involved in mitochondrial fission impacts mtDNA integrity in the context of neurodegeneration.

Huntington's disease (HD) is a fatal inherited neurodegenerative disease caused by an expansion of a polyglutamine repeat within the protein huntingtin (Htt). Drp1 hyperactivation and mitochondrial fission impairment occur in various HD models. It was previously observed that inhibition of Drp1 hyperactivation is sufficient to reduce HD-associated neuropathology, underscoring the importance of Drp1-mediated mitochondrial damage in HD pathogenesis.

SUMMARY

Embodiments described herein relate to methods of inhibiting ATPase family AAA-domain containing protein 3A (ATAD3A) oligomerization, ATAD3A activation, and/or Drp1 activation in cells (e.g., nerve cells) of subjects with neurodegenerative disorders in associated with aberrant ATAD3A activation, and particularly relates to methods of treating a disorders and/or neurodegenerative disorders associated with aberrant ATAD3A activation in a subject.

The methods can include administering to nerve cells of a subject in need thereof a therapeutic agent that inhibits binding, complexing, and/or interaction of Drp1 with ATAD3A and/or ATAD3A oligomerization. Inhibiting Drp1/ATAD3A binding, complexing, and/or interaction inhibits ATAD3A oligomerization, suppresses mitochondrial fragmentation and mtDNA lesion, and reduces cell death in subjects with disorders associated with aberrant ATAD3A activation. In some embodiments, the disorder can include a neurodegenerative disorder, such as a neurodegenerative disease associated with mitochondrial fission impairments and bioenergetics defects. In other embodiments, a neurodegenerative disease associated with mitochondrial fission impairments and bioenergetics defects is Huntington's disease (HD).

In other embodiments, the therapeutic agent can include a therapeutic peptide. The therapeutic peptide can have an amino acid sequence at least about 80% sequence identical to about 6 to about 12 consecutive amino acids of an interaction site of Drp1 with ATAD3A. In some embodiments, the therapeutic peptide can have an amino acid sequence that is at least about 80% identical to at least 6 consecutive amino acids of SEQ ID NO: 1, such as SEQ ID Nos: 1, 2, 5, 6, 7, and 8. For example, the therapeutic peptide can have an amino acid sequence of SEQ ID NO: 2.

In other embodiments, the therapeutic agent can include a transport moiety that is linked to the therapeutic peptide and facilitates uptake of the therapeutic peptide by the nerve cell. The transport moiety can be, for example, an HIV Tat transport moiety.

In other embodiments, the therapeutic agent can be administered systemically to the subject being treated. For example, a therapeutic agent that includes a therapeutic peptide having an amino acid sequence of SEQ ID NO: 2, which is linked to a HIV Tat transport moiety, can be administered intravenously to a subject with Huntington's disease (HD).

The amount of the therapeutic agent that is administered to the subject can be an amount effective to inhibit ATAD3A oligomerization, inhibit ATAD3A activation, inhibit Drp1 activation, suppress mitochondrial fragmentation and mtDNA lesion, and/or reduce bioenergetic deficits and nerve cell death in the subject. In some embodiments, the amount of the therapeutic agent administered to a subject can be an amount to reduce or treat HD associated behavioral deficits and neuropathology in the subject.

Figure 1A:
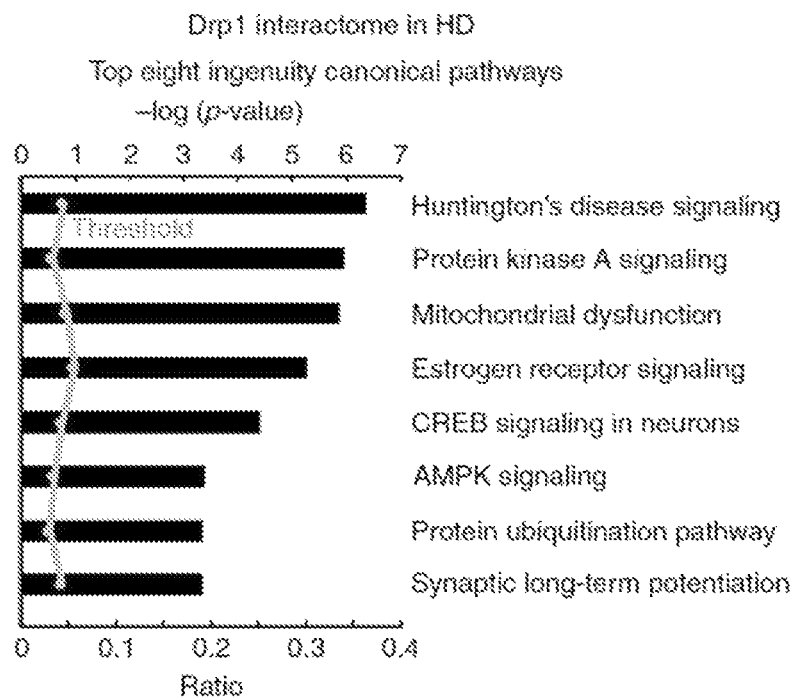
FIGS. 1(A-H) illustrate plots, graphs, and immunoblots showing ATAD3A binds to Drp1 in HD. (A) Affinity purification followed by tandem mass spectrometry analysis was conducted to identify Drp1-interacting proteins in striatal neuronal cells derived from HD patient-iPS or normal subject-iPS cells. The molecular and cellular functions of the Drp1 interactors in HD patient-derived neuronal cells are shown. (B) Upper: cellular location of the Drp1 interactors in HD neuronal cells. In particular, 32% of proteins are located on the mitochondria. ATAD3A ranked as a top candidate. Lower: Among mitochondrial candidates, mitochondrial nucleoid organization and energy production are enriched, and each account for up to 25% of all mitochondrial candidates Immunoprecipitation (IP) of total protein lysates was performed in HdhQ7 and HdhQ111 cells (C), in wildtype striatal cells exposed to 3-NP (5 mM for 4 h) (D), in striatal extracts of YAC128 mice (6 months old) or R6/2 mice (12 weeks old) or age-matched wildtype mice (E), and in fibroblasts of HD patient (HD1, GM4208, 35 years old, Male) or normal subject (Con1, Huf1) (F). Data are mean±SEM. Student t test. n=3. (G) Total protein lysates of frozen postmortem caudate nucleus of normal subjects and HD patients with different disease severity (grade 1 to grade 4, slight to severe) were subject to IP analysis. Nor: normal subject 5214; G1: HD 4283, grade 1; G2: HD 4557, grade 2; G3: HD 3573, grade 3; G4: HD 2903, grade 4. Patient information shown in FIG. 9F. The data below the blots indicate the relative density of Drp1 in ATAD3A immunoprecipitates (Drp1/ATAD3A in IP analysis). (H) GST-Drp1 (2 µg) and ATAD3A-Flag (2 µg) purified proteins were incubated in vitro for 30 mins. Left: IP with anti-Flag antibodies followed by western blot with the indicated antibodies. Right: GST pull down analysis. All shown representative blots are from at least 3 independent experiments.

The number of nucleoids immunopositive for both anti-DNA and anti-Tom20 was quantitated by NIH Image J software. Three independent experiments, one-way ANOVA with Tukey's post-hoc test. All shown blots are from at least 3 independent experiments. Data are mean±SEM FIGS. 5(A-J) illustrate immunoblots, images, and graphs showing DA1 peptide blocks Drp1/ATAD3A binding. (A) Sequence of homology between Drp1 (human, NP_036192) (SEQ ID NO: 2) and ATAD3A (human, NP_001164006) (SEQ ID NO: 4). Columns (:) indicate identical amino acids; single dot (•) indicate high similarity between amino acids. (B) Stick drawings of ATAD3A and Drp1 main domains. Highlighted are the two regions of homology between the two proteins, region DA1 in Drp1 and the corresponding region DA2 in ATAD3A. (C) Mapping DA1 on crystal structure of Drp1 GTPase-GED fusion construct and DA2 on the N-terminus (residues 1-210) of ATAD3A simulated structure. (D) Upper: HdhQ7 and HdhQ111 cells were treated with TAT or peptide DA1 (1 µM/day for 4 days). Lower: R6/2 or wildtype mice were treated with TAT or DA1 (1 mg/kg/day) from 6 to 12 weeks. The total lysates of cells or mouse striatum were subject to IP analysis. Three independent experiments. (E) DA1 or TAT was incubated with recombinant proteins in vitro for 30 mins. GST pull down followed by WB analysis was carried out. 3 independent experiments. (F) Biotin-conjugated DA1 or TAT (10 µM, each) was incubated with total lysates of HdhQ7 and HdhQ111 cells Immunoprecipitates were analyzed by WB. 3 independent experiments. (G) HEK293 cells were transfected with ATAD3A-Flag wildtype (WT) or ΔN50 mutant plasmids followed by TAT or DA1 treatment (1 µM, each) for 48 h. ATAD3A oligomerization was analyzed by WB. Three independent experiments. (H) Left: HD cells were treated with TAT or DA1 (1 µM/day for 4 days), 4 independent experiments. YAC128 or wildtype mice from 6 months of age (Middle, 6-7 mice/group), and R6/2 or wildtype mice from 12 weeks of age (Right, 4 mice/group) received either TAT or DA1 (1 mg/kg/day). Drp1 mitochondrial levels were determined by WB. (I) Drp1 oligomerization was analyzed using total striatal lysates of mice (Upper: YAC128-12 months old; Lower: R6/2 mice-12 weeks old). n=6 mice/group. (J) Drp1 oligomerization was analyzed by WB at the indicated groups. Three independent experiments. All data are mean±SME. One-way ANOVA with Tukey's post-hoc test FIGS. 6(A-H) illustrate images, immunoblots, and graphs showing DA1 treatment reduces mitochondrial damage and cell death in HD cell cultures. HdhQ7 and HdhQ111 striatal cells were treated with control TAT or peptide DA1 (1 µM/day for 4 days). (A) Mitochondrial morphology was determined by staining cells with anti-Tom20 antibody. Scale bar: 10 µm. The percentage of cells with fragmented mitochondria relative to the total number of cells was quantitated. Three independent studies, one-way ANOVA with Tukey's post-hoc test. (B) TFAM and PGC1α protein levels were analyzed by WB. Histogram: the relative density of TFAM and PGC1α to Actin. Three independent studies, one-way ANOVA with Tukey's post-hoc test. (C) HdhQ7 and HdhQ111 cells were transfected with control siRNA (siCon) or ATAD3A siRNA (siAD) followed by treatment with TAT or DA1 (1 µM/day for 4 days). TFAM and ATAD3A protein levels were analyzed by WB. Histogram: the relative density of TFAM to Actin. Four independent studies, one-way ANOVA with Tukey's post-hoc test. (D) mtDNA-encoded or nuclear-encoded mitochondrial electron transport proteins were analyzed by WB with the indicated antibodies. Actin: a loading control. VDAC: a mitochondrial loading control. Histogram: the quantitation of relative mtCO$_2$ protein level to Actin. Three independent studies, one-way ANOVA with Tukey's post-hoc test. (E) TFAM and mtDNA LSP interaction was analyzed by biotin-streptavidin pull down. Histogram: the relative density of TFAM in the Biotin-LSP precipitates. Three independent experiments, one-way ANOVA with Tukey's post-hoc test. (F) mtDNA lesion was measured by qPCR. Five independent studies, one-way ANOVA with Tukey's post-hoc test. (G) mitoROS was evaluated by mitoSOX fluorescent probe. At least 100 cells per group were analyzed. At least 3 independent studies, one-way ANOVA with Tukey's post-hoc test. (H) Mitochondrial respiratory activity was determined by a seahorse analyzer. Three independent studies, one-way ANOVA with Tukey's post-hoc test. All data are mean±SEM.

FIGS. 7(A-L) images, graphs, and immunoblots showing DA1 treatment reduces HD-associated neuropathology. (A) Neurons were stained with anti-GAD67 antibodies to indicate striatal neurons and anti-Tom20 antibodies to label mitochondria. Mitochondrial length along the neurite of GAD67-immunopositive neurons was quantitated. At least 50 neurons/group were analyzed. (B) Neurons were stained with anti-MAP2/anti-GAD67 (left) or anti-Tau/anti-DARPP32 (right) to indicate dendritic and axonal morphology, respectively. MAP2+ dendrite and Tau+ axon length in neurons were quantitated. At least 50 neurons/group were analyzed. Scale bar: 10 µm. (C) mitoROS was determined by mitoSOX probe. (D) Cell death induced by BDNF withdrawal for 24 h was determined by the release of LDH. Three independent experiments. HD R6/2 and wildtype mice were treated with either TAT or DA1 from 6 weeks. (E) Body weight was recorded. **$p<0.001$, *$p<0.05$ vs. HD mice treated with TAT. Student t-test. TAT: 21 mice; DA1: 15 mice. (F) Survival of R6/2 mice from the age of 6 to 21 weeks was analyzed by Log-rank (Mantel-Cox) test. (G) locomotion activity of R6/2 mice (12 weeks old) was determined (WT/TAT: 16 mice; WT/DA1: 10 mice; R6/2/TAT: 13 mice; R6/2/DA1: 9 mice). Shown is horizontal activity. (H) YAC128 and wildtype mice were treated with TAT or DA1 from the age of 3 to 12 months (see FIG. 16A). Locomotion activity was monitored (n=12-20 mice/group). Shown is vertical activity. Two-way ANOVA with Tukey's post-hoc test. #$p<0.05$ vs. HD mice treated with TAT; *$p<0.05$ vs. wildtype mice treated with TAT. (I) DARPP-32 immunodensity was assessed in the dorsolateral striatum of TAT-treated or DA1-treated R6/2 mice (12 weeks old). Scale bar: 100 µm. n=6 mice/group. (J) Golgi-Cox staining of mouse brain was shown. The total dendritic length/neuron was quantitated. 20 neurons/group was analyzed. Scale bar: 10 µm. (K) Striatum volume was assessed. n=5-7 mice/group. 1 DARPP-32 and PSD95 protein levels in YAC128 mouse (12 months old) striatal extracts were analyzed by WB. n=7 mice/group. All data are mean±SEM. One-way ANOVA with Tukey's post-hoc test in A-D, G, I-L.

FIGS. 8(A-E) illustrate immunoblots, graphs, and images showing DA1 treatment reduces mtDNA damage in HD mice. Mitochondria were isolated from striatum of R6/2 or age-matched wildtype mice (12 weeks old) (A), and YAC128 or age-matched wildtype mice (6 months old) (B). Protein levels of mtCO2 and TFAM were determined by WB. VDAC: a mitochondrial loading control. Histogram: the relative density of mtCO2 and TFAM to VDAC. n=3-6 mice/group. One-way ANOVA with Tukey's posthoc test. (C) Plasma samples were harvested from YAC128 mice or wildtype mice (6 months old). The mtDNA content in plasma was examined by qPCR. One-way ANOVA with Tukey's post-hoc test. n=6 mice/group. (D) Brain coronal sections (10 μm) of R6/2 (left, 12 weeks old) or YAC128 (right, 6 months old) mice were stained with anti-Iba1 antibody to determine microglial activity. Boxed images were enlarged on the bottom. Scale bar: 10 μm. Histogram: the quantitation of Iba1 immunodensity/mm$_2$ n=3 mice/group. ANOVA with Tukey's post-hoc test. All data are mean±SEM. (E) A summary scheme.

FIGS. 9(A-K) illustrate immunoblots, plots, and images showing the effects of DA1 on mitochondrial dynamics. (A) cells were treated with TAT or DA1 or DA2 (1 μM/day for 4 days, each). IP analysis was performed. Histogram: quantitation of ATAD3A level in Drp1 immunoprecipitates. 4 independent experiments, two-way ANOVA with Tukey's post-hoc test. (B) Wildtype mouse striatal cells were treated with TAT or DA1 (1 μM) overnight followed by exposure to 3-NP (5 mM for 4 hours). IP analysis was performed. Histogram: the quantitation of ATAD3A levels in Drp1-immuniprecipates. 3 independent experiments. (C) Sequence alignment of DA1 and DA2 through species (SEQ ID NO: 1 (DA1-Human), SEQ ID NO: 5 (DA1-Rat), SEQ ID NO: 6 (DA1-Mouse), SEQ ID NO: 7 (DA1-Bovin), SEQ ID NO: 8 (DA1-Danre), (SEQ ID NO: 3 (ATAD3-Human), SEQ ID NO: 9 (ATAD3-Rat), SEQ ID NO: 10 (ATAD3-Mouse), SEQ ID NO: 11 (ATAD3-Bovin), and SEQ ID NO: 12 (ATAD3-Xenia). (D) cells were treated with DA1 or TAT (1 μM/day for 4 days), followed by incubation with cross-linker 1 mM DSP (left, right) or 1% FA (middle). IP analysis was performed. Blots are representative of 3 independent experiments. (E) Biotin-conjugated DA1 or TAT (10 μM, each) was incubated with either ATAD3A-Flag or GST-Drp1 proteins Immunoprecipitates were analyzed by WB with the indicated antibodies. Shown blots are representative of 3 independent experiments. (F) Left: Time course of Drp1 GTP hydrolysis plotted as a function of inorganic phosphate (Pi) released over time. Right: The turnover number (kcat) of initial Drp1 GTP hydrolysis in the absence and presence of DA1 is plotted. 3 independent experiment. (G) Neuo2A cells were treated with TAT or DA1 (1 μM) overnight following exposure of 3-NP (5 mM) for 7 hours. ATAD3A dimerization was determined. Histogram: the relative density of ATAD3A dimer versus the total level of ATAD3A in the presence of β-ME. 4 independent experiments. (H) HEK293 cells were expressed ATAD3A WT or K135E mutant. ATAD3A dimerization was determined. Histogram: the relative density of ATAD3A dimer versus the total level of ATAD3A in the presence of β-ME. 4 independent experiments. (I) The total protein levels of mitochondrial dynamics proteins were determined by WB. Shown blots are representative of 2 independent experiments. (J) Representative DNA agarose gel of amplification of the 10 kb mtDNA fragment for FIG. 6F. (K) The images show a cluster of neurons for FIG. 7A. Scale bar: 10 μm. Data are mean±SEM. One-way ANOVA with Tukey's post-hoc test for B, G, H.

FIGS. 10(A-I) illustrate plots, images, graphs, and immunoblots showing the effects of DA1 treatment in R6/2 and YAC128 HD mice. (A) Timeline and administration avenue of DA1 treatment in HD R6/2 (upper) and YAC128 (lower) mice. (B) FITC-conjugated DA1 or TAT (1 mg/kg, each) was i.p. injected in wildtype mice for 1 day. Mouse brains were harvested and sectioned (10 μm). FITC-conjugated DA1 was visualized by microscope. Scale bar: 10 μm. (C) Wildtype mice were treated with DA1 (1 mg/kg/day) or saline for 30 days using Alzet mini pumps. Thirty days of DA1 treatment had no effects on spleen morphology and relative weight (spleen/body weight). n=5 mice/group. (D) Body weight of wildtype mice treated with TAT or DA1 (1 mg/kg/day) was recorded from the age of 6 to 12 weeks. n=10 mice/group. (E) One hour of overall movement activity in R6/2 and wildtype mice was determined by locomotion activity chamber at the age of 12 weeks (WT/TAT: 16 mice; WT/DA1: 10 mice; R6/2/TAT: 13 mice; R6/2/DA1: 9 mice). Shown is total traveled distance of mice. One-way ANOVA with Tukey's post-hoc test. (F) Hindlimb clasping was assessed with the tail suspension test once a week from the ages of 8 to 12 weeks (n=10-15 mice/group). Multiple t test. (G) YAC128 and wildtype mice were treated with the TAT or DA1 (1 mg/kg/day) from the age of 3 to 12 months. A locomotion activity chamber was used to monitor 24 hours of general motility of YAC128 and wildtype mice at the indicated age (n=12-20 mice/group). Shown are horizontal activity, total traveled distance and movement number of mice. #, p<0.05 vs. HDmice treated with TAT; *, p<0.05 vs. wildtypemice treated with TAT, two-way ANOVA with Tukey's post-hoc test. (H) nuclear-encoded mitochondrial respiratory related proteins were analyzed with striatal mitochondrial lysates of YAC128 and wildtype mice (6 months old) by WB with the indicate antibodies. Shown blots were from three independent experiments. (I) TFAM and PGC1α in total striatal lysates of YAC128 mice (12 months old) were analyzed by WB. Actin was used as a loading control. n=6 mice/group, one-way ANOVA with Tukey's post-hoc test. Data are mean±SEM.

DETAILED DESCRIPTION

Embodiments described herein are not limited to the particular methodology, protocols, and reagents, etc., and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, "one or more of a, b, and c" means a, b, c, ab, ac, bc, or abc. The use of "or" herein is the inclusive or.

The term "administering" to a patient includes dispensing, delivering or applying an active compound in a pharmaceutical formulation to a subject by any suitable route for delivery of the active compound to the desired location in the subject (e.g., to thereby contact a desired cell, such as a desired neuron), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to stimulate axonal growth in a fetus. Specific routes of administration may include topical application (such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

The term "antibody", includes human and animal mAbs, and preparations of polyclonal antibodies, synthetic antibodies, including recombinant antibodies (antisera), chimeric antibodies, including humanized antibodies, anti-idiotopic antibodies and derivatives thereof. A portion or fragment of an antibody refers to a region of an antibody that retains at least part of its ability (binding specificity and affinity) to bind to a specified epitope. The term "epitope" or "antigenic determinant" refers to a site on an antigen to which antibody paratope binds. Epitopes formed from contiguous amino acids are typically retained on exposure to denaturing solvents whereas epitopes formed by tertiary folding are typically lost on treatment with denaturing solvents. An epitope typically includes at least 3, at least 5, or 8 to 10, or about 13 to 15 amino acids in a unique spatial conformation. Methods of determining spatial conformation of epitopes include, for example, x-ray crystallography and 2-dimensional nuclear magnetic resonance.

The terms "chimeric protein" or "fusion protein" refer to a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "contacting nerves", "contacting neurons", "treating nerves", or "treating neurons" refers to any mode of agent delivery or "administration," either to cells or to whole organisms, in which the agent is capable of exhibiting its pharmacological effect in neurons. "Contacting neurons" includes both in vivo and in vitro methods of bringing an agent of the invention into proximity with a neuron. Suitable modes of administration can be determined by those skilled in the art and such modes of administration may vary between agents.

An "effective amount" of an agent or therapeutic peptide is an amount sufficient to achieve a desired therapeutic or pharmacological effect, such as an amount that is capable of activating the growth of neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

The term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced.

The term "gene" or "recombinant gene" refers to a nucleic acid comprising an open reading frame encoding a polypeptide, including both exon and (optionally) intron sequences.

The term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into a target tissue, such that it enters the animal's system and, thus, is subject to metabolism and other like processes, for example, subcutaneous administration.

The term "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

The terms "polynucleotide sequence" and "nucleotide sequence" are also used interchangeably herein.

The terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, NY, 1989)). A "peptide" can comprise any suitable L- and/or D-amino acid, for example, common a-amino acids (e.g., alanine, glycine, valine), non-a-amino acids (e.g., P-alanine, 4-aminobutyric acid, 6aminocaproic acid, sarcosine, statine), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & Wuts, PROTECTING GROUPS IN ORGANIC SYNTHESIS (John Wiley & Sons, 1991). The functional groups of a peptide can also be derivatized (e.g., alkylated) using art-known methods.

The term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. These modifications involve changes to the peptide that do not occur naturally (such as altered backbones and the incorporation of nonnatural amino acids).

The terms "prevent" or "preventing" refer to reducing the frequency or severity of a disease or condition. The term does not require an absolute preclusion of the disease or condition. Rather, this term includes decreasing the chance for disease occurrence.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "recombinant," as used herein, means that a protein is derived from a prokaryotic or eukaryotic expression system.

The term "therapeutically effective" means that the amount of the composition used is of sufficient quantity to ameliorate one or more causes, symptoms, or sequelae of a disease or disorder. Such amelioration only requires a reduction or alteration, not necessarily elimination, of the causes, symptoms, or sequelae of a disease or disorder.

The term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

The terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

The term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

The terms "portion", "fragment", "variant", "derivative" and "analog", when referring to a polypeptide include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

Embodiments described herein relate to methods of inhibiting ATAD3A oligomerization, ATAD3A activation, and/or Drp1 activation in cells (e.g., nerve cells) of subjects with neurodegenerative disorders associated with aberrant ATAD3A activation and particularly relates to methods of treating disorders and/or neurodegenerative disorders associated with aberrant ATAD3A activation in a subject.

ATAD3A is a nuclear-encoded mitochondrial protein that spans the inner and outer membranes with its two terminal domains located in the outer membrane and the matrix. ATAD3A regulates mitochondrial morphology and controls cholesterol trafficking at mitochondrial contact sites. Either overexpression or downregulation of ATAD3A results in mitochondrial fragmentation, suggesting a scaffold-like property on maintenance of mitochondrial morphology. Moreover, ATAD3A is a component of mitochondrial nucleoid complex, which implicates in mtDNA nucleoid maintenance. While global knockout of ATAD3A is embryonic lethal, selective loss of ATAD3A in mouse skeletal muscle disrupts mitochondrial ultrastructure and reduces the number of cristae junctions, which impairs mtDNA integrity. The expression of mutant ATAD3A in *Drosophila* causes severe mitochondrial fragmentation, aberrant cristae, and increased mitophagy in both motor neurons and muscle, leading to early lethality. Patients carrying an ATAD3A mutant show neurodegenerative conditions associated with axonal neuropathy, and spastic paraplegia. The proper function of ATAD3A is therefore critical for cell survival.

It was found that under stressed conditions in neurodegenerative diseases, such as in Huntington's disease (HD), ATAD3A, forms oligomers due to K135 deacetylation via its coiled-coil domain, and recruits fission protein Drp1 to the mitochondria where ATAD3A and Drp1 form a complex. This leads to mitochondrial fragmentation. ATAD3A oligomerization impairs mtDNA maintenance by disrupting the binding between TFAM and mtDNA, resulting in the loss of mtDNA and subsequent mitochondrial bioenergetics defects. As a result, ATAD3A oligomerization simultaneously causes mitochondrial fragmentation and mitochondrial bioenergetics defects, which lead to mitochondrial dysfunction and neuronal cell death.

Blocking Drp1/ATAD3A interaction in nerve cells of subject with neurodegenerative disorders associated with aberrant ATAD3A activation was found to inhibit ATAD3A oligomerization or dimerization, ATAD3A activation, and Drp1 activation, which in turn inhibited excessive mitochondrial fragmentation and loss of mtDNA, reduced bioenergetic deficits and nerve cell death, and reduced or treated behavioral and neuropathological phenotypes of the subject. Thus, the formation of aberrant complexes of ATAD3A/Drp1 on the mitochondria is a key step in initiating mitochondrial injury, which in turn results in neuronal pathology in neurodegenerative disorders, such as Huntington's disease (HD). Inhibitors that selectively block ATAD3A oligomerization and, hence, ATAD3A activation and Drp1 activation, by inhibiting ATAD3A/Drp1 interaction or binding can inhibit mitochondrial fragmentation and can provide a therapeutic route for HD and other neurodegenerative disorders or diseases in which ATAD3A oligomerization, ATAD3A activation and/or Drp1 activation results in mitochondrial damage, mitochondrial fragmentation, bioenergetic defects, and neuropathology.

Accordingly, in some embodiments therapeutic agents that inhibit ATAD3A/Drp1 interaction or binding in the mitochondria can be use in methods of treating ATAD3A and/or Drp1 mediated neurodegeneration and/or neurodegenerative diseases in a subject in need thereof. The ATAD3A and/or Drp1 mediated neurodegeneration and/or neurodegenerative diseases can include, for example, Huntington's disease (HD), spinocerebellar ataxias of types 1, 2, 3, 6, 7 and 17, dentatorubral pallidoluysian atrophy as well as spinobulbar muscular atrophy (Kennedy syndrome).

Other neurodegenerative diseases associated with aberrant ATAD3A activation that can also be treated by therapeutic agents, which inhibit ATAD3A/Drp1 interaction or binding and/or ATAD3A oligomerization in the mitochondria, can include Parkinson's disease, Multiple Sclerosis (MS), Amyotrophic Lateral Sclerosis (ALS), multi-system atrophy, Alzheimer's disease, stroke, progressive supranuclear palsy, progressive supernuclear palsy, granulovacuolar disease, frontotemporal dementia, corticobasal degeneration, epilepsy, autoimmune encephalomyelitis, diabetic neuropathy, glaucomatous neuropathy, Pick's disease, Lewy Body disease, Creutzfeld-Jacob Disease (CJD), variant Creutzfeld-Jacob Disease, new variant Creutzfeld-Jacob Disease, or kuru disease.

In some embodiments, a therapeutic agent that inhibits or reduces ATAD3A/Drp1 interaction or binding in the mitochondria, can include a therapeutic peptide or small molecule that binds to and/or complexes with ATAD3A and/or Drp1 to inhibit the interaction, binding, or complexing of ATAD3A with Drp1 and/or the oligomerization of ATAD3A. Therapeutic peptides or small molecules that bind to and/or complex with ATAD3A and/or Drp1 to inhibit or reduce binding or complexing of ATAD3A with Drp1 as well as inhibit ATAD3A oligomerization or dimerization or suppress ATAD3A and/or Drp1 mediated mitochondrial fragmentation and mtDNA lesion in the mitochondria can be used to treat neurodegerative diseases or disorders, such as HD, in a subject in need thereof.

In some embodiments, the therapeutic agent can comprise a short peptide derived from interaction sites between ATAD3A and Drp1 that inhibits or reduces binding or complexing of ATAD3A with Drp1 and/or oligomerization of ATAD3A. For example, the therapeutic agent can comprise short peptides of ATAD3A or Drp1 that can inhibit the interaction of ATAD3A with Drp1. The interaction site between Drp1 and ATAD3A was found to be the loop region of Drp1 GTPase domain and first coiled-coil (CC) domain of ATAD3A.

In some embodiments, the therapeutic agent can comprise a short peptide that is derived from the loop region of Drp1 GTPase and represents a sequence homologous to ATAD3A. In some embodiments, the therapeutic peptide can have an amino acid sequence at least about 80% identical to about 6 to about 12 consecutive amino acids of an interaction site of Drp1 with ATAD3A. For example, the therapeutic peptide can have an amino acid sequence that is at least about 80% identical to at least 6 consecutive amino acids of SEQ ID NO: 1. A therapeutic peptide having an amino acid sequence that is at least about 80% identical to at least 6 consecutive amino acids of SEQ ID NO: 1 can include therapeutic peptides having the amino acid sequence of SEQ ID Nos: 1, 2, 5, 6, 7, or 8. In other embodiments, the therapeutic peptide can have an amino acid sequence at least 80% identical to SEQ ID NO: 2.

In other embodiments, the therapeutic agent can comprise a short peptide that is derived from the CC domain of ATAD3 and represents a sequence homologous to Drp1. In some embodiments, the therapeutic peptide can have an amino acid sequence at least about 80% sequence identical to about 6 to about 12 consecutive amino acids of an interaction site of ATAD3A with Drp1. For example, the therapeutic peptide can have an amino acid sequence that is at least about 80% identical to at least 6 consecutive amino acids of SEQ ID NO: 3. A therapeutic peptide having an amino acid sequence that is at least about 80% identical to at least 6 consecutive amino acids of SEQ ID NO: 3 can include therapeutic peptides having the amino acid sequence of SEQ ID Nos: 3, 4, 9, 10, 11, or 12. In other embodiments, the therapeutic peptide can have an amino acid sequence at least 80% identical to SEQ ID NO: 4.

In some embodiments, the therapeutic agent or therapeutic peptide can include, a peptide that consists essentially, and/or consists of about 6 to about 12 amino acids and has an amino acid sequence that is at least about at least about 80%, at least about 85%, at least about 90%, at least about 95%, or about 100% identical to an about 6 to about 12 consecutive amino acids (e.g., about 6 to about 10 consecutive amino acids) of an interaction site of Drp1 and ATAD3A, such as a peptide having the amino acid sequence of SEQ ID NO: 2 or SEQ ID NO: 4.

The therapeutic peptides described herein can be subject to other various changes, substitutions, insertions, and deletions where such changes provide for certain advantages in its use. In this regard, therapeutic peptides that bind to and/or complex with an interaction site of Drp1 and ATAD3A can correspond to or be substantially homologous with, rather than be identical to, the sequence of a recited polypeptide where one or more changes are made and it retains the ability to inhibit or reduce interaction of Drp1 with ATAD3A and/or to inhibit aberrant ATAD3A oligomerization and/or mitochondrial fragmentation in the mitochondrial of a cell, such as a neuron.

The therapeutic peptide can be in any of a variety of forms of polypeptide derivatives that include amides, conjugates with proteins, cyclized polypeptides, polymerized polypeptides, analogs, fragments, chemically modified polypeptides and the like derivatives.

It will be appreciated that the conservative substitution can also include the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

One or more of peptides of the therapeutic peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to flavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the interaction of Drp1 and ATAD3A (without being restricted to the present examples).

The therapeutic peptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the polypeptides may be done by affinity methods, ion exchange chromatography, size exclusion chromatography, hydrophobicity or other purification technique typically used for protein purification. The purification step can be performed under non-denaturating conditions. On the other hand, if a denaturating step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, a therapeutic agent comprising the therapeutic peptides described herein can be provided in the form of a conjugate protein or drug delivery construct includes at least a transport subdomain(s) or moiety(ies) (i.e., transport moieties or cell penetrating moieties) that is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic polypeptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In one embodiment, the transport moiety can include at least one transport peptide sequence that allows the therapeutic polypeptide once linked to the transport moiety to penetrate into the cell by a receptor-independent mechanism. In one example, the transport peptide is a synthetic peptide that contains a Tat-mediated protein delivery sequence, such as $TAT_{47-57}$ (YGRKKRRQRRR (SEQ ID NO: 15). The $TAT_{47-57}$ transport moiety can be linked to a therapeutic peptide, such as a peptide having SEQ ID NO: 2, via glycine linker (e.g., GG) to form a therapeutic agent having the amino acid sequence of YGRKKRRQRRR-GG-EDKRKT (SEQ ID NO: 16).

Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec.* 19:1173-1176, all herein incorporated by reference in their entirety).

In other embodiments, the therapeutic peptides can be expressed in cells being treated using gene therapy to inhibit Drp1 interaction or binding with ATAD3A. The gene therapy can use a vector including a nucleotide encoding the therapeutic peptides. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) *J Neurosci.* 22:10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

To combine advantageous properties of two viral vector systems, hybrid viral vectors may be used to deliver a nucleic acid encoding a therapeutic peptide to a target neuron, cell, or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression.

Other nucleotide sequence elements, which facilitate expression of the therapeutic peptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic peptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application. Neuron specific promoters, such as the platelet-derived growth factor β-chain (PDGF-β) promoter and vectors, are well known in the art.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the application. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun 13:141-164, 1994.

Additionally, the nucleic acid encoding the therapeutic peptides can be introduced into the target cell by transfecting the target cells using electroporation techniques. Electroporation techniques are well known and can be used to facilitate transfection of cells using plasmid DNA.

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

Where the target cell includes a nerve cell being treated, the vector can be delivered at an amount sufficient for the therapeutic peptide to be expressed to a degree, which allows for highly effective therapy. The therapeutic peptide can be expressed for any suitable length of time within the target cell, including transient expression and stable, long-term expression. In one aspect of the application, the nucleic acid encoding the therapeutic peptide will be expressed in therapeutic amounts for a defined length of time effective to inhibit neurodegeneration in the subject being treated. In another aspect, the nucleic acid encoding the therapeutic peptide will be expressed in therapeutic amounts for a defined length of time effective to increase survival rate of neurons.

The therapeutic agents described herein may be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In the methods of treatment disclosed herein, a therapeutically effective amount of the therapeutic agent is administered to the subject to treat a disorder or mitochondrial disorder, such as a neurodegenerative disease. In one embodiment, a formulation including the therapeutic agent can be administered to the subject systemically in the period from the time of, for example, up to hours, days, and/or weeks after the disease or disorder is diagnosed.

The therapeutic agents can be delivered to a subject by any suitable route, including, for example, local and/or systemic administration. Systemic administration can include, for example, parenteral administration, such as intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. In some embodiments, the therapeutic agent can be administered to the subject via intravenous administration using an infusion pump to deliver daily, weekly, or doses of the therapeutic agent.

Pharmaceutically acceptable formulations of the therapeutic agent can be suspended in aqueous vehicles and introduced through conventional hypodermic needles or using infusion pumps.

For injection, therapeutic agent can be formulated in liquid solutions, typically in physiologically compatible buffers such as Hank's solution or Ringer's solution. In addition, the therapeutic agent may be formulated in solid form and re-dissolved or suspended immediately prior to use. Lyophilized forms are also included. The injection can be, for example, in the form of a bolus injection or continuous infusion (such as using infusion pumps) of the therapeutic agent.

It will be appreciated that the amount, volume, concentration, and/or dosage of the therapeutic agent that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily be determined by one skilled in the art using the experimental methods described below.

In some embodiments, a therapeutic agent, such as a therapeutic peptide described herein, can be administered can be administered locally and/or systemically to a subject in need thereof at a dose or amount of about 0.1 µmol, about 1 µmol, about 5 µmol, about 10 µmol, or more; or about 0.0001 mg/kg, about 0.001 mg/kg, about 0.01 mg/kg, about 0.1 mg/kg, or about 1 mg/kg to about 5 mg/kg or 10 mg/kg of the subject being treated. The therapeutic agent can be administered daily, weekly, biweekly, monthly or less frequently.

In some embodiments, the therapeutic agent can be administered to a subject with a neurodegenerative disorder associated with aberrant ATAD3A activation, such as HD, at an amount effective to prolong survival, enhance motor activity, enhance striatal neuronal survival, improve mtDNA maintenance and bioenergetic activity, and decrease inflammation.

In other embodiments, a pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the method described herein can be treated with the therapeutic agent for at least 30 days (either by repeated administration or by use of a sustained delivery system, or both).

Approaches for sustained delivery include use of a polymeric capsule, a minipump to deliver the formulation, a biodegradable implant, or implanted transgenic autologous cells (see U.S. Pat. No. 6,214,622). Implantable infusion pump systems (e.g., INFUSAID pumps (Towanda, PA)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. Nos. 5,368,562 and 4,731,058.

Vectors encoding the therapeutic peptides can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

The following examples are included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example

In this Example, we identified ATAD3A as a candidate interactor with Drp1 using unbiased proteomics for Drp1-interacting proteins in neuronal cells derived from HD patient induced pluripotent stem cells (HD-iPS cells). We show that in HD, ATAD3A forms oligomers, which bridge Drp1-mediated mitochondrial fragmentation and mtDNA instability, leading to impaired mitochondrial biogenesis and neurodegeneration. We demonstrate that suppression of Drp1/ATAD3A binding by a peptide inhibitor DA1 is protective in various model of HD in vitro and in vivo.

Methods

Antibodies and Reagents

Protein phosphatase inhibitor, protease inhibitor cocktails, Flag peptide, GST control protein, and 3-nitropropionic acid (3-NP, N5636) were purchased from Sigma-Aldrich. DSP (dithiobis[succinimidylpropionate], 22585), DTSSP (3,3'-dithiobis[sulfosuccinimidylpropionate], 21578), and BMH (bismaleimidohexane, 22330) were purchased from Thermo Fisher Scientific. Antibodies used in this study are listed below: antibodies for Drp1 (61113, 1:1000) and OPA1 (612607, 1:1000) were purchased from BD bioscience. Antibodies of ATAD3A (H00055210-D01, 1:1000), Mfn1 (H00055669-M04, 1:1000), Mfn2 (H00009927-M01, 1:1000) were from Abnova. Antibodies of CHCHD3 (25625-1-AP, 1:1000), YME1L1 (11510-1-AP, 1:500), Mff (17090-1-AP, 1:1000), Fis1 (10956-1-AP, 1:1000), MIEF1 (20164-1-AP, 1:1000), and mtCO2 (55070-1-AP, 1:1000) were from ProteinTech; Tom20 (sc-11415, 1:1000), GFP (sc-9996, 1:2000), Myc (sc-40, 1:1000), Ac-lysine (AKL5C1, sc-32268), and GST (sc-138, 1:1000) antibodies were from Santa Cruz Biotechnology. Mitofilin (ab110329, 1:1000), Cytochrome C (ab110325, 1:10000), VDAC (ab14734, 1:2000), TFAM (ab131607, 1:2000), ClpP (ab124822, 1:2000), DARPP-32 (ab40801, 1:10000), and mitochondrial OXPHOS cocktail (ab110413, 1:1000) antibodies were from Abcam. FLAG (F3165, 1:2000) and β-Actin (A1978, 1:10000) antibodies were from Sigma. Antibody of PGC1α (3934-100, 1:500) was from Biovision. Anti-DNA (CBL186, 1:500) and anti-GAD67 (MAB5406, 1:500) antibodies were from Millipore. Antibodies of PSD95 (2507, 1:1000), Acetylated-Lysine (9441 S, 1:1000), and MAP2 (4542, 1:300) were from cell signaling. Iba1

(019-19741, 1:500) antibody was from Wako Chemicals. Antibody of Tau (T1308-1, 1:300) was purchased from rpeptide. HRP-conjugated anti-mouse and rabbit secondary antibodies were from Thermo Fisher Scientific. VeriBlot secondary antibody (HRP) (ab131366, 1:2000) that does not recognize heavy or light chains was from Abcam. Alexa 488/568/405 goat antimouse and rabbit secondary antibodies were from Life Technologies. Streptavidin beads (20357) were purchased from Thermo Fisher Scientific. Glutathionesepharose beads were obtained from GE Healthcare. GST-Drp1 recombinant protein was from Abnova.

Cells Culture

HEK293T, HeLa, and Neuro2A cells were cultured in DMEM supplemented with 10% (v/v) heat-inactivated FBS and 1% (v/v) antibiotics (100 unit/ml penicillin, 100 µg/ml streptomycin).

Drp1 WT and KO MEFs were obtained from Dr. Hiromi Sesaki (Johns Hopkins University). MFF WT and KO MEFs, as well as Fis1 KO MEFs, were obtained from Dr. David C. Chan (California Institute of Technology). MiD49 KO and WT MEFs were obtained from Mike Ryan (Monash Biomedicine Discovery Institute, Monash University). The cells were maintained in DMEM supplemented with 10% FBS and 1% penicillin/streptomycin.

HD patient fibroblasts (obtained from Coriell Institute, USA) and normal fibroblasts were maintained in MEM supplemented with 15% (v/v) FBS and 1% (v/v) penicillin/streptomycin.

iPS cells from a normal subject and a HD patient (carrying 41 CAG repeats) were differentiated into neurons using the protocol from our previous studies. Briefly, the iPS cells were plated onto 6-well plates precoated with 2.5% Matrigel and allowed to reach 90% confluence in feeder-free medium. For the first 10 days, the cells were treated with SB431542 (10 µM; Tocris Bioscience) and Noggin (100 ng/ml) in Neural Media (NM) containing Neurobasal and DMEM (1:1), B-27 supplement minus vitamin A (50×, Invitrogen), N2 supplement (100×, Invitrogen), GlutaMax (Invitrogen, 100×), FGF2 (20 ng/µl) and EGF (20 ng/µl), and 100 units/ml penicillin and 100 µg/ml streptomycin). For the next 10 days, the cells were treated with human recombinant Sonic hedgehog (SHH, 200 ng/ml), DKK1 (100 ng/ml) and BDNF (20 ng/ml), and 10 µM Y27632 (Sigma) in neuronal differentiation medium containing Neurobasal and DMEM (1:3), B27, N2, GlutaMax, and PS. Cells were then switched to treatment with BDNF (20 ng/ml), ascorbic acid (200 µM, Sigma-Aldrich), cAMP (0.5 mM, Sigma-Aldrich), and Y27632 (10 µM) in neuronal differentiation medium. All growth factors were purchased from PeproTech (Rocky Hill, NJ, USA). Twenty days after the initiation of differentiation, the neurons (about 5000 cells) were plated onto 12-mm poly-Dlysine/laminine-coated coverslips and grown in 24-well plates in neuronal differentiation medium.

All of the above cells were maintained at 37° C. in 5% $CO_2$-95% air.

Mouse striatal cell lines HdhQ7 and Q111 cells are immortalized from knock-in mice carrying 7 and 111 CAG repeats, respectively, in the mouse htt gene. HdhQ7 and HdhQ111 purchased from CHDI Foundation were cultured in DMEM supplemented with 10% (v/v) heat-inactivated FBS, 1% (v/v) penicillin/streptomycin, and 400 µg/ml G418 at 33° C. with 5% $CO_2$. Cells within 14 passages were used in all experiments.

Plasmids and Transfection

Human ATAD3A was amplified from HEK293T cDNA samples through standard PCR methods, and then cloned into pCMV-Myc, pcDNA3.1 (+)-Flag, pEGFP-N1 vectors. ATAD3A truncated mutants were constructed using overlap cloning techniques. ATAD3A point mutant K358E, and K135 mutants (K135E, K135R, K135Q, and K135A) and S2S48 mutants were constructed by using QuickChange II Site-Directed Mutagenesis Kit (Agilent Technologies). Drp1 truncated mutants were described in our previous study. Cells were transfected with plasmids using TransIT®-2020 transfection reagent (Minis Bio LLC, Madison, WI) according to manufacturer's instruction.

Knockdown of ATAD3A

For silencing ATAD3A, cells were transfected with control siRNA or mouse ATAD3A siRNA using TransIT-TKO Transfection Reagent (Minis Bio LLC, Madison, WI) following the protocol recommended by the manufacturer. The siRNA oligo sequences are as follows (only the sense strand is shown): control siRNA (non-targeting): UUCUCCGAACGUGUCACGU (SEQ ID NO: 13); ATAD3A: AGAUGGAGCUGAGGCAUAA (SEQ ID NO: 14) (Dharmacon, GE). For knockdown of ATAD3A in MEFs, control shRNA and ATAD3A shRNAs (Sigma, SHCLNGNM_179203) were lentivirally infected in MEFs followed by selection with 1 µg/ml puromycin. The information of shRNAs used here are as follows: shATAD3A #1 (TRCN0000242003), shATAD3A #2 (TRCN0000242004) and shATAD3A #3 (TRCN0000241479).

Drp1 Interactome

Forty days after neuronal differentiation, neuron culture derived from HD patient-iPS or normal subject-iPS cells were lysed in total lysis buffer (10 mM HEPES-NaOH, pH 7.9, 150 mM NaCl, 1 mM EGTA, 1% Triton X-100, and protease inhibitor cocktail). Three milligram of the lysates were immunoprecipitated using anti-Drp1 antibody overnight followed by 2 h incubation with protein A/G beads. Bound proteins were eluted by 0.1M glycine (pH 3.0). The proteins from each sample were then precipitated using 30% trichloroacetic acid (v/v), and the protein pellet was washed using ice-cold acetone. The pellet was air-dried, and the proteins were then trypsinized and analyzed by tandem mass spectrometry.

Digested peptides were reconstituted with 0.1% formic acid and analyzed by LC-MS/MS. Separation of peptides via capillary liquid chromatography was performed using Waters nanoAquity system (Waters Corp., Milford, MA). Mobile phase A (aqueous) contained 0.1% formic acid in 5% acetonitrile, and mobile phase B (organic) contained 0.1% formic acid in 85% acetonitrile. Separation was achieved using a C18 column (75 µm×20 cm, Waters Corp., Ethylene Bridged Hybrid column BEH300) through a 150 min gradient of 6 to 45% mobile phase B at a flow rate of 0.30 µL/min. Mass spectrometry analysis was performed using a hybrid linear ion trap Orbitrap Velos mass spectrometer (LTQ-Orbitrap Velos, Thermo, Waltham, MA). Survey scan was operated at 60,000 resolution, followed by eight standard collision-induced dissociation (CID) fragmentations in a datadependent manner. Dynamic exclusion was enabled as the following: repeat count, 2; repeat duration, 30 s; exclusion list size, 250; and exclusion duration, 120 s.

Acquired tandem mass spectra were searched against the Uniprot human protein database (downloaded on May 5, 2012), containing 40,464 protein entries. A decoy database containing the reversed sequences of all the proteins was appended to estimate false discovery rate. Protein identification using Sequest or ProLuCID and DTASelect was performed using the Integrated Proteomics Pipeline (IP2, Integrated Proteomics Applications, Inc. San Diego, CA). The precursor mass accuracy was limited to 15 ppm for spectra acquired; the product ions mass accuracy was set at 0.6 Da. Fully tryptic enzyme specificity and up to two missed cleavages were allowed. Static modifications included carbamidomethylation on cysteines (57 Da), and variable modifications included oxidation on methionines (16 Da). Isotopic C13 incorporated ions were automatically included. DTASelect was applied to generate search results of peptide-to-spectra matches (PSMs) with a max false discovery rate (FDR) of 5%, yielding a protein FDR of less than 1% with at least two peptides per protein being assigned.

Cellular location, molecular and cellular function, and enriched mitochondrial candidates of Drp1-interacting proteins were analyzed using Ingenuity IPA software.

Analysis of ATAD3A Oligomers

To analyze dimerization of ATAD3A under non-reducing conditions, the cells or tissues were harvested and lysed with total lysates buffer. An equal amount of proteins was subject to 8% SDS-PAGE analysis in the presence or absence of β-mercaptoethanol (β-ME). For in vitro BMH crosslinking, the cell lysates were incubated with 1 mM BMH at r.t. for up to 25 min and quenched with 0.1% β-ME, followed by SDS-PAGE analysis. For in-vivo crosslinking, the cells were treated with cell-permeable crosslinker BMH (1 mM) for 20 min at 37° C. After crosslinking, the cells were quenched in PBS with 0.1% β-ME. For DSP crosslinking, the cells were treated with cell-permeable crosslinker for 5 min at 37° C., followed by quenching and washing with 10 mM Glycine in PBS. For formaldehyde (FA) crosslinking, the cells were incubated with PBS buffer containing 1% FA for 20 min at r.t., and the crosslinking reaction was terminated by washing in PBS containing 100 mM glycine. The cells were then lysed and subject to 8% SDS-PAGE analysis. For DTSSP crosslinking of proteins in mitochondrial fractions, isolated mitochondria samples were suspended in the mitochondrial lysis buffer (250 mM sucrose, 20 mM HEPES-NaOH, pH 7.5, 10 mM KCl, 1.5 mM $MgCl_2$, 1 mM EDTA, 1 mM EGTA and protease inhibitor). An equal amount of crude mitochondria was incubated at 30° C. in the presence of 0.5 mM DTSSP. The cross-linking was terminated by the addition of SDS loading buffer. The samples were subject to 8% SDS-PAGE analysis.

Isolation of Mitochondria-Enriched Fractionations

Cells were washed with cold phosphate-buffered saline (PBS) and incubated on ice in mitochondrial lysis buffer (250 mM sucrose, 20 mM HEPES-NaOH, pH 7.5, 10 mM KCl, 1.5 mM $MgCl_2$, 1 mM EDTA, 1 mM EGTA, protease inhibitor cocktail, and phosphatase inhibitor cocktail) for 30 min. The cells were scraped and then disrupted 15 times by repeated aspiration through a 25-gauge needle. Mouse brains were minced and homogenized in mitochondrial lysis buffer to release mitochondria. The homogenates were spun at 800×g for 10 min at 4° C., and the resulting supernatants were spun at 12,000×g for 20 min at 4° C. The pellets were washed with lysis buffer and spun at 12,000×g again for 20 min at 4° C. The final pellets were suspended in lysis buffer containing 1% Triton X-100 and were mitochondrial-rich lysate fractions. The mitochondrial protein voltage-dependent anion channel (VDAC) was used as a loading control.

Rat Liver Mitochondrial Sub-Compartment Fractionations

Isolation of mitochondrial sub-compartmental fractionations including contact sites was described previously. Briefly, liver from one rat (male Lewis, 370 g) was used and mitochondria isolated by differential centrifugation and purified further by a Percoll gradient centrifugation. The mitochondrial pellet was slowly resuspended in 70 ml 20 mM potassium phosphate/0.2% defatted BSA, pH 7.2, and then incubated on ice for 20 min with gentle stirring to induce swelling and rupture of the mitochondrial outer membrane. After 20 min, ATP (0.5 M) and $MgCl_2$ (1 M) were added to a final concentration of 1 mM each and the mitochondrial suspension was incubated for an additional 5 min on ice with stirring. The swollen/shrunk mitochondria were centrifuged for 20 min at 4° C. at 22,550×g (Sorvall RC5C, SS-34 rotor), and the pellet was slowly resuspended in 70 ml 20 mM potassium phosphate/0.2% defatted BSA, pH 7.2. The mitochondrial suspension was treated with two strokes of a tight-fitting pestle (Potter-Elvjehem, setting 3) and centrifuged for 15 min at 4° C. with 1900×g (Sorvall RC5C, SS-34 rotor). The supernatant was carefully removed and centrifuged for 20 min at 22,550×g (Sorvall RC5C, SS-34 rotor) to obtain the crude outer membrane pellet. The pellet was resuspended in 0.6 ml of 20 mM potassium phosphate, pH 7.2 (13-17 mg protein/ml), using a hand-driven Potter homogenizer and separated into outer membranes, contact site fraction, and inner membranes by discontinuous sucrose gradient centrifugation.

The gradient was 1.2 ml each of 51.3, 37.7, and 25.2% sucrose in 20 mM potassium phosphate, pH 7.2; 0.8 ml (10.5-13.6 mg protein) of crude outer membrane fraction was loaded per tube and centrifuged for 60 min at 4° C. and 121,000×g (Beckman L8-M ultracentrifuge, SW 50.1 rotor). The membranous material at the 25.2%/37.7% (purified mitochondrial outer membranes) and 37.7%/51.2% (contact sites) interfaces were collected, diluted tenfold with cold 20 min potassium phosphate, pH 7.2, recovered by centrifugation for 1 h at 184,000×g (Beckman L8-M ultracentrifuge, 50.2Ti rotor), and resuspended in a small volume of 20 mM potassium phosphate, pH 7.2. The pellet at the bottom of the tube from the discontinuous sucrose gradient was resuspended in 20 mM potassium phosphate, pH 7.2 and used for analysis.

In Situ Proximity Ligation Assay (PLA)

HdhQ7 and HdhQ111 were grown overnight on glass coverslips. After washing with PBS, the cells were fixed with 4% paraformaldehyde for 20 mins at room temperature, permeabilized with 0.1% Triton X-100 in PBS for 5 mM, and blocked with PLA blocking buffer for 1 h at 37° C. The cells were then subject to the PLA using Duolink® In Situ Red Starter Kit Mouse/Rabbit assay kit (DU092101, Sigma) according to the manufacturer's instructions. Briefly, after blocking, the cells were incubated with rabbit anti-ATAD3A (1:500, Abcam, ab112572) and mouse anti-Mitofilin or mouse anti-Cytochrome C antibodies overnight at 4° C. The cells were then incubated with the PLA probes (Anti-Rabbit PLUS and Anti-Mouse MINUS) for 1 h at 37° C., followed by the ligation and amplification. In this assay, the oligonucleotides hybridize to the two PLA probes and join to a closed loop if they are in close proximity Amplification solution, consisting of nucleotides and fluorescently labeled oligonucleotides, was added together with polymerase. The oligonucleotide arm of one of the PLA probes acts as a primer for "rolling-circle amplification" (RCA) using the ligated circle as a template, and this generates a concatemeric product. Fluorescently labeled oligonucleotides hybridize to the RCA product. The PLA signal was visible as a distinct fluorescent spot and was analyzed by confocal microscopy (Fluoview FV1000, Olympus). The number of fluorescent signals was then quantitated using NIH Image J software.

Immunogold Electron Microscopy

The cultured HdhQ7 and HdhQ111 cells were processed for immunocytochemistry and examined as previously described. Grids were then incubated with the monoclonal antibody (anti-ATAD3A, Abcam ab112572) at 1:5, 1:25, and 1:50 dilution in phosphate buffered saline (PBS) containing 1% w/v bovine serum albumin and 0.01% v/v Tween 20 (PBT) for 12 h at 4° C. Negative controls included normal rabbit serum and PBT replaced as the primary antibody. After washing, grids were incubated for 2 h in 10 nm goldconjugated goat anti-rabbit IgG (BBInternational, Ted Pella, CA) diluted 1:30 in PBT, rinsed with PBS, and fixed with glutaraldehyde to stabilize the gold particles. For the enhancement of the mitochondria membrane, the grids were treated with the vapor fixation from osmium tetroxide. Samples were then stained with acidified uranyl acetate and Sato's triple lead stain, and examined in an FEI Tecnai Spirit (T12) with a Gatan US4000 4 k×4 k CCD.

Mass Spectrometry Analysis of Acetylated Lysine Residues

Total lysates of HdhQ7 and HdhQ111 cells were IP with anti-ATAD3A antibodies. The ATAD3A immunoprecipitates were subject to SDS-PAGE analysis followed by Coomassie Brilliant blue staining. The SDS-PAGE gel was then submitted for tryptic and chymotryptic digestion and LC-MS/MS analysis. Briefly, gel bands were manually excised. Gel bands were then cut to minimize excess polyacrylamide, divided into a number of smaller pieces. The gel pieces washed with water and dehydrated in acetonitrile. The bands were then reduced with DTT and alkylated with iodoacetamide prior to the in-gel digestion. All bands were digested in-gel using trypsin, by adding 5 µL 10 ng/µL trypsin in 50 mM ammonium bicarbonate and incubating overnight digestion at r.t. to achieve complete digestion. The peptides that were formed were extracted from the polyacrylamide in two aliquots of 30 µL 50% acetonitrile with 5% formic acid. These extracts were combined and evaporated to <10 µL in Speedvac and then resuspended in 1% acetic acid to make up a final volume of ~30 µL for LC-MS analysis. The LC-MS system was a ThermoScientific Fusion Lumos tribrid mass spectrometer system. The HPLC column was a Dionex 15 cm×75 µm id Acclaim Pepmap C18, 2 µm, 100 Å reversed-phase capillary chromatography column. Five µL volumes of the extract were injected and the peptides eluted from the column by an acetonitrile/0.1% formic acid gradient at a flow rate of 0.3 µL/min were introduced into the source of the mass spectrometer on-line. The microelectrospray ion source is operated at 2.5 kV. The digest was analyzed using the data dependent multitask capability of the instrument acquiring full scan mass spectra to determine peptide molecular weights and product ion spectra to determine amino acid sequence in successive instrument scans. The data were analyzed by using all CID spectra collected in the experiment to search the mouse or human UniProtKB with the search programs Sequest and Mascot. For post-translational modification analysis, the data from these bands was searched considering acetylation. In addition, a second LC-MS/MS experiment was carried out that corresponds to a parallel reaction monitoring (PRM) experiment which involves fragmentation of specific m/z ratios over the entire course of the LC experiment.

Real-Time PCR

Total RNA was isolated using RNeasy Mini Kit (QIAGEN), and 0.5-1 µg of total RNA was used to synthesize cDNA using QuantiTect Reverse Transcription Kit (QIAGEN). qRT-PCR was performed using QuantiTect SYBR Green (QIAGEN) and analyzed with the StepOnePlus Real-Time PCR System (Thermo Fisher Scientific). Three replicates were performed for each biological sample, and the expression values of each replicate were normalized against GAPDH cDNA using the 2-ΔΔCT method.

Measurement of mtDNA Content

Total DNA was isolated from cells using Blood and Cell culture kit (QIAGEN), and then subject to qPCR using QuantiTect SYBR Green (QIAGEN). Quantitative PCR was performed using nuclear primers (GAPDH or Tert) and mtDNA primers (mt-$CO_2$, mt-ND2, mt-CO1 and D-loop). Three technical replicates were performed for each biological sample, and the mtDNA abundance of each replicate were normalized against nuclear DNA using the 2-ΔΔCT method.

For isolation of DNA from mouse plasma, the QIAamp DNA Blood Mini Kit (QIAGEN) was used. Briefly, 100-200 µl mouse plasma was subjected to total DNA extraction. Then the eluted DNA was diluted (1:5) to perform the qPCR experiment.

TFAM-mtDNA Binding Assay

Total lysates were isolated from cells with the indicated treatments, and then incubated with biotinylated LSP DNA probe (Biotin-LSP) or LSP (control) overnight at 4° C. Then streptavidin agarose beads (Thermo Fisher Scientific) were added for 1 h at 4° C. After incubation, the biotinstreptavidin complex was washed 3-5 times (1 ml/time) at 4° C. and subject to western blot analysis. To validate the LSP binding specificity to TFAM, 10 times (molar ratio) of non-labeled LSP was pre-incubated with an equal amount of lysate for 2 h prior to addition of the biotin-LSP probe.

Measurement of mtDNA Lesion by Quantitative PCR

Because the movement of the polymerase on the template is blocked at a lesion, qPCR amplification is inversely proportional to the presence of DNA damage. The level of mtDNA lesion will be calculated by comparing the 10 kb mtDNA fragment amplification, as described previously. To correct for the possible variations in the rate of mtDNA replication, the amplification of 10 kb mtDNA fragment was normalized to the 91 bp small mtDNA amplicon. Specifically, Total DNA was isolated as shown above. The amplification profile consisted of a 45-s denaturation at 94° C., 22 cycles of denaturation for 15 s at 94° C., annealing/extension at 64° C. for 12 min, and a final extension at 72° C. for 10 min.

Immunofluorescence Analysis

Cells grown on coverslips were fixed with 4% paraformaldehyde for 20 mins at r.t., permeabilized with 0.1% Triton X-100 in PBS and blocked with 2% normal goat serum. The cells were then incubated with primary antibody (overnight, at 4° C.) followed by Alexa Fluor 568 or 488 secondary antibody (2 h, r.t.). After staining with Nuclei with Hoechst dye (1:10,000 dilution), the cells were mounted onto slides. The cells were imaged by Fluoview FV1000 microscopy (Olympus).

To examine mitochondrial superoxide production, the cells were stained with MitoSOX (Invitrogen, 5 µM for 10 min) at 37° C. The cells were then washed with PBS three times and mounted for the image analysis. At least 150 cells/group were counted and quantitated.

Neurons derived from iPS cells were stained with anti-Tom20 (a mitochondrial marker) and anti-GAD67 (a striatal neuronal marker). Quantitation of mitochondrial length along the neurites was conducted only in the neurons immuno-positive for GAD67. To analyze dendrite and axon outgrowth of neurons, cells were stained with anti-MAP2 (a dendritic marker) and anti-GAD67 or anti-Tau (an axonal marker) and anti-DARPP32 (a medium spiny neuron marker). The length of MAP2+ dendrite and Tau+ axon in the neurons immuno-positive for GAD67 or DARPP32 was quantitated, respectively. At least 50 neurons/group were counted.

For Iba1 immunofluorescence staining, mice were deeply anesthetized and transcardially perfused with 4% paraformaldehyde in PBS. Frozen brain sections (10 µm, coronal) were permeabilized with 0.1% Triton X-100 in TBS-T buffer followed by blocking with 5% normal goat serum. The brain sections were then incubated with anti-Iba1 antibody (1:500 dilution) for overnight at 4° C., followed by staining with Alex-488 anti-rabbit secondary antibody (1:2000 dilution). Iba1-immunopositive cells in the 100 $mm_2$ were quantitated by image J software.

LDH Assays

Cells were treated as described, and cell death was determined by using Cytotoxicity Detection Kit (LDH) according to protocols recommended by the manufacturer (Roche).

Rational Design of Peptide Inhibitor

In a similar approach to the peptide design for Drp1 peptide P110[56] and VCP peptide inhibitor HV-3[31], we used L-ALIGN sequence alignment software and identified one region of homology between Drp1 (human, NP_036192) and ATAD3A (human, NP_001164006). These regions are marked as regions DA1 and DA2, respectively. All the homologous sequences are conserved across a variety of species, including human, mouse, rat, and bovine. The peptides were synthesized at Ontores (Hangzhou, China) corresponding to regions DA1 and DA2 and conjugated to the cell permeating TAT protein-derived peptide, $TAT_{47-57}$. These peptides are referred to as DA1 (YGRKKRRQRRR-GG-EDKRKT-NH2 (SEQ ID NO: 16), Product number P103882, Lot #0P082714SF-01) and DA2 (YGRKKRRQRRR-GG-EERRKT-NH2 SEQ ID NO: 17), Product number: P103883. Lot #: 0P0827714SF-02). Note that $TAT_{47-57}$-based delivery was used in culture and in vivo and was found to be safe and efficacious for delivery of peptide cargoes to cells and also to cross the blood-brain-barrier. The purity was assessed as >90% by mass spectrometry. Lyophilized peptides were dissolved in sterile water and stored at −80° C. until use.

3D Modeling and Rendering of Protein Structure

The 3D structural model of the ATAD3A N-terminal segment (residues 1-210) (GenBank: AAH63607.1) was predicted by I-TASSER and graphically rendered using the PyMol Molecular Graphics System, version 1.7.4.0, Schrodinger, LLC. The 3D crystal structure of the Drp1 GTPase-GED fusion construct (PDB ID: 4H1U) was similarly rendered using PyMol. DA1 and DA2 were mapped on Drp1 and ATAD3A, respectively. The K135 was labeled in pink in the ATAD3A N-terminal structural model.

Measurement of Mitochondrial Respiratory Activity

Mitochondrial respiration activity in HdhQ7 and HdhQ111 cells was analyzed using a Seahorse Bioscience XFp Extracellular Flux Analyzer. The cells were seeded in XFp 6-well microplates at 6,000 cells per well in 50 µl of growth medium. One hour prior to measuring oxygen consumption, the cell culture media was replaced with XF assay medium and maintained in a non-$CO_2$ incubator for 1 h. The sensor cartridges were placed in the XFp Analyzer according to the manufacturer's instructions for the Mito Stress Test kit. In brief, mitochondrial function was determined by the sequential injection of oligomycin A (2.5 µg/mL), FCCP (1 µM), and antimycin A (4 µM). Following each experiment, the total cellular number of each well was determined using DAPI staining.

Immunoprecipitation

Cells and mouse brain tissues were harvested and lysed in total lysis buffer (10 min HEPES-NaOH, pH 7.9, 150 min NaCl, 1 min EGTA, 1% Triton X-100, and protease inhibitor cocktail) for 30 mins on ice and centrifuged at 12,000×g for 10 min at 4° C. The supernatants were incubated with the indicated primary antibodies or control IgG (sc-2025 and sc-2027, Santa Cruz Biotechnology) overnight at 4° C., followed by incubation with protein A/G beads (sc-2003, Santa Cruz Biotechnology) for 2 h at 4° C. The immunoprecipitates were washed with lysis buffer three times for a total of 30 min and then subject to WB analysis.

For Drp1-Mff or Drp-MiD51 (MIEF1) interaction, the cells were cross-linked by 1 min DSP for 10 min at r.t., then 10 min Glycine in PBS was added to quench the redundant DSP activity. For Drp1-Fis1 interaction, the cells were cross-linked by 1% FA for 20 min at r.t., then added 10 min Glycine in PBS to quench the redundant activity. The cells were washed with PBS, sonicated, and lysed with 1% Triton X-100 total lysis buffer.

For biotin-DA1 binding assay, biotin-DA1 and biotin-TAT (10 µM, each) were incubated with total lysates of cell cultures for overnight at 4° C. followed by the incubation with streptavidin beads for 1 h Immunoprecipitates were washed four times with cell lysate buffer and were analyzed by SDS-PAGE and immunoblotting.

Preparation of ATAD3A Protein

Using pcDNA3.1 (+)-ATAD3A-Flag plasmid as template, ATAD3A-Flag protein was synthesized by TNT® Quick Coupled Transcription/Translation System (Promega, Cat #L1170) followed by protein purification with Flag-peptide (Sigma, F3290). The expression of ATAD3A protein was confirmed by western blot analysis with both anti-ATAD3A and anti-Flag antibodies. This approach provides convenient single-tube, coupled transcription/translation reactions for eukaryotic cell-free protein expression and has been used to detect direct protein-protein interaction.

GST Pulldown Assay

GST-Drp1 or GST control protein were incubated with Glutathione-beads in TBST buffer at r.t. After 1 h of incubation, ATAD3A-Flag protein was added, and thoroughly mixed in vibrating mixer for 30 mins at r.t., then transferred to 4° C. for overnight incubation Immunoprecipitates were then washed for three time and analyzed by SDS-PAGE.

To test the inhibitory function of DA1 peptide on in vitro binding between GST-Drp1 and ATAD3A-Flag, DA1 peptide or control peptide TAT (60 µM, each) was incubated with ATAD3A-Flag protein before mixing with GST-Drp1-glutathione beads complex.

In Vitro Binding Assay

GST-Drp1 and ATAD3A-Flag proteins (2 µg, each) were incubated in the buffer (20 min HEPES [pH 7.4], 100 mM KCL, 2 min $MgCl_2$) for 30 min at RT, and followed with Flag antibody incubation at 4° C. for overnight. The mixture was then incubated with protein A/G beads for 2 h followed by immunoprecipitation. Note that no crosslinker was added in these in vitro binding assays.

For biotin-DA1 binding assay, biotin-DA1 and biotin-TAT (10 µM, each) were incubated with GST-Drp1 or ATAD3A-Flag protein for overnight at 4° C. followed by the incubation with streptavidin beads for 1 h Immunoprecipitates were washed four times with cell lysate buffer and were analyzed by SDS-PAGE and immunoblotting.

Drp1 GTP hydrolysis was monitored as a function of time as described previously.

Western Blot Analysis

Protein concentration was measured by protein assay dye reagents (Bio-rad). The protein was resuspended in Laemmli buffer, loaded on SDS-PAGE, and transferred onto nitrocellulose membranes. Membranes were probed with the indicated antibodies, followed by visualization with ECL. Representative blots have been cropped for presentation.

Animal Models of HD

All animal experiments were conducted in accordance with protocols approved by the Institutional Animal Care and Use Committee of Case Western Reserve University and were performed based on the National Institutes of Health Guide for the Care and Use of Laboratory Animals. Sufficient procedures were employed for reduction of pain or discomfort of subjects during the experiments.

Male R6/2 mice and their wild-type (WT) littermates (5 weeks old) were purchased from Jackson Laboratories [Bar Harbor, ME; B6CBA-TgN (HD exon1) 62; JAX stock number: 006494]. These mice (C57BL/6 and CBA genetic background) are transgenic for the 5' end of the human HD gene carrying 100-150 glutamine (CAG) repeats.

YAC128 [FVB-Tg(YAC128)53Hay/J, JAX stock number: 004938] breeders (FVB/N genetic background) were purchased from Jackson Laboratories. The YAC128 mice contain a full-length human huntingtin gene modified with a 128 CAG repeat expansion in exon 1. The mice were mated, bred, and genotyped in the animal facility of Case Western Reserve University. Male mice at the ages of 2, 3, 6, 9, and 12 months were used in the study.

All mice were maintained at a 12-hour light/dark cycle (on 6 am, off 6 μm).

Systemic peptide treatment in HD mice. All randomization and peptide treatments were prepared by an experimenter not associated with behavioral and neuropathology analysis. Male R6/2 mice (Tg) and their age-matched wild-type littermates (Wt) (6-week-old) were implanted with a 28-day osmotic pump (Alzet, Cupertino CA, Model 2004) containing TAT control peptide or DA1 peptide, which delivered peptides at a rate of 1 mg/kg/day. Male YAC128 mice (Tg) and their age-matched wild-type littermates (WT) were treated with TAT control peptide or DA1 peptide (1 mg/kg/day) by Alzet osmotic pump starting from the age of 3 months. The pump was replaced once every month.

Behavioral Analysis in HD Mice

All behavioral analyses were conducted by an experimenter who was blinded to genotypes and treatment groups.

Gross locomotor activity was assessed in R6/2 mice and age-matched wild-type littermates at the ages of 12 weeks, and in YAC128 mice and age-matched wildtype littermates at the ages of 2, 3, 6, 9, and 12 months. The mice were placed in the center of an activity chamber (Omnitech Electronics, Inc) and allowed to explore while being tracked by an automated beam system (Vertax, Omnitech Electronics Inc). Distance moved, horizontal and vertical activities were recorded. In R6/2 mice and wildtype littermates, one-hour locomotor activity was conducted. In YAC128 mice and wildtype littermates, 24 h of locomotor activity analysis was performed.

Hindlimb clasping was assessed with the tail suspension test once a week from the ages 8 to 12 weeks in R6/2 mice. The mice were suspended by the tail for 60 s, and the latency for the hindlimbs or all four paws to clasp was recorded using the score system: Clasping over 10 s, score 3; 5-10 s, score 2; 0-5 s, score 1; and 0 s, score 0.

The body weight and survival rate of HD mice and wild-type littermates were recorded throughout the study period.

Immunohistochemistry

Mice were deeply anesthetized and transcardially perfused with 4% paraformaldehyde in PBS. Brains were processed for paraffin embedment. Brain sections (10 μm, coronal) were used for immunohistochemical localization of DARPP-32 (1:500, Abcam) or ATAD3A (1:200, Genetex) using the IHC Select HRP/DAB kit (Millipore). Quantitation of DARPP-32 immunostaining was conducted using NIH image J software. The same image exposure times and threshold settings were used for sections from all treatment groups. An experimenter blinded to the experimental groups conducted the quantitation.

Striatum Volume

Coronal sections (10 μm) spaced 200 μm apart throughout the striatum will be stained with anti-NeuN (Sigma, MAB377, 1:200 dilution) antibody followed by secondary antibodies and detection with diaminobenzidine (DAB, Pierce). The perimeter of the striatum will be traced in each of the serial sections using a ×2 objective. For the volume estimation, consecutive sections (an average of 10-15 sections/animal) will be visualized and the perimeter of the striatum will be outlined. The striatal volume will be estimated by multiplying the sum of all the sectional areas (mm2) by the distance between successive sections (200 μm).

Dendrite Morphology of Medium Spiny Neuron in Mice

Dendrite morphology of medium spiny neurons in wild-type and HD R6/2 mice was analyzed by Golgi-Cox staining using Novaultra Golgi-Cox Stain Kit (IHCWorld, SKU IW-3023). Briefly, mice were deeply anesthetized and transcardially perfused with 4% paraformaldehyde in PBS. After thoroughly washing with PBS overnight, mouse brains were immersed in the Golgi-Cox solution in dark at room temperature, then replaced with fresh Golgi-Cox Solution after 2 days of immersion and continued the impregnation at room temperature in dark for 14 days following the manufactory instruction. After washing with PBS for 2 days, serial coronal sections of 200 μm thick were cut on Vibratome Series 1000 Sectioning System. The coronal sections were washed with water and stained with Post-Impregnation Solution for 10 min in dark at room temperature. Following the 3 times of washing with water, the brain sections were mounted on Superfrost plus slides (Thermo Scientific). Medium spiny neurons in striatum were selected for analysis. Total dendritic length per neuron was measured using NIH Image J plug-in simple neurite tracer.

Statistical Analysis

Sample sizes were determined by a power analysis based on pilot data collected by our labs or published studies. In the animal studies, we used n=15-20 mice/group for behavioral tests, n=14-15 mice/group for recording survival rate and body weight, n=6-9 mice/group for biochemical analysis, and n=6 mice/group for pathology studies. In the cell culture studies, we performed each study with at least three independent replications. For all of the animal studies, we ensured randomization and blinded conduct in experiments. For all imaging analyses, an observer who was blind to the experimental groups conducted the quantitation. No samples or animals were excluded from the analysis.

Data were analyzed by Student's t test for comparison of two groups or ANOVA with post-hoc Tukey's test for comparison of multiple groups. Survival rate was analyzed by Log-rank (Mantel-Cox) test and behavioral tests were analyzed by repeated-measure two-way ANOVA. Data are expressed as mean±SEM. Statistical significance was considered achieved when the value of p was <0.05.

Results

ATAD3A is a Binding Protein of Drp1 in HD

Figure 1B:
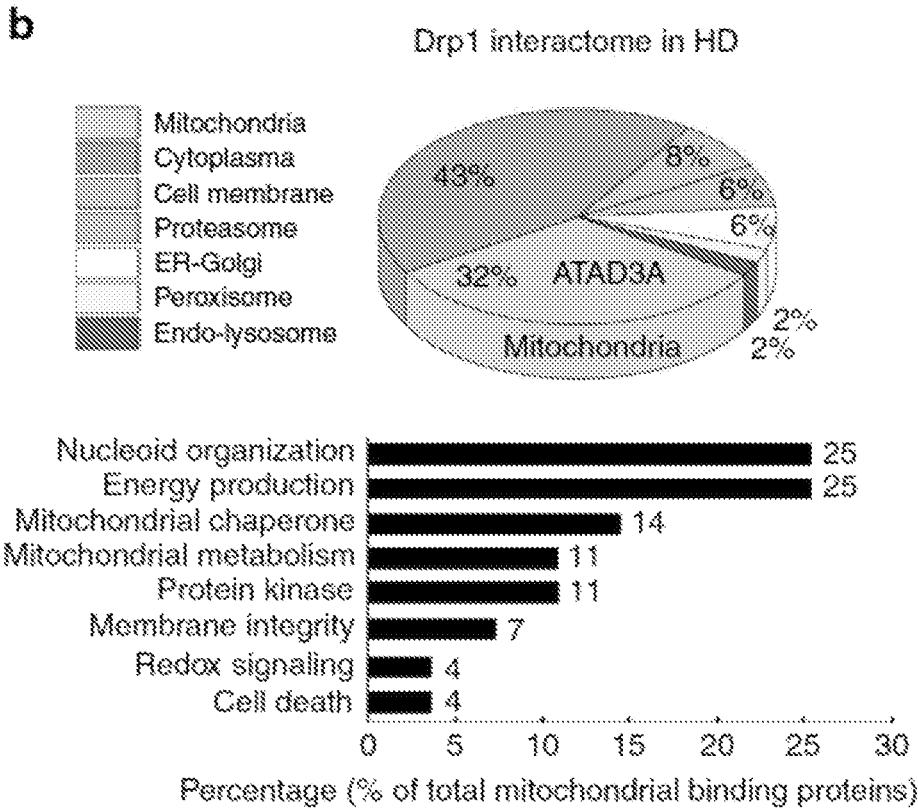

Using unbiased proteomic analysis, we set out to identify protein candidates that interact with Drp1 in striatal neurons derived from HD patient iPS cells. Tandem mass spectrometry analysis following affinity purification identified 91 proteins that putatively bound to Drp1 in HD patient cells but not in cells derived from normal subject-iPS cells. These proteins are involved in multiple pathways of cellular functions (FIG. 1A). Focusing on the protein candidates located on mitochondria, we detected enrichment of the proteins involved in mitochondrial nucleoid organization and energy production (FIG. 1B). Among these candidates, ATAD3A, a component of the mitochondrial nucleoid complex, ranked as the top candidate for Drp1 binding in HD neuronal cells (FIG. 1B).

Figure 1C:
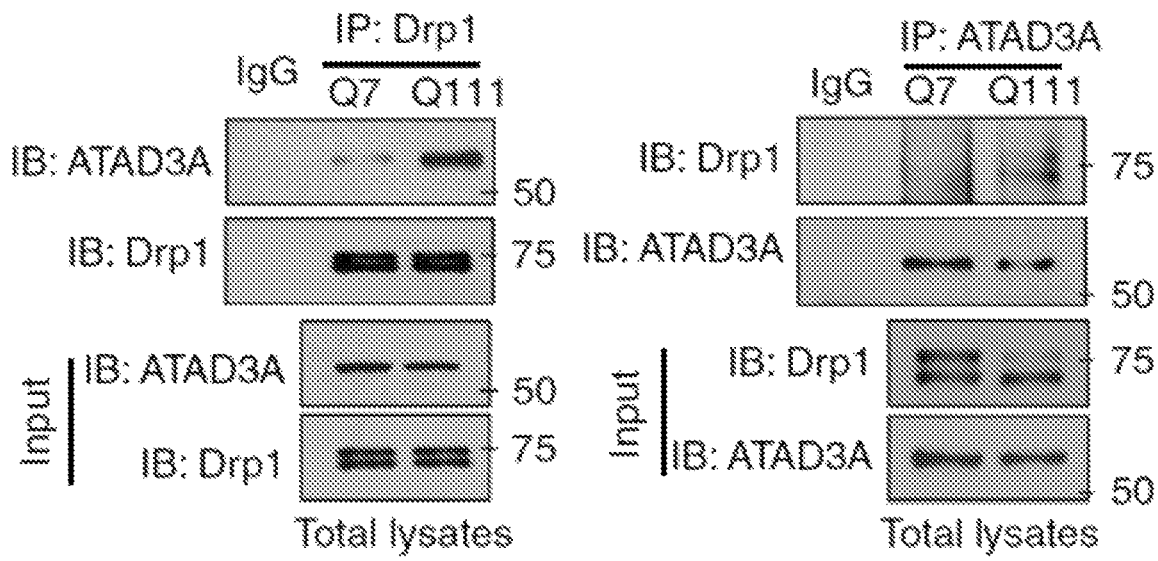
Figure 1D:
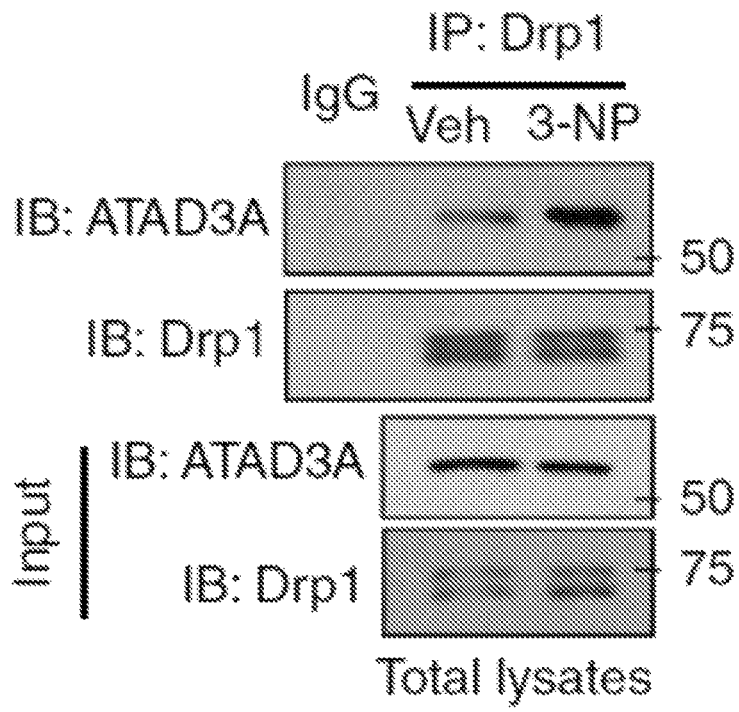
Figure 1E:
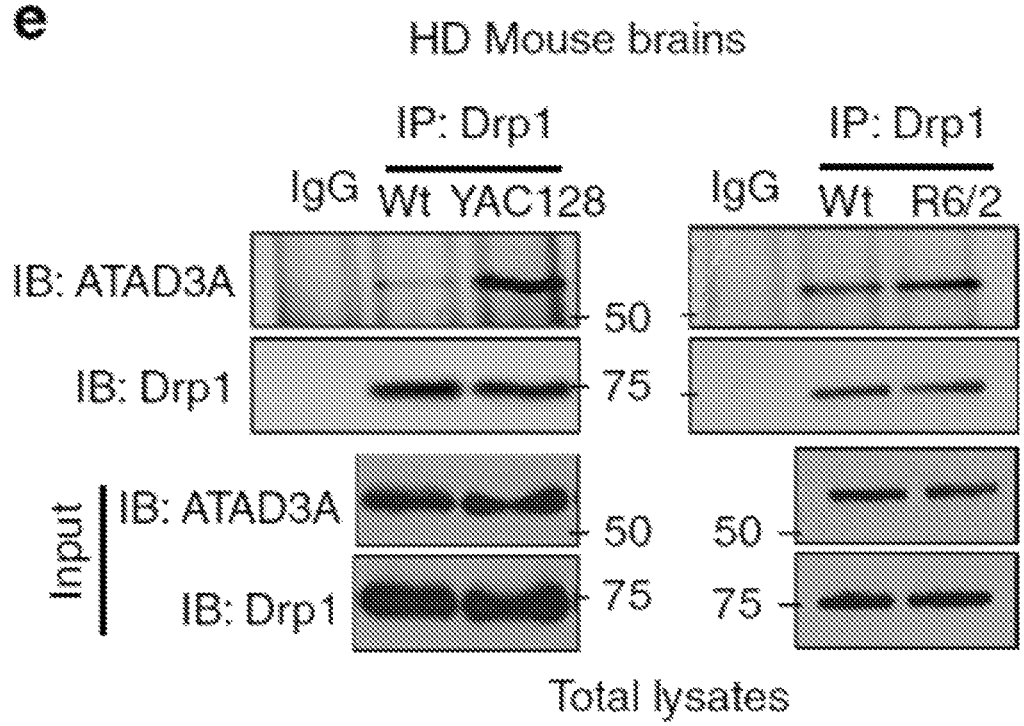
Figure 1F:
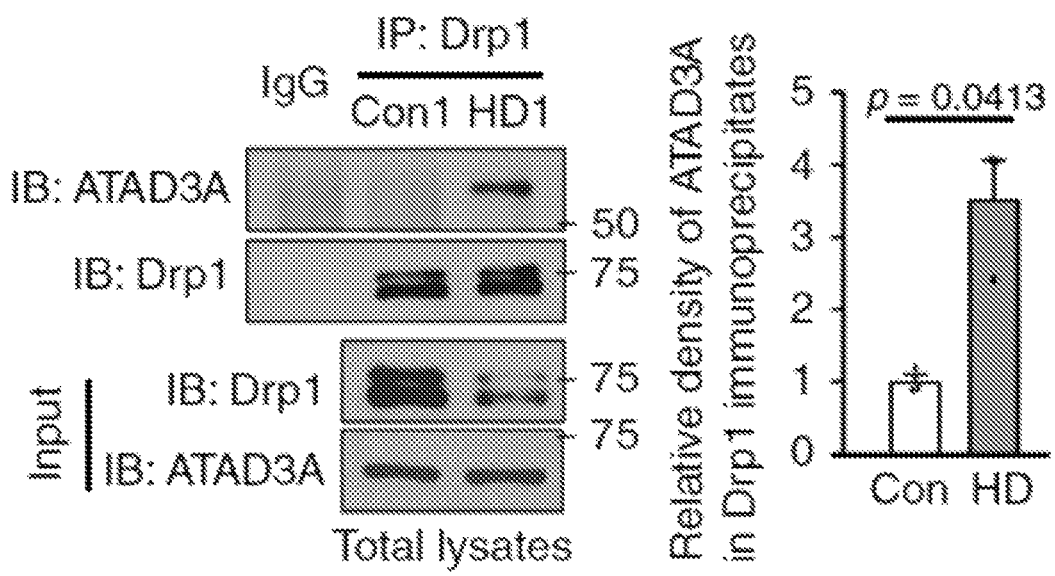
Figure 1G:
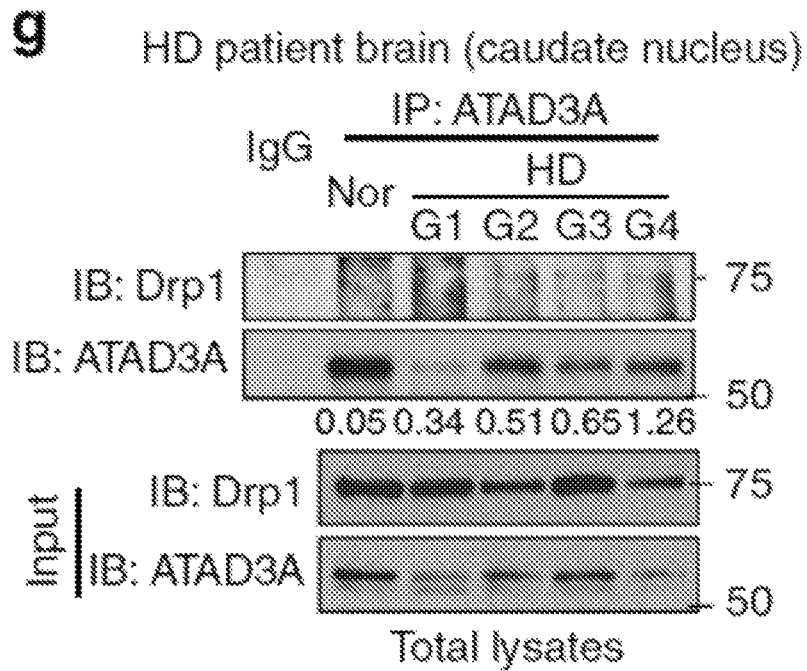

Immunoprecipitation (IP) analysis demonstrated a greater interaction between Drp1 and ATAD3A in HdhQ111 cells than in HdhQ7 cells (FIG. 1C). In wildtype mouse striatal cells, 3-nitropropionic acid (3-NP), a neurotoxin causing HD-like symptoms in rodents and primates, induced an interaction between Drp1 and ATAD3A (FIG. 1D). ATAD3A preferentially bound to Drp1 in striatal protein lysates of HD YAC128 and R6/2 mice relative to those of wildtype mice (FIG. 1E). Consistently, increased binding of Drp1/ ATAD3A was observed in HD patient fibroblasts (FIG. 1F) and HD patient postmortem brains (FIG. 1G), suggesting a role of the interaction in human HD.

Figure 1H:
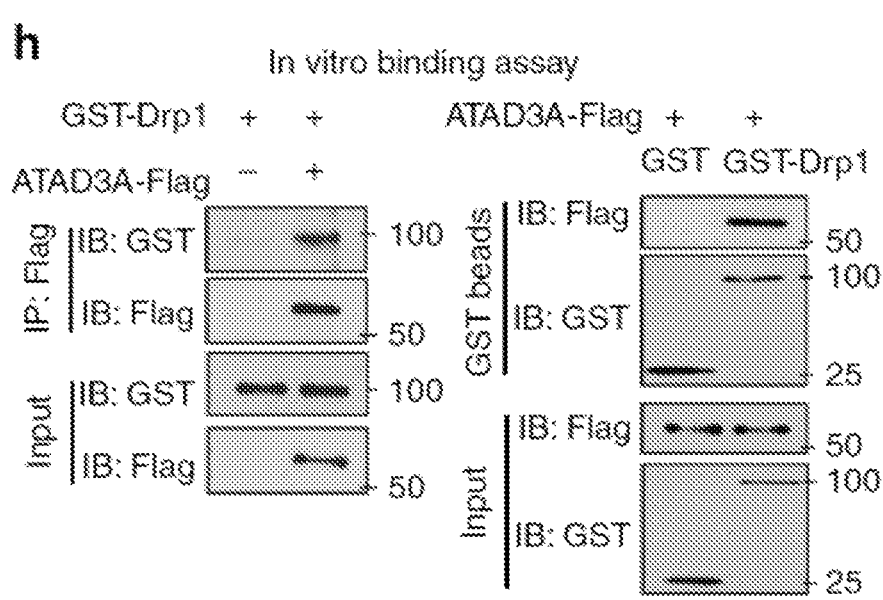

In vitro protein binding assay showed that GST-Drp1 and ATAD3A-Flag protein interacted (FIG. 1H). To map the domain interaction between ATAD3A and Drp1, we constructed several truncated mutants of ATAD3A, including ATAD3A ΔN50, which lacks the first 50 amino acids of the N-terminus; ATAD3A ΔCC, in which the two coiled-coil (CC) domains of ATAD3A are deleted; and ATAD3A ΔN245, which lacks N-terminal 245 amino acids and only contains a part of TM domain and ATPase domain. By IP analysis, we demonstrated that ATAD3A CC domain bound to Drp1 GTPase domain.

Collectively, our data demonstrate that Drp1 directly binds to ATAD3A and that the binding is elevated in HD.

Oligomerization of ATAD3A Increases in HD

Figure 2A:
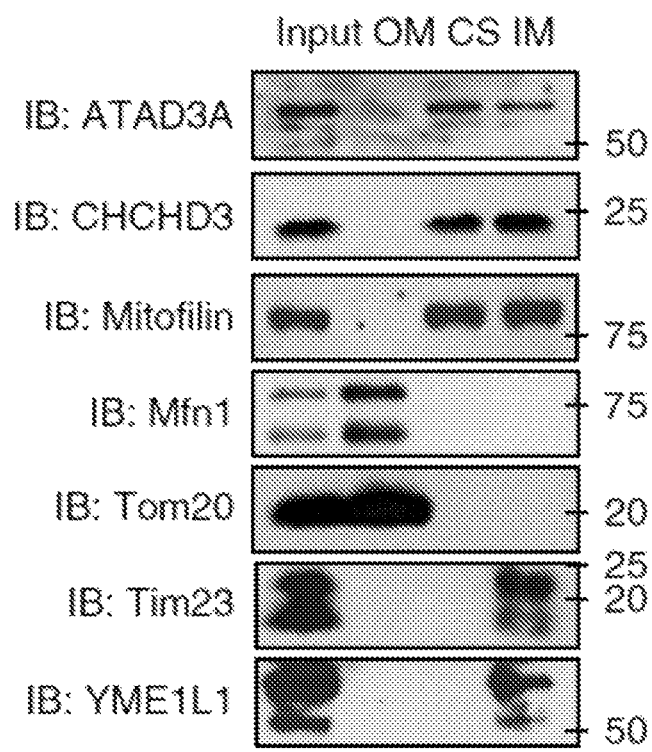
FIGS. 2(A-H) illustrate immunoblots, images, and graphs showing enhanced ATAD3A oligomerization in HD models. (A) Western blot (WB) analysis of rat liver mitochondrial fractionations with the indicated mitochondrial antibodies. OM: mitochondrial outer membrane. CS: contact sites. IM: mitochondrial inner membrane. (B) HdhQ7 and HdhQ111 cells were stained with anti-ATAD3A and anti-Mitofilin (a mitochondrial contact site protein) or anti-Cyto C (a mitochondrial intermembrane space protein) antibodies. Nuclei were stained with DAPI. In situ Duolink proximity ligation assay (PLA) was performed. Histogram: quantitation of the number of PLA positive signals. At least 200 cells/group were analyzed. 3 independent experiments, unpaired Student t-test. Scale bar: 10 µm. (C) Immunogold electron microscopy analysis with an antibody directed against ATAD3A N-terminus was performed in HdhQ7 and HdhQ111 cells. Bottom images are the images boxed. Scale bar: 100 nm. Histogram: the percentage of ATAD3A immunopositive gold particles on the contact site versus total number of gold particles. 3 independent experiments, unpaired Student t-test. (D) Left: ATAD3A protein level was determined by WB in the presence or absence of β-ME. Right: Protein lysates were incubated with the crosslinker BMH (1 mM). (E) HdhQ7 and Q111 cells were treated with BMH (1 mM, 20 min). (F) Total lysates of striatum from YAC128 (12 months old), R6/2 (12 weeks old), or age-matched wildtype mice were analyzed by WB with anti-ATAD3A antibody in the presence or absence of β-ME. n=6-10 mice/group. (G) ATAD3A oligomers were analyzed in HD patient fibroblasts (HD1: GM21756, Female; HD2: GM04693, Male; HD3: GM21756, Female) and normal subjects (Con 1: nHDF, fibroblasts from juvenile; Con 2: HDF, fibroblasts from adult; Con 3: Huf1822, adult). (H) ATAD3A oligomers were analyzed in total lysates of HD patient postmortem brains (cortex: left; caudate nucleus: right) or normal subjects, under non-reducing condition. [Cortex: Normal X5302; HD X5298. Caudate nucleus: Normal 5214; HD Grade1 (G1): 4283; HD Grade2 (G2): 4557; HD Grade3 (G3): 3573]. See FIG. 9F for patient information. The data are mean±SEM. Shown representative blots are from at least 3 independent experiments.
Figure 2B:
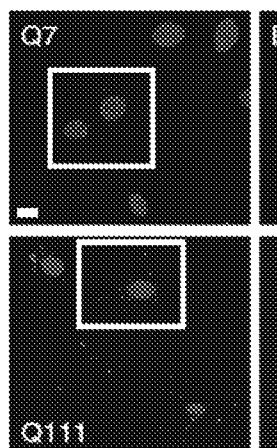
Figure 2B:
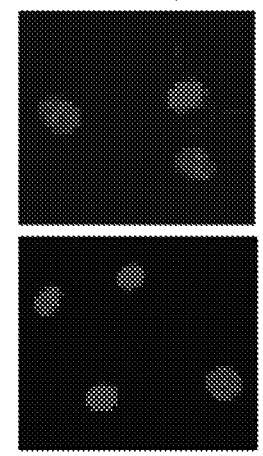
Figure 2B:
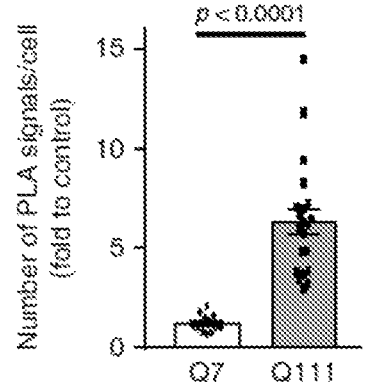
Figure 2C:
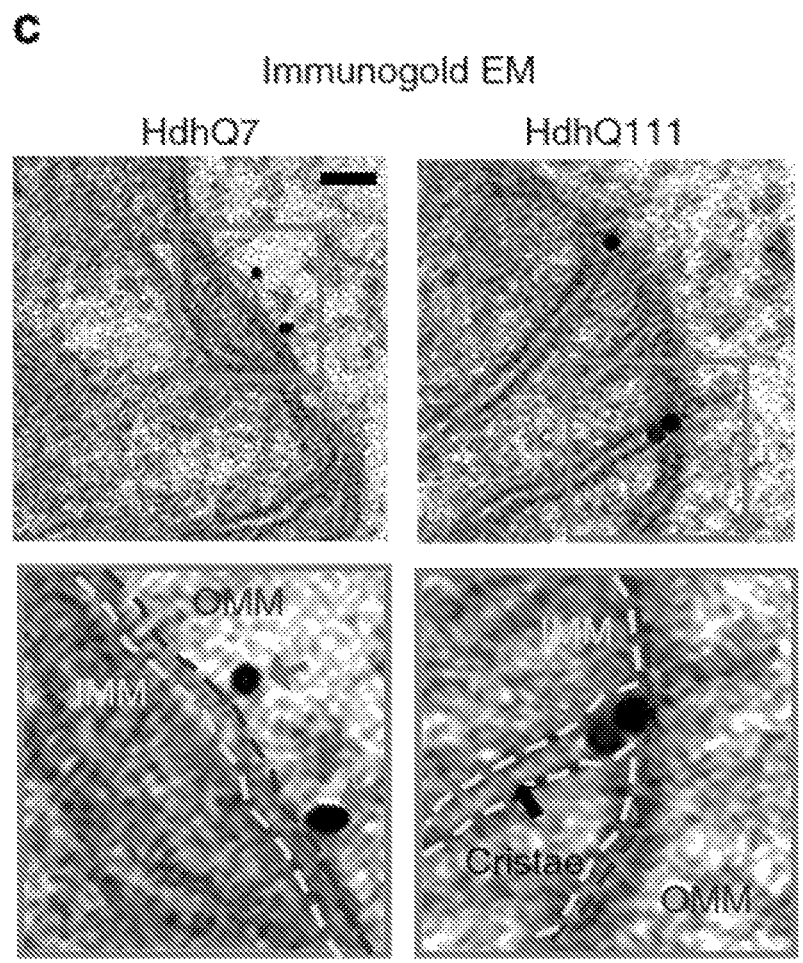
Figure 2C:
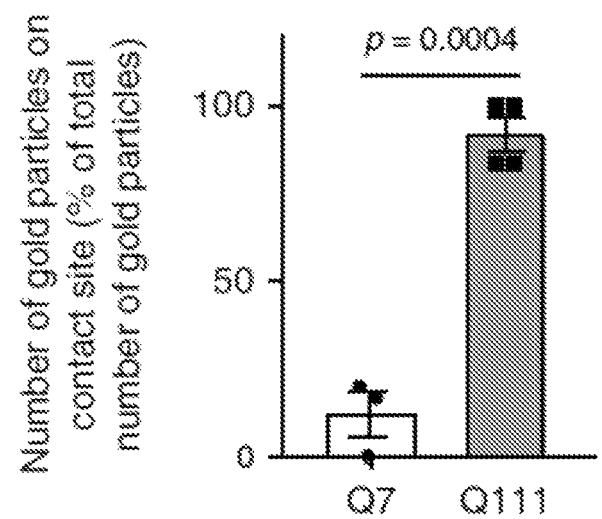

Western blot analysis of rat liver mitochondrial sub-compartmental fractionations revealed that ATAD3A was located on both contact sites and the inner membrane (IMM) (FIG. 2A). CHCHD3 and Mitofilin, two proteins located on the contact sites, were found in the same fractionations as ATAD3A (FIG. 2A). To quantify the mitochondrial sub-compartmental location of ATAD3A in HD, we applied in situ Duolink proximity ligation assay (PLA) which allows us to examine the endogenous ATAD3A location by determining the proximity between ATAD3A and the markers of mitochondrial sub-compartments. We observed a more than 5-fold increase in the PLA positive signals in HdhQ111 cells relative to HdhQ7 cells after staining the cells with anti-ATAD3A and anti-mitofilin (a mitochondrial contact site marker) antibodies (FIG. 2B). PLA positive signal was observed in neither HdhQ7 nor HdhQ111 cells stained with anti-ATAD3A and anti-cytochrome c (a mitochondrial intermembrane space protein) (FIG. 2B) Immunogold electron microscopy consistently showed that gold particles immuno-labeled with anti-ATAD3A antibody (directed against ATAD3A N-terminus) accumulated at the contact sites that connect the outer membrane (OMM) and the IMM in HdhQ111 cells (FIG. 2C). In contrast, in HdhQ7 cells, the gold particle-labeled ATAD3A N-terminus was located to the cytosolic side of the OMM (FIG. 2C). These data indicate an enhanced localization of ATAD3A at contact sites in HD cells.

Figure 2D:
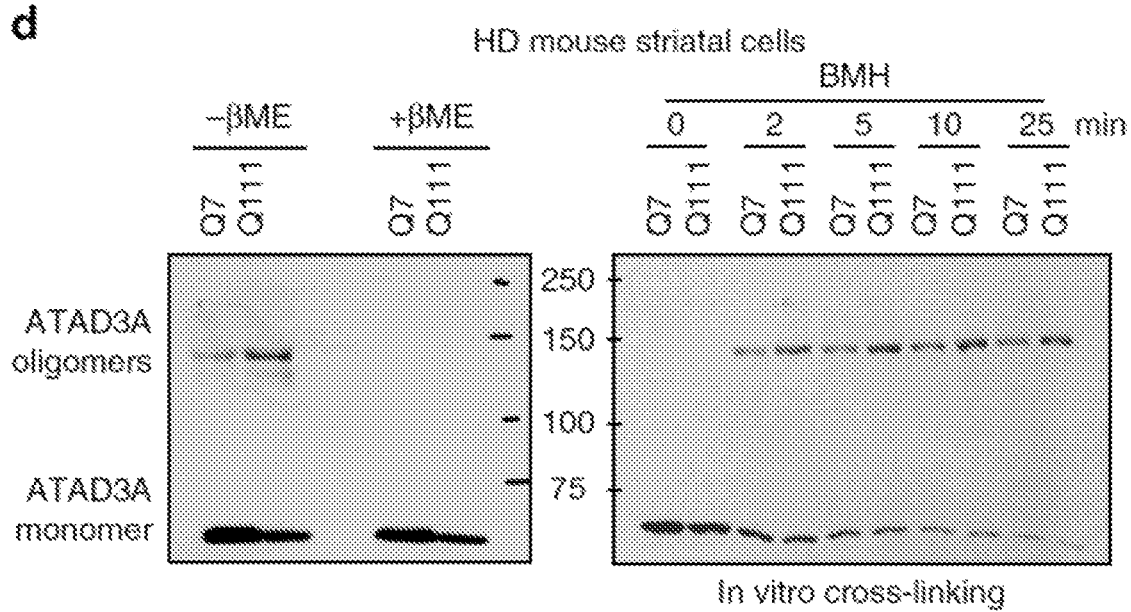
Figure 2E:
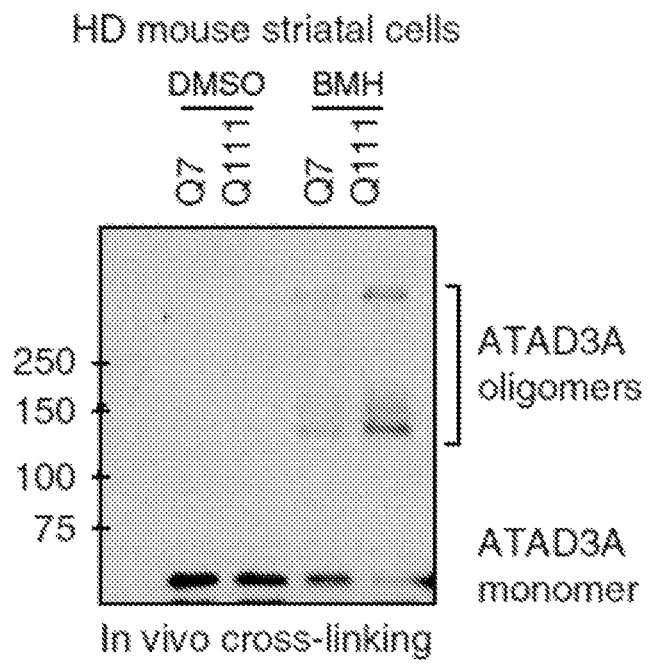
Figure 2F:
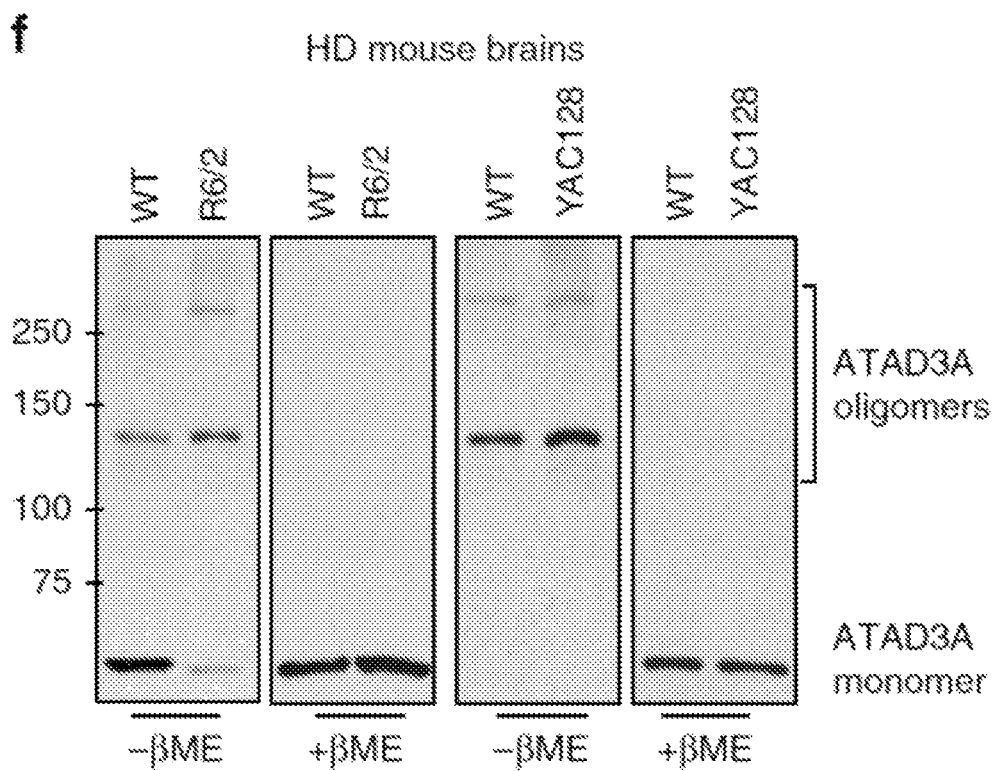
Figure 2G:
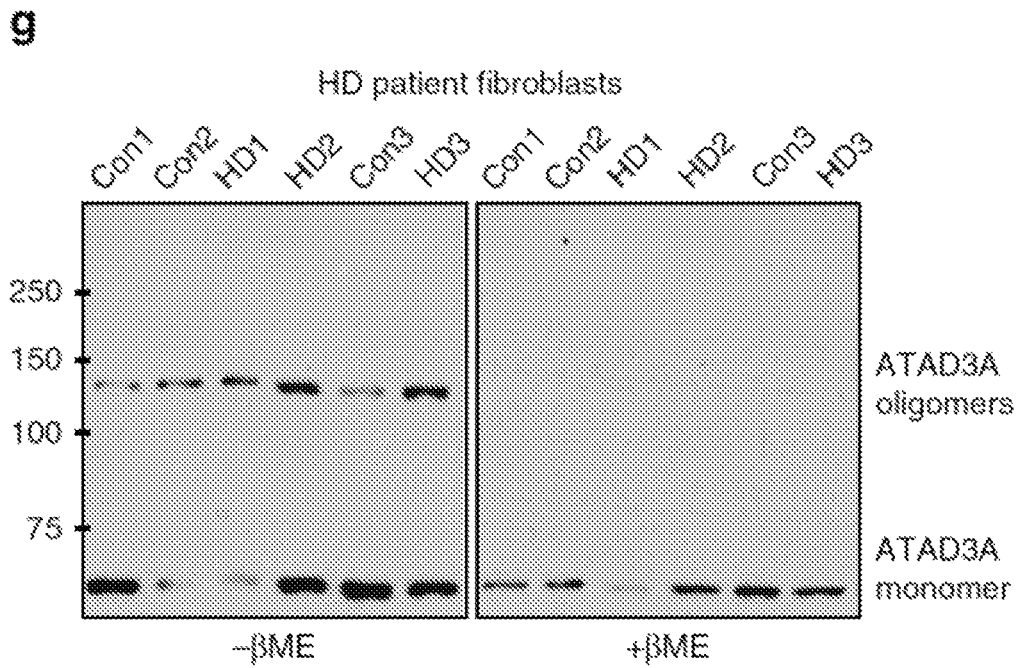
Figure 2H:
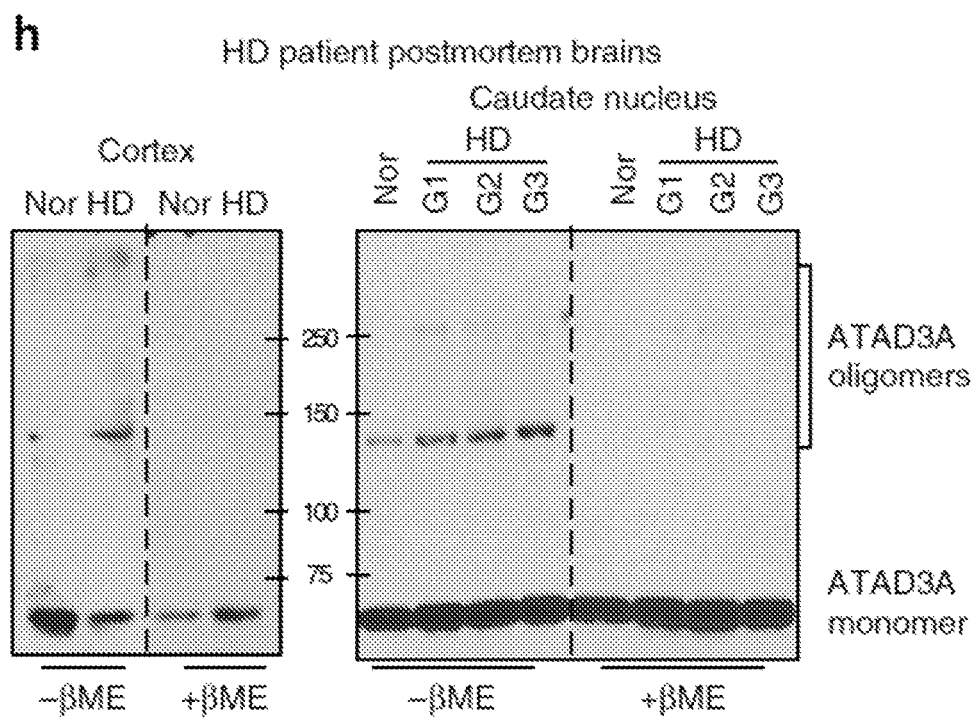

Structural prediction identified two CC domains within the N terminus of ATAD3A that may participate in higher-order ATAD3A oligomerization. Under non-reducing conditions, ATAD3A dimerization increased both in HdhQ111 cells (FIG. 2D) and in Neuro2a cells exposed to 3-NP. Both the addition of the chemical crosslinker BMH (bismaleimidohexane) to total cell lysates (in vitro cross-linking) and the treatment of cells with BMH (in vivo cross-linking) led to increased oligomerization of ATAD3A, the extent of which was consistently greater in HdhQ111 cells than in HdhQ7 cells (FIG. 2D). The increased oligomers of ATAD3A was again observed in mitochondrial fractions of HdhQ111 cells after cross-linking with DTSSP (3,3'-dithiobis(sulfosuccinimidyl propionate)) and in total lysates of HEK293 cells after crosslinking with DSP (dithiobis(succinimidyl propionate)). Notably, ATAD3A oligomers increased in HD YAC128 and R6/2 mouse striata (FIG. 2F), HD patient fibroblasts (FIG. 2G), and HD patient postmortem cortex and caudate nucleus (FIG. 2H, under non-reducing conditions. Our results demonstrate an increase of ATAD3A oligomerization in HD, suggestive of ATAD3A aberrant activation.

After transfecting the truncated mutants of ATAD3A in HEK293 cells, we found that the ΔN50 mutant showed greatly elevated ATAD3A dimers under the non-reducing conditions, whereas both ΔCC and ΔN245 mutants lacking the CC domain abolished the dimerization. In cells treated with 1% formaldehyde (FA) for crosslinking, ATAD3A ΔN50 was readily oligomerized, and the ΔCC and ΔN245 mutants lost this capacity. Myc-tagged ATAD3A can form heterodimers with flag-tagged ATAD3A, and deletion of the CC domain (ΔCC and ΔN245) completely blocked the heterodimer (FIG. 10G). Thus, the CC domain of ATAD3A is required for ATAD3A oligomerization.

The immuno-density of ATAD3A greatly increased in HD YAC128 and R6/2 mouse cortex and HD patient caudate nucleus. The protein levels of ATAD3A were unaltered in both mitochondrial fractions and total protein extracts of HD mouse striatum, excluding the possibility that enhanced ATAD3A dimerization is due to increased protein expression. This increased immunodensity of ATAD3A may be the result of enhanced ATAD3A oligomerization.

ATAD3A CC Domain is Required for Drp1 Fission Activity

Figure 3A:
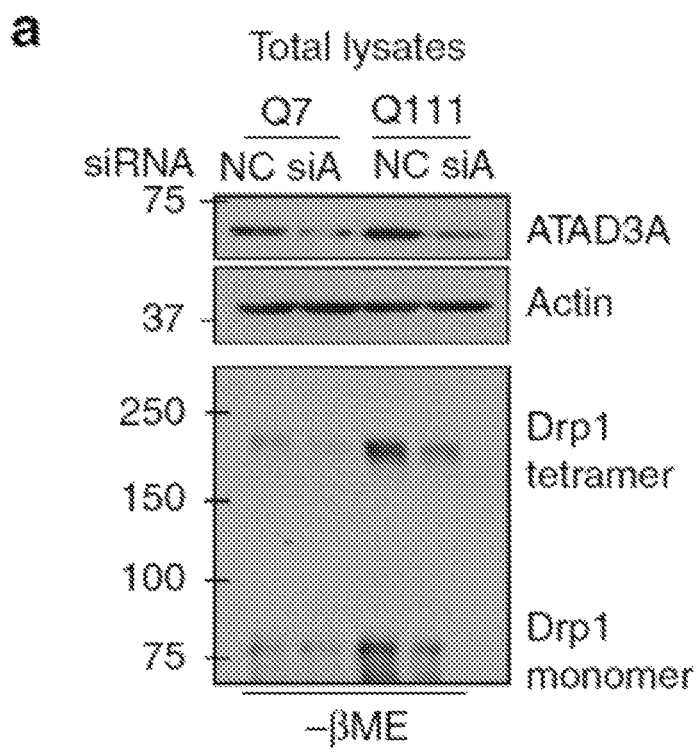
FIGS. 3(A-H) illustrates immunoblots, graphs, and images showing ATAD3A oligomerization impairs mitochondrial fission and mtDNA stability. HdhQ7 and Q111 cells were transfected with control siRNA (NC) or ATAD3A siRNA (siA) for 3 days. (A) Downregulation of ATAD3A was validated by WB. Actin: a loading control. Drp1 polymerization was analyzed by WB with anti-Drp1 antibodies in the absence of β-ME. (B) Mitochondria were isolated from HD striatal cells (Upper) and cells exposed to 5 mM 3-NP for 4 h (Lower). Drp1 mitochondrial level was analyzed by WB. Mitochondrial loading control: VDAC. (C) HeLa cells were transfected with ATAD3A-GFP truncated mutants for 48 h. Cells were stained with anti-Tom20 and anti-DNA antibodies. The co-localization of DNA and Tom20 was analyzed by confocal microscopy. Insert: the enlarged images. Scale bar: 10 µm. (D) The number of nucleoids immunopositive for both anti-DNA and anti-Tom20 was quantitated by NIH Image J software. 40-50 cells per group were analyzed. Three independent experiments, one-way ANOVA with Tukey's post-hoc test. (E) Neuro2A cells were transfected with ATAD3A-Flag WT or mutants for 48 h, and total DNA was extracted for qPCR analysis to monitor the mtDNA lesion. Upper: Representative DNA agarose gel of the amplification of the 10 kb mtDNA fragment. Lower: The quantification of mtDNA lesion. Four independent experiments, one-way ANOVA with Tukey's post-hoc test. (F) mtDNA content was analyzed by qPCR using primers from D-loop (left). TFAM mRNA level was analyzed by qPCR (right). At least 3 independent experiments, one-way ANOVA with Tukey's post-hoc test. (G) Left: Cells were stained with mitoSOX fluorescent probe to evaluate mitochondrial superoxide production (mitoROS). Right: Cell death rate was measured by LDH release into cytosol. Four independent experiments, one-way ANOVA with Tukey's post-hoc test. (H) The binding of TFAM and biotinylated mtDNA LSP probe was determined by biotin-streptavidin pull down in HD striatal cells transfected with ATAD3A siRNA (left) and in Neuo2A cells expressing ATAD3A truncated mutants (right). All shown representative blots are from at least 3 independent experiments. All data are mean±SEM.
Figure 3B:
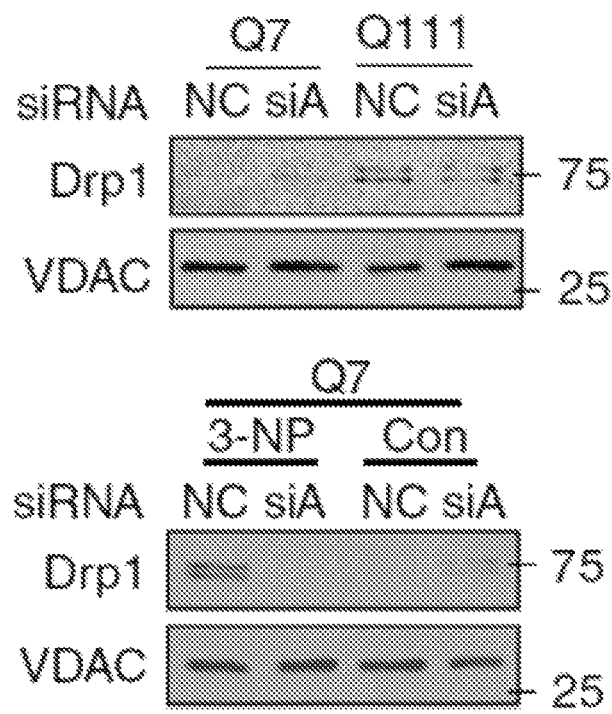
Figure 3D:
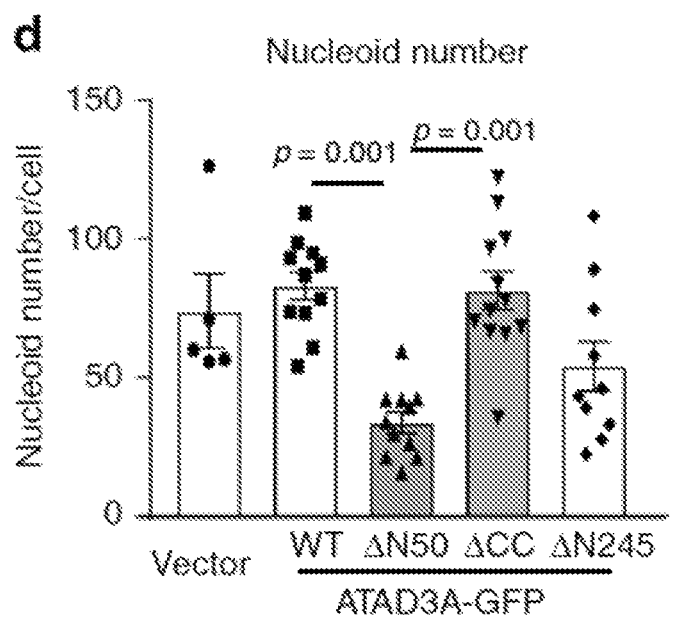

Expression of ATAD3A ΔN50 mutant induced Drp1 translocation to the mitochondria and Drp1 polymerization, two indicators of Drp1 fission activity. In contrast, expression of ATAD3A ΔCC mutant abolished these events. Conversely, knockdown of ATAD3A by RNA interference (siRNA) in HdhQ111 cells or 3-NP-treated wildtype cells reduced Drp1 polymerization (FIG. 3A) and Drp1 translocation to the mitochondria (FIG. 3B). ATAD3A silencing had no observable effect on other components of mitochondrial dynamics, including Mff, OPA1 and Mfn1.

A mutation occurring in the ATPase domain of ATAD3A (ATAD3A K358E) has been shown to induce Drp1-mediated mitochondrial fragmentation. However, expression of the K358E mutant in ATAD3A ΔN50 (ΔN50 K358E) had no additional effect on Drp1 translocation to the mitochondria when compared to that in cells expressing ATAD3A ΔN50, suggesting that the CC domain is required to recruit Drp1 to the mitochondria. Consistent with a previous study, HeLa cells expressing ATAD3A ΔN50 showed mitochondrial fragmentation, whereas both ATAD3A ΔCC expressing and ATAD3A ΔN245-expressing cells exhibited elongated and interconnected mitochondria. Neither overexpression of Drp1 nor knockout (KO) of Drp1 nor fission adaptors (Mff or Fis1) influences ATAD3A protein level. In fission adaptors Mff-KO, Mid49-KO, or Fis1-KO MEFs that exhibit elongated mitochondrial network, downregulating ATAD3A elicited mitochondrial fragmentation; the number of cells with fragmented mitochondria were significantly higher than those with control shRNA.

ATAD3A Oligomerization Impairs mtDNA Maintenance in HD

Figure 3C:
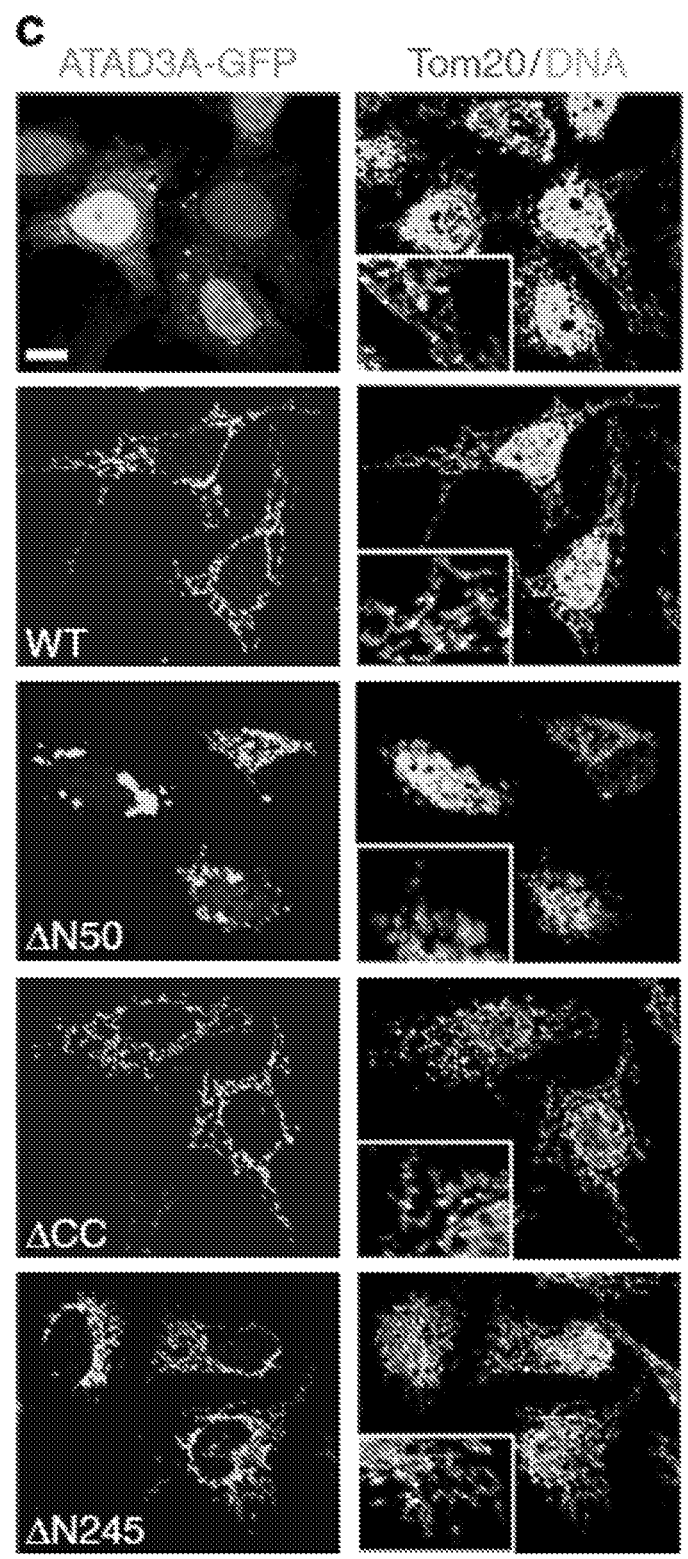
Figure 3E:
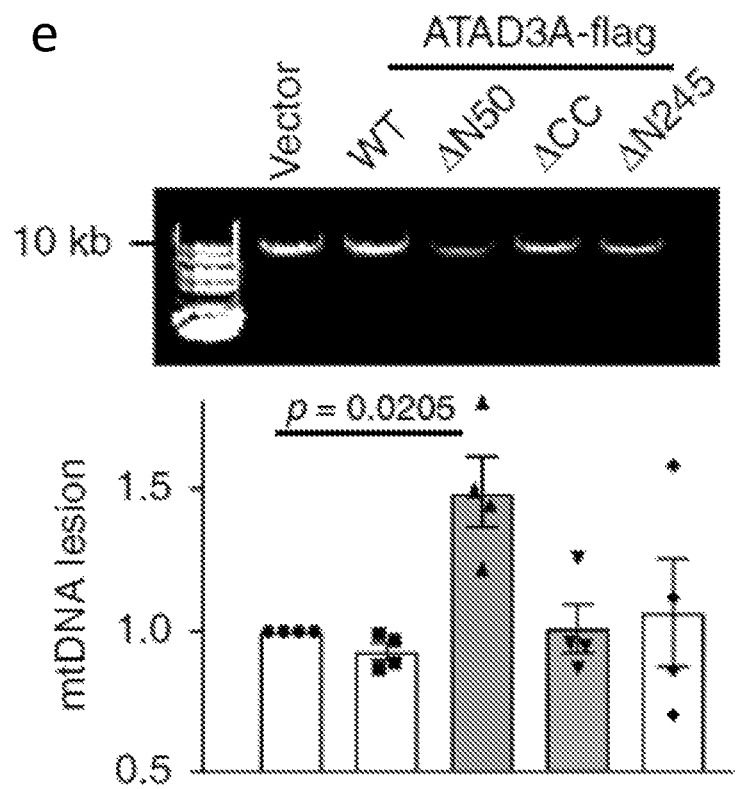
Figure 3F:
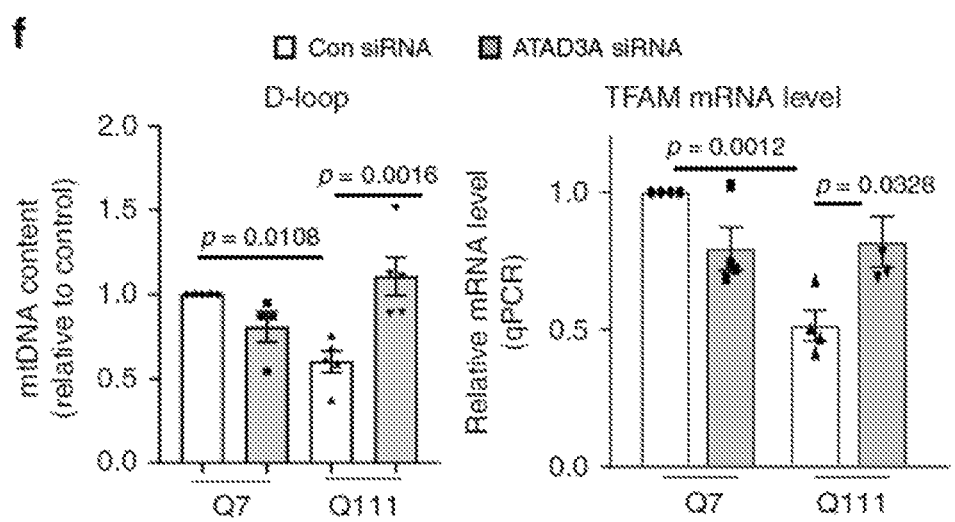
Figure 3G:
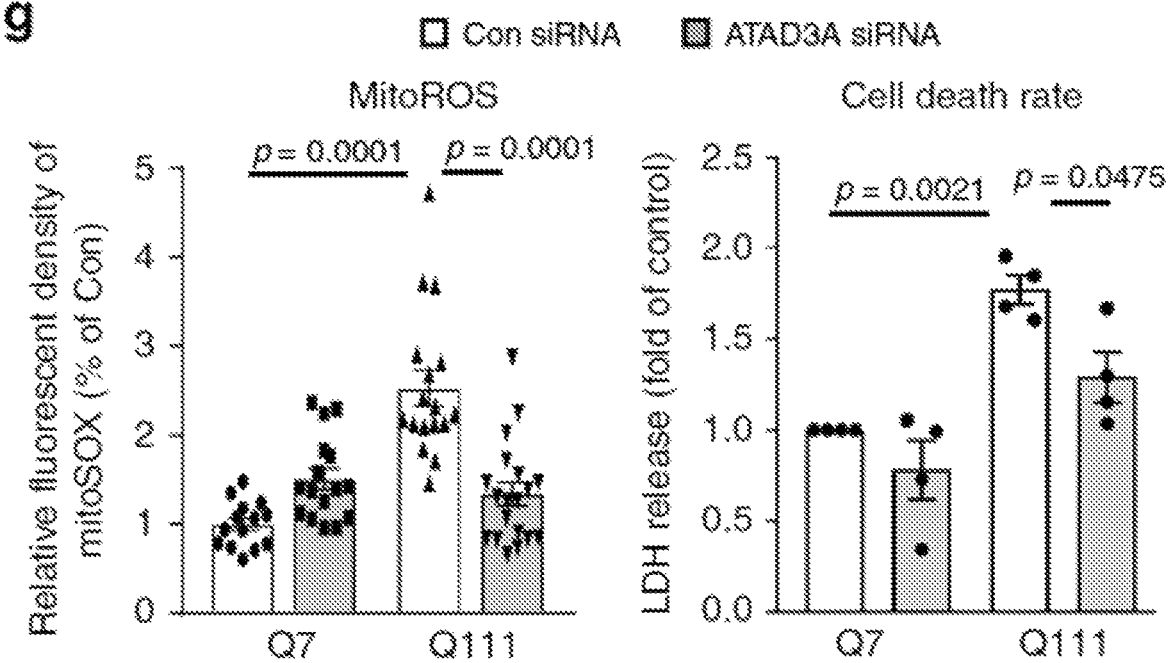
Figure 3H:
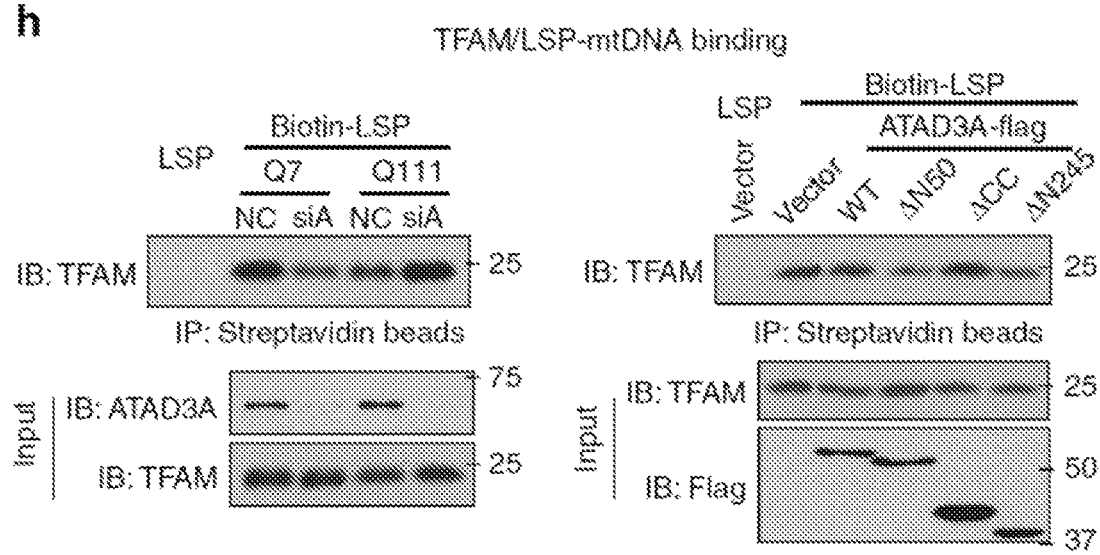

ATAD3A tightly maintains mtDNA nucleoids. Expression of ATAD3A ΔN50 mutant decreased the number of nucleoids immuno-positive for both anti-DNA and anti-Tom20 antibodies. In contrast, cells expressing ΔCC mutant exhibited a similar number of nucleoids as those in cells expressing control vector or ATAD3A WT (FIG. 3C, D). Expression of ΔN50 ATAD3A induced more than 50% lesion to mtDNA, which was not seen in cells expressing ΔCC mutant (FIG. 3E). HdhQ111 cells exhibited a decreased copy number of mtDNA and non-coding region of mitochondrial genome D-loop (FIG. 3F), which were corrected by ATAD3A silencing (FIGS. 3A, F). Down-regulation of ATAD3A was sufficient to diminish mitochondrial superoxide production and cell death in HdhQ111 cells (FIG. 3G). Consistent with previous studies, we observed decreased mtDNA abundance and nucleoid disorganization in Drp1 KO MEFs. The decrease of mtDNA content due to ATAD3A reduction was abolished in Drp1 KO MEF. In contrast, knockdown of ATAD3A reduced the number of mitochondrial nucleoids in fission adaptors Mff-KO, Mid49-KO, or Fis1-KO MEFs. Thus, among fission-related proteins, ATAD3A and Drp1 may form a complex to uniquely maintain mtDNA stability.

mtDNA maintenance, replication, and transcription are controlled by mitochondrial nucleoid, which is composed of a set of mtDNA-binding proteins, including TFAM (the transcription factor A, mitochondrial), SSBP1 (the mitochondrial single strand binding protein), Twinkle (the mtDNA helicase), POLG and POLRMT (the mtDNA polymerases). By qPCR, we showed a significant decrease of TFAM mRNA in HdhQ111 cells, which was corrected by ATAD3A knockdown (FIG. 3F). ATAD3A silencing had no effect on POLG, POLRMT, Twinkle, or SSBP1. TFAM specifically binds the light strand promoter (LSP) within the Dloop region of mtDNA, the interaction of which is necessary to activate bidirectional mtDNA transcription. Expression of ATAD3A ΔN50 mutant decreased the binding of TFAM and biotinylated mtDNA LSP probe compared to that in cells expressing ATAD3A WT or ΔCC mutant (FIG. 3H-right), suggesting that ATAD3A oligomerization impairs TFAM mediated mtDNA packaging. In HdhQ111 cells, the binding of endogenous TFAM to mtDNA LSP was greatly decreased, which was reversed by knockdown of ATAD3A (FIG. 3H-left). Thus, enhancing dimerization of ATAD3A in HD not only resulted in Drp1 activation but also led to mtDNA instability and damage by disrupting TFAM/mtDNA binding. Downregulation of ATAD3A in HdhQ7 cells reduced the binding between TFAM and LSP and slightly decreased mtDNA content and TFAM gene expression when compared to that in HdhQ7 cells expressing control siRNA (FIG. 3F), which is consistent with an important role of ATAD3A steady state in mtDNA nucleoid maintenance.

ATAD3A Deacetylation Promotes its Dimerization

Figure 4A:
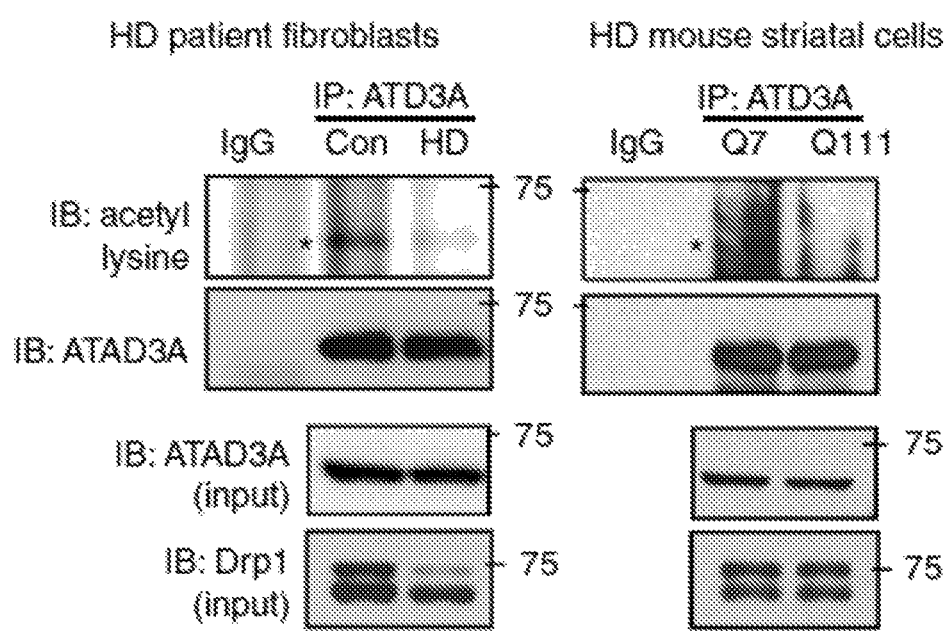
FIGS. 4(A-H) illustrate immunoblots, images, and graphs showing ATAD3A deacetylation. (A) Total cell lysates of HdhQ7 and HdhQ111 cells or fibroblasts of HD patient and control subjects were subject to IP with anti-ATAD3A antibodies followed by WB with anti-acetyl lysine antibodies. Asterisks (*) indicates the acetylated ATAD3A. (B) ATAD3A K135 in peptide 130-AQYADLLAR-138 in human (K134 in mouse) was identified as an acetylated site. The K135 is present on the surface of ATAD3A N-terminus simulated structure. HEK293 cells were transfected with the indicated Flag-tagged K135 mutants or ATAD3A WT for 48 h. (C) ATAD3A dimers were analyzed by WB in the presence or absence of β-ME. Histogram: the quantification of relative density of ATAD3A dimer in the absence of β-ME versus total protein level under reduced conditions. At least 6 independent experiments, one-way ANOVA with Tukey's post-hoc test. (D) Immunoprecipiates with anti-Flag antibodies were analyzed with anti-Myc antibodies. Histogram: the quantification of relative density of Myc-ATAD3A/ATAD3A-Flag in the immunoprecipitates. Five independent experiments, one-way ANOVA with Tukey's post-hoc test. (E) IP of total protein lysates was performed with the indicated antibodies. (F) HeLa cells were transfected with Flag-ATAD3A WT or K mutants for 48 h. Cells were stained with anti-Tom20 and anti-Flag antibodies. Mitochondrial morphology was imaged. Scale bar: 10 µm. Histogram: the percentage of cells with fragmented mitochondria to total number of cells. Three independent experiments, one-way ANOVA with Tukey's post-hoc test. (G) The binding of TFAM and biotinylated mtDNA LSP probe was determined by biotin-streptavidin pull down. Histogram: the relative density of TFAM in the Biotin-LSP precipitates. Three independent experiments, one-way ANOVA with Tukey's post-hoc test. (H) HeLa cells were stained with anti-Tom20 and anti-DNA antibodies at the indicated groups. The co-localization of DNA and Tom20 was analyzed by confocal microscopy. Insert: the enlarged images. Scale bar: 10 µm.
Figure 4B:
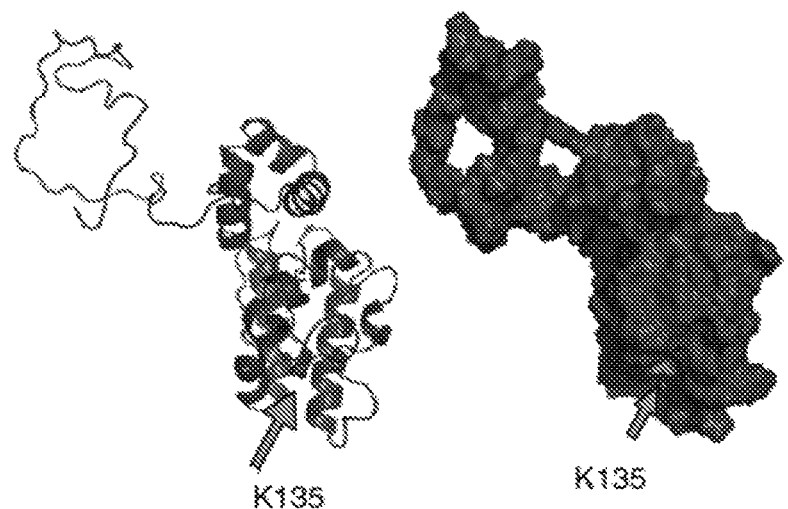

To examine the mechanism by which ATAD3A forms dimers in HD, we analyzed ATAD3A acetylation, a posttranslational modification that regulates oligomerization of a variety of proteins. ATAD3A was basally acetylated in wildtype HdhQ7 cells and control human fibroblasts, whereas the level of ATAD3A acetylation was greatly reduced in both HdhQ111 cells and HD patient fibroblasts (FIG. 4A), suggestive of a deacetylation. To identify acetylated lysines on ATAD3A, we extracted total cell lysates of HdhQ7 and HdhQ111 cells and immunoprecipitated with anti-ATAD3A antibodies followed by LC-MS/MS analysis. When we focused on the N-terminus of ATAD3A, which mediates dimerization, the interaction with Drp1, and the stability of mitochondrial nucleoids (FIG. 3), we identified K134 on the peptide 129-AQYQDKLAR-137 (SEQ ID NO: 18) in mice (K135 in human) to be acetylated in HdhQ7 cells. The lysine 134 residue, conserved among species, resides in the linker between CC1 and CC2 domain and is present on the surface of ATAD3A simulated structure (FIG. 4B), which renders it accessible for reversible acetylation. No phosphorylated site within N-terminus of ATAD3A was identified by the mass spectrometry we used in both HdhQ7 and HdhQ111 cells. Although computation analysis predicts serine 48 as a putative phosphorylated site, mutation (replace serine to either alanine or aspartate) in two conserved serine sites (serine 2 and 48) of ATAD3A had no effects on ATAD3A dimerization. These data thus led us to determine acetylation as a functionally posttranslational modification of ATAD3A.

Figure 4C:
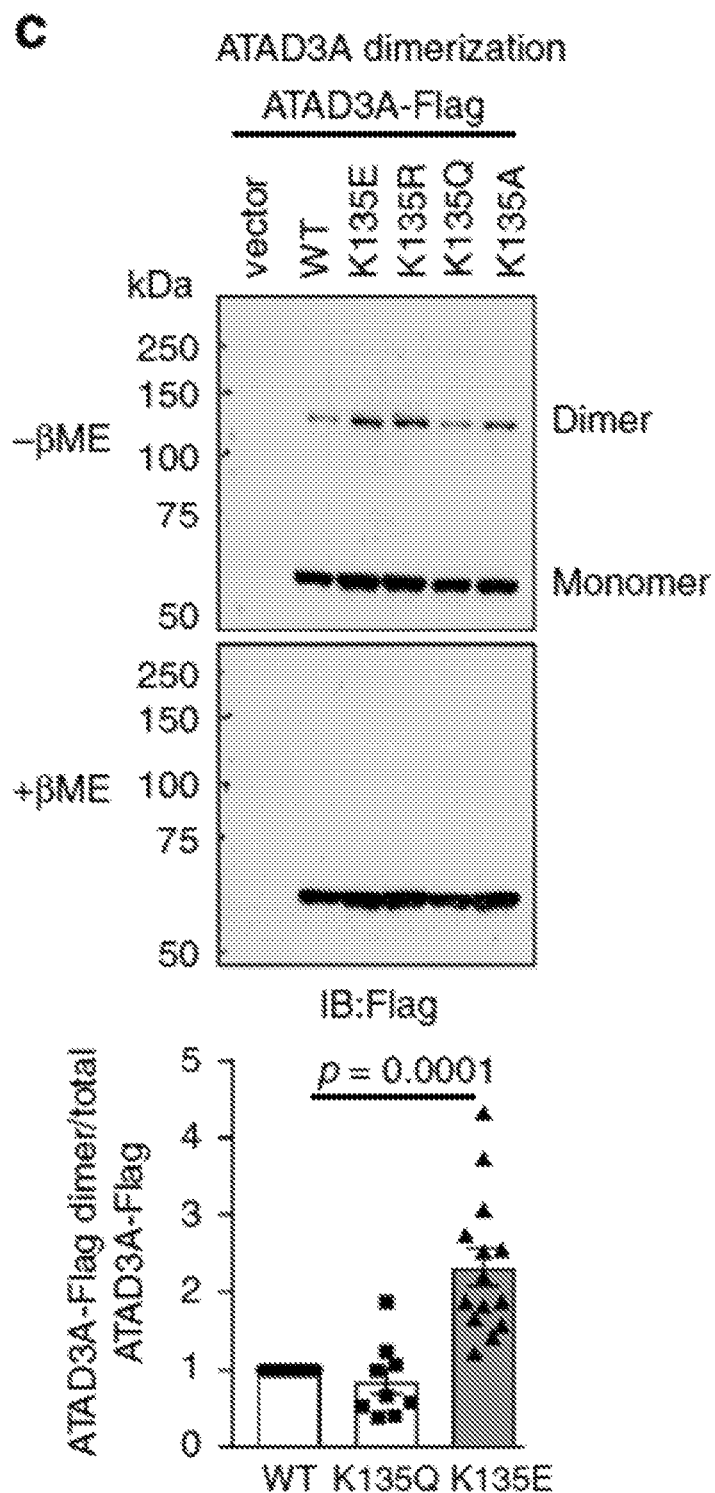
Figure 4D:
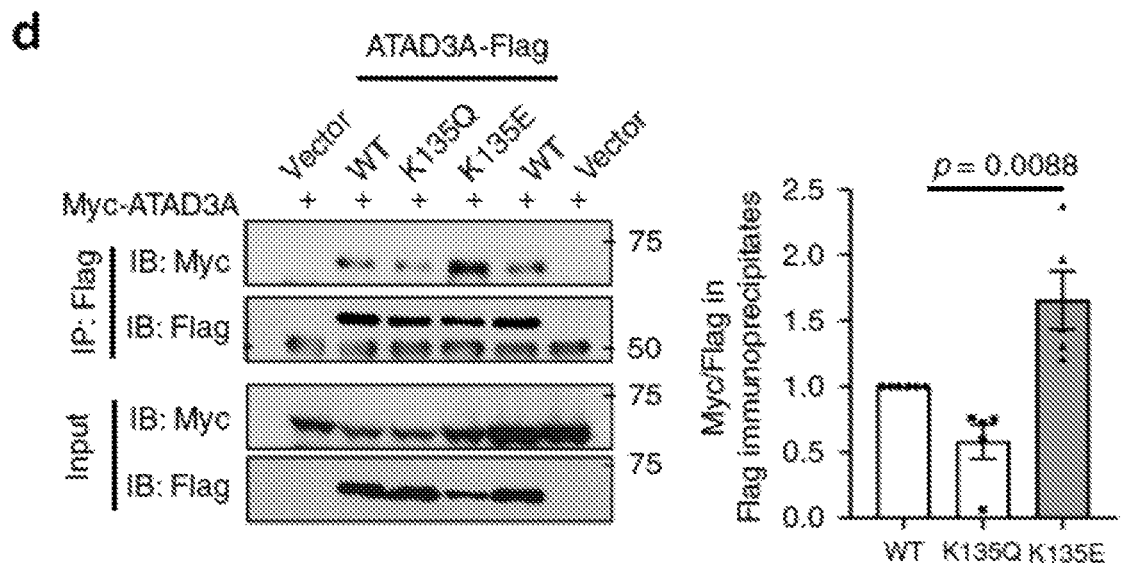

To assess whether K135 is important for regulation of ATAD3A dimerization, we replaced K135 with glutamine (K135Q) or Alanine (K135A), which neutralizes the positive charge and mimics the acetylated state. We also used mutant K135E (replaced lysine with glutamic acid) or K135R (replaced lysine with arginine) to mimic deacetylated ATAD3A. The K135E and K135Q mutants were mainly used in our studies. We transfected ATAD3A WT or K mutants into HEK293 cells. Expression of acetyl-deficient K135E or K135R mutant enhanced ATAD3A ability to dimerize; the level of dimer was significantly higher than that in ATAD3A-WT expressing cells (FIG. 4C). While the levels of ATAD3A dimer were comparable between ATAD3A-WT-expressing and ATAD3A K135Q mutant-expressing cells (FIG. 4C), the K135Q mutant was restricted in its ability to form heterodimer with ATAD3A-WT. In contrast, K135E mutant more efficiently bound to ATAD3A WT to form dimer (FIG. 4D). Thus, dimerization of ATAD3A is promoted by deacetylation of ATAD3A at K135 site.

Figure 4E:
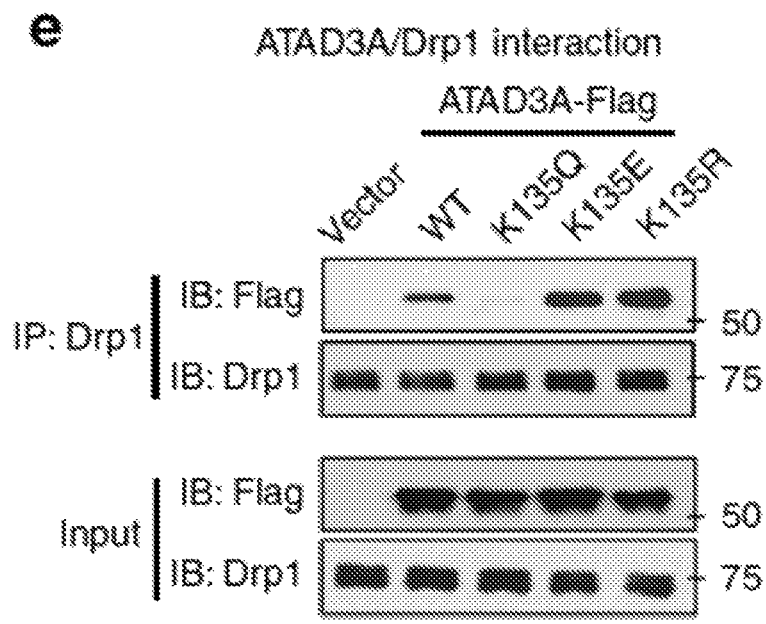
Figure 4F:
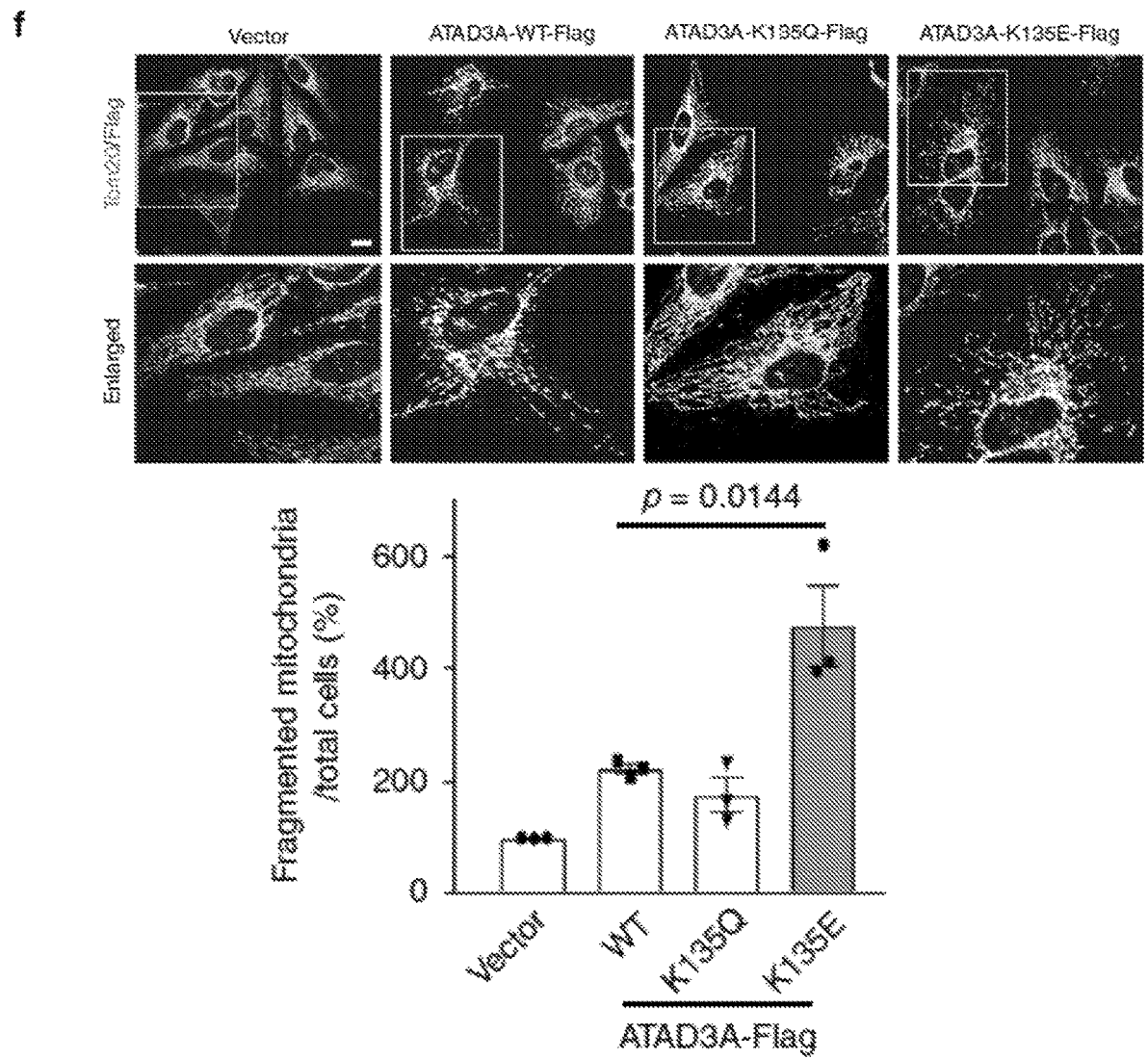
Figure 4G:
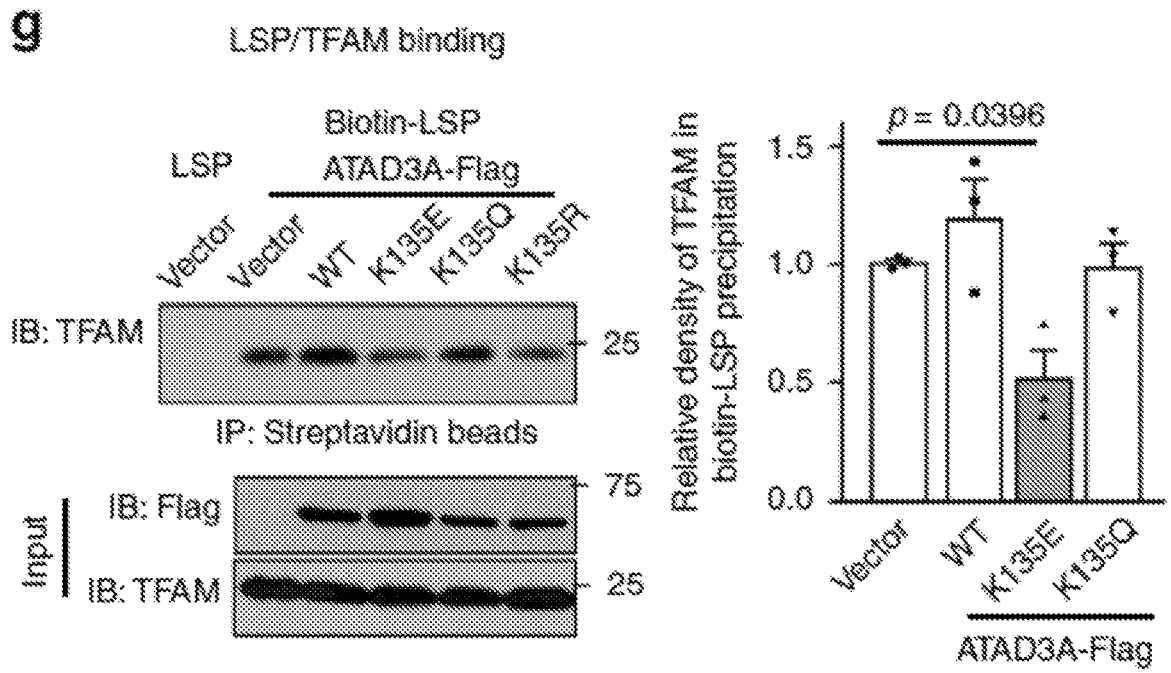
Figure 4H:
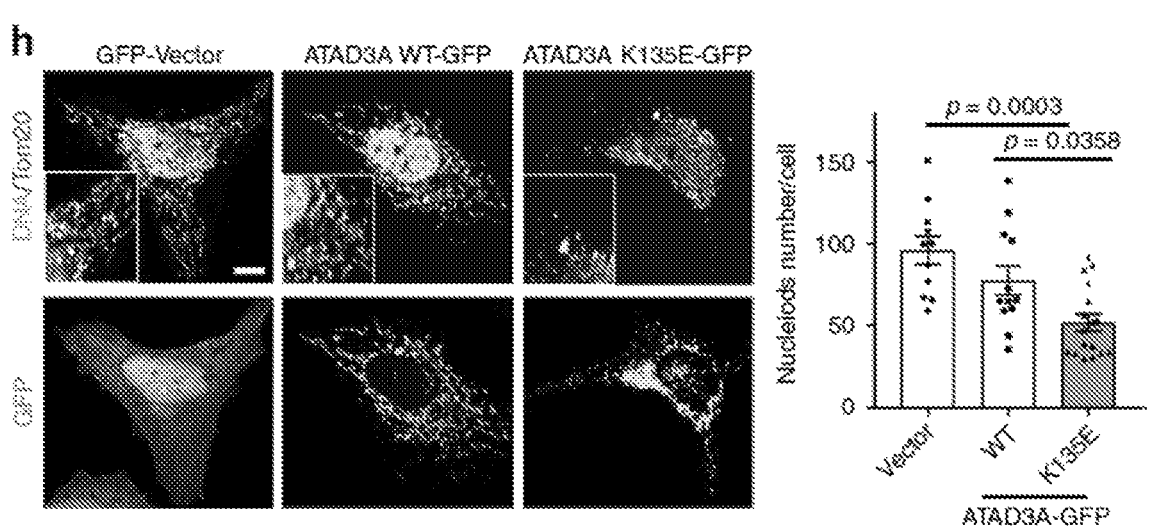

We found that the acetyl-deficient mutant K135E or K135R bound to Drp1 to a greater extent than ATAD3A WT, whereas the acetyl-mimetic ATAD3A K135Q mutant lost the capacity to bind to Drp1 (FIG. 4E). HeLa cells expressing ATAD3A K135E mutant exhibited extensive mitochondrial fragmentation relative to that in ATAD3A WT expressing cells (FIG. 4F). Moreover, expression of K135E or K135R mutant reduced the binding of mtDNA LSP to TFAM (FIG. 4G) and decreased the number of mitochondrial nucleoids (FIG. 4H), suggesting mtDNA lesion.

Peptide DA1 Blocks ATAD3A/Drp1 Binding in HD

Figure 5A:
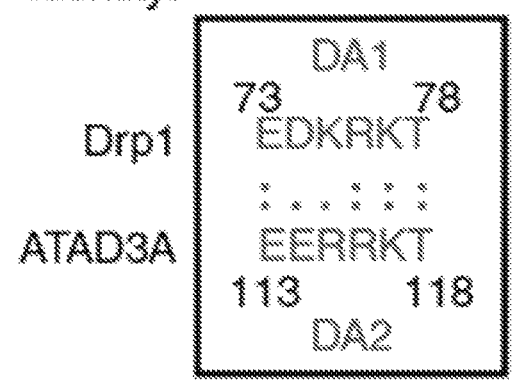
Figure 5B:
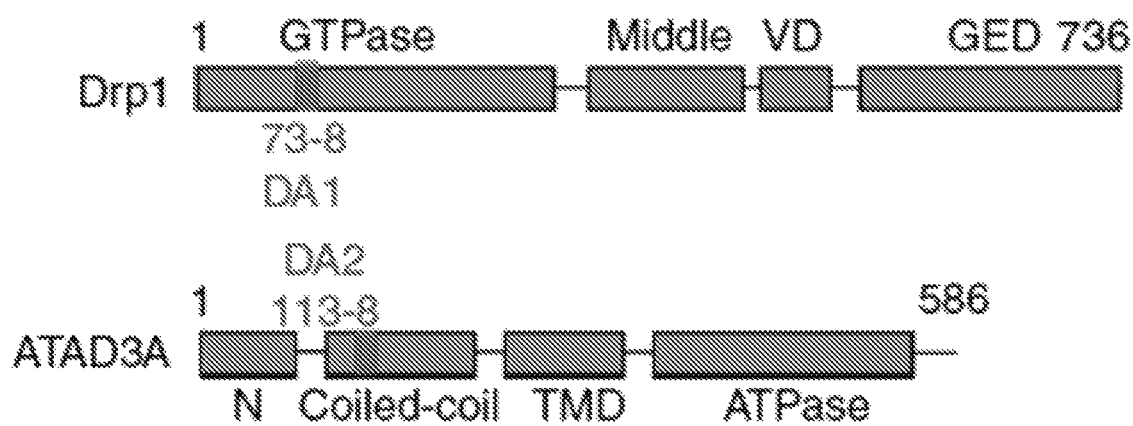
Figure 5C:
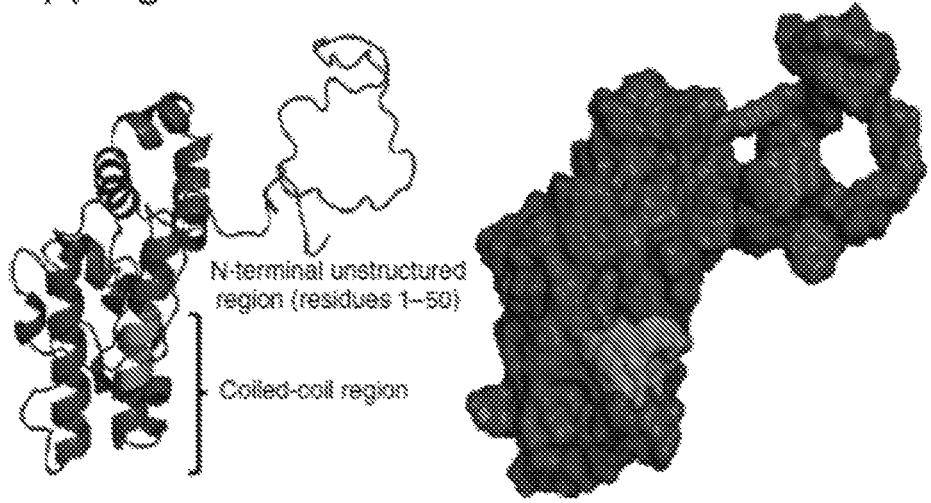
Figure 5D:
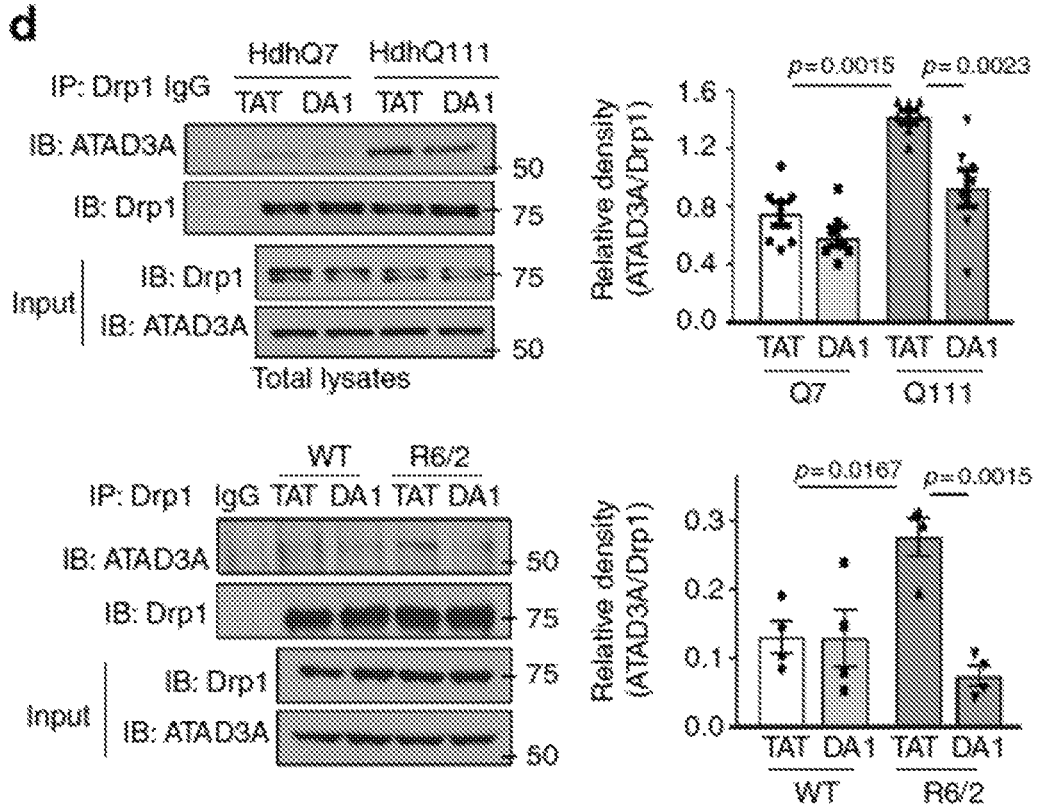
Figure 5E:
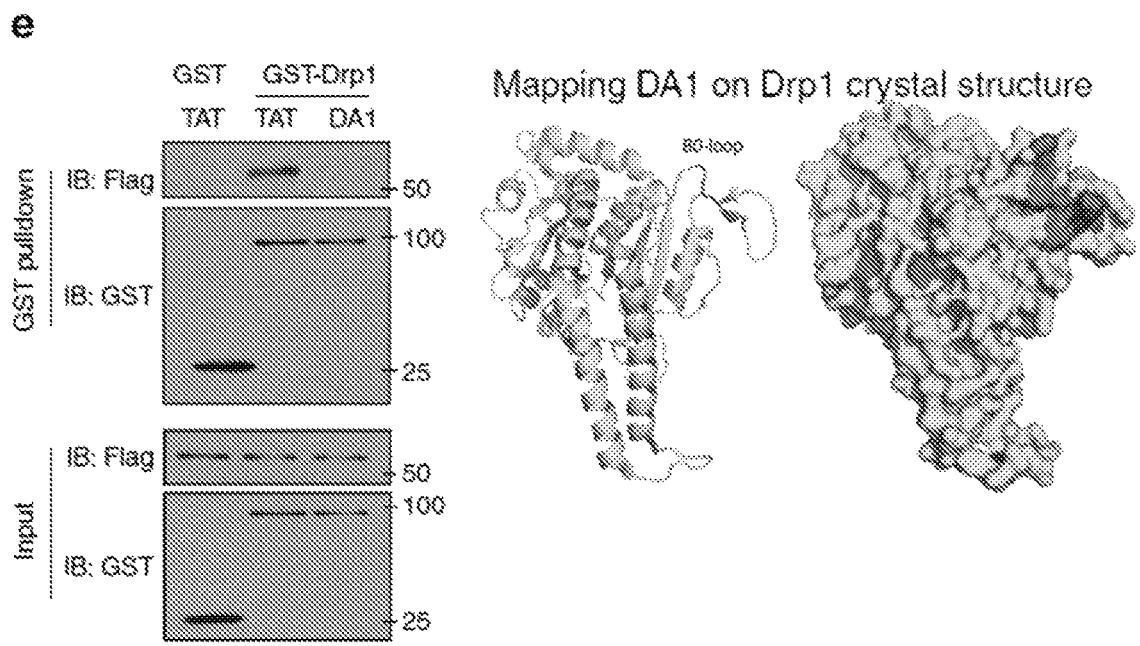

Next, we assessed the functional significance of enhanced Drp1/ATAD3A binding in HD pathology. We previously demonstrated that short peptides interfering with specific protein-protein interactions can serve as pharmacological inhibitors to identify the role of interacting proteins in the pathogenesis of human diseases. In a similar approach to the peptide designs for Drp1 peptide P110 or VCP peptide HV-3-, we used L-ALIGN sequence alignment software and identified one region of homology between Drp1 (human, NP_036192) and ATAD3A (human, NP_001164006) (FIG. 5A). The two regions were marked as region DA1 and DA2. Consistent with our domain mapping of Drp1-ATAD3A interaction, the regions of homology are only located in the CC domain of ATAD3A and GTPase domain of Drp1 (FIG. 5B). The two regions, present on the surface of Drp1 and ATAD3A (FIG. 5C), are likely available for protein-protein interactions.

Figure 9A:
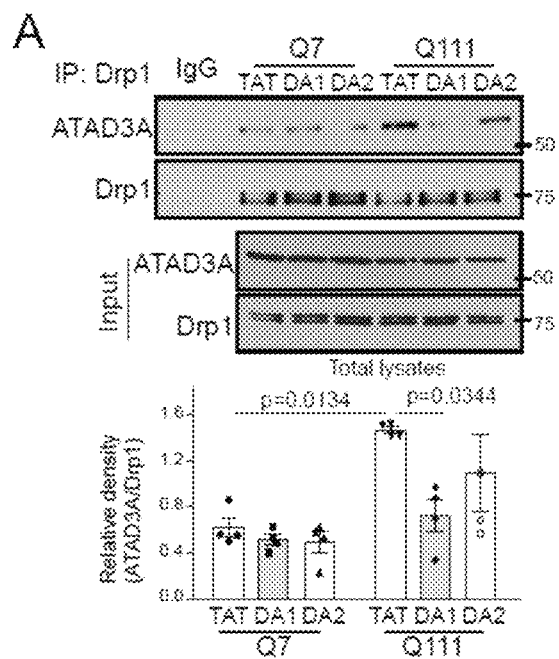
Figure 9B:
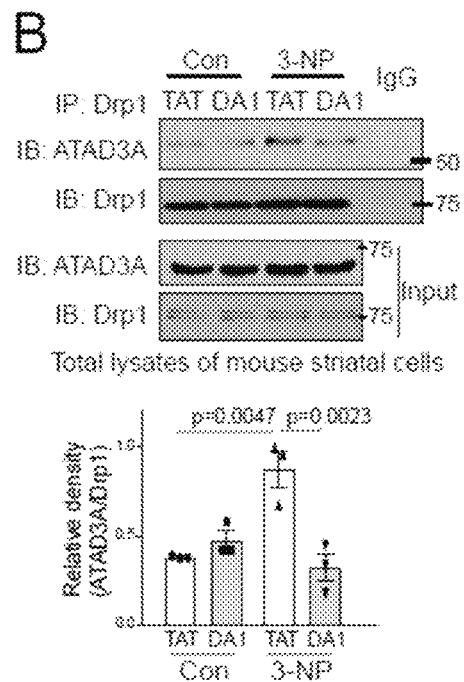
Figure 9D:
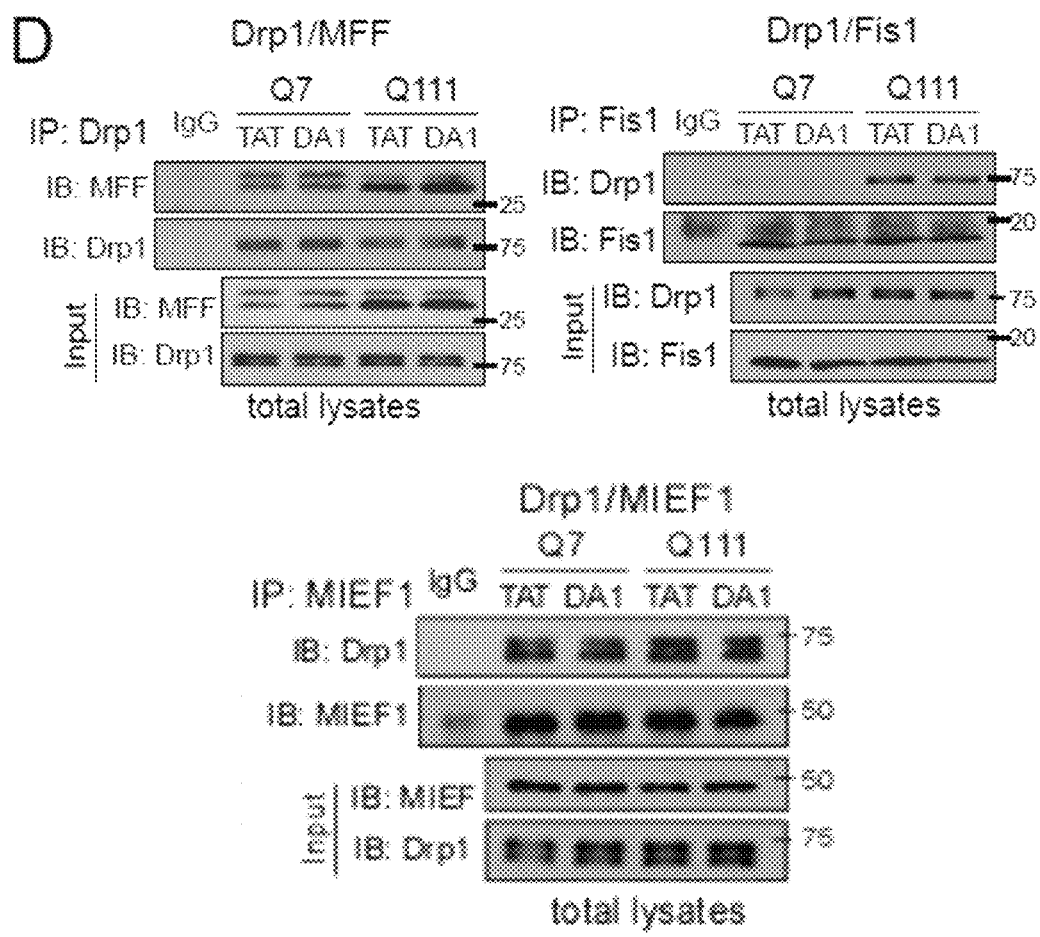

We synthesized peptides corresponding to the homologous regions between Drp1 and ATAD3A (FIG. 5A), and conjugated them to the cell permeating TAT protein-derived peptide, $TAT_{47-57}$, in order to enable in vivo delivery. These peptides are referred to as DA1 and DA2. DA1 treatment significantly reduced the binding of Drp1/ATAD3A in HdhQ111 cells (FIG. 5D and FIG. 9A), in striatal cells exposed to 3-NP and in striatal extracts of HD R6/2 mice (FIG. 5D), whereas DA2 showed a trend toward inhibition of the interaction (FIG. 9A). Notably, the presence of DA1 abolished the binding of GST-Drp1 and ATAD3A-Flag in vitro (FIG. 5E), indicating a direct inhibition. Peptide DA1 is derived from the loop region of Drp1 GTPase domain, which is critical for protein-protein interaction, and corresponds to a sequence in the first CC domain of ATAD3A (FIG. 5B). The sequence of DA1 in Drp1 is highly conserved among species (FIG. 9C). Treatment with DA1 did not influence the interactions of Drp1 with its mitochondrial adaptors Mff, Fis1 and MIEF1 in HdhQ111 cells (FIG. 9D), suggesting a selectivity.

Figure 5F:
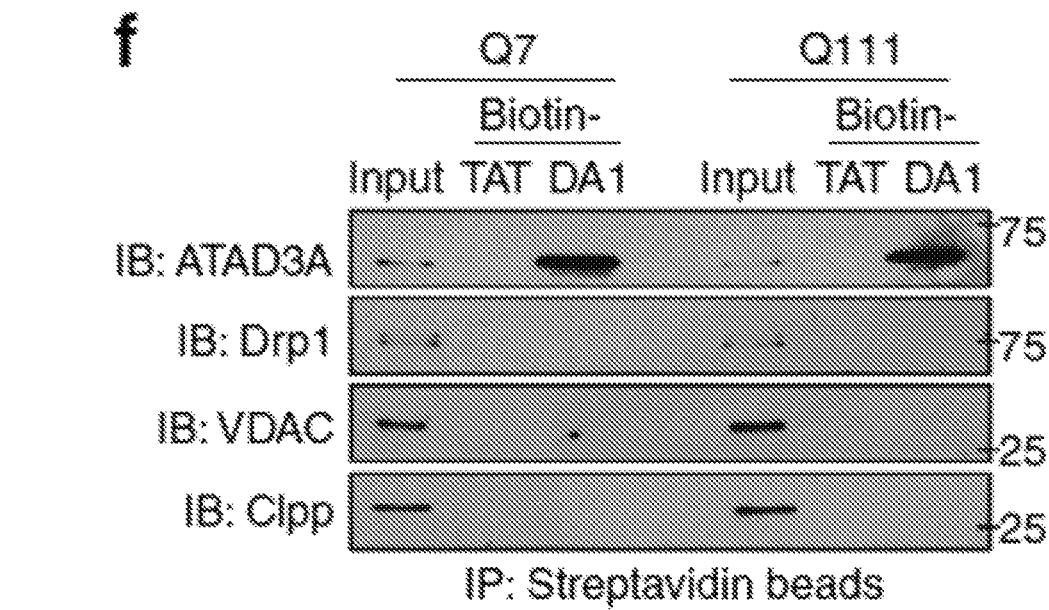
Figure 5G:
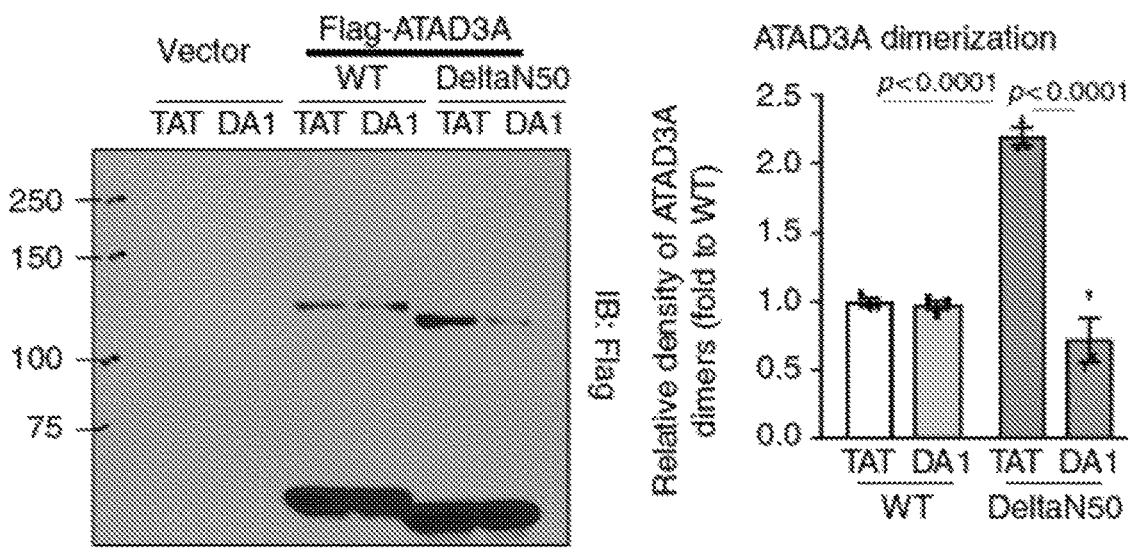
Figure 5H:
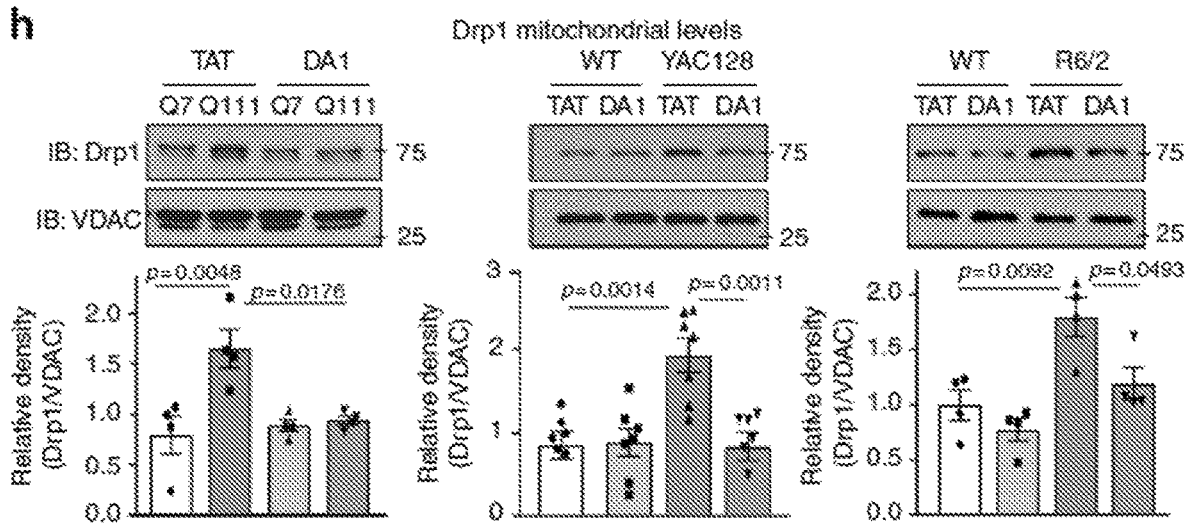
Figure 5I:
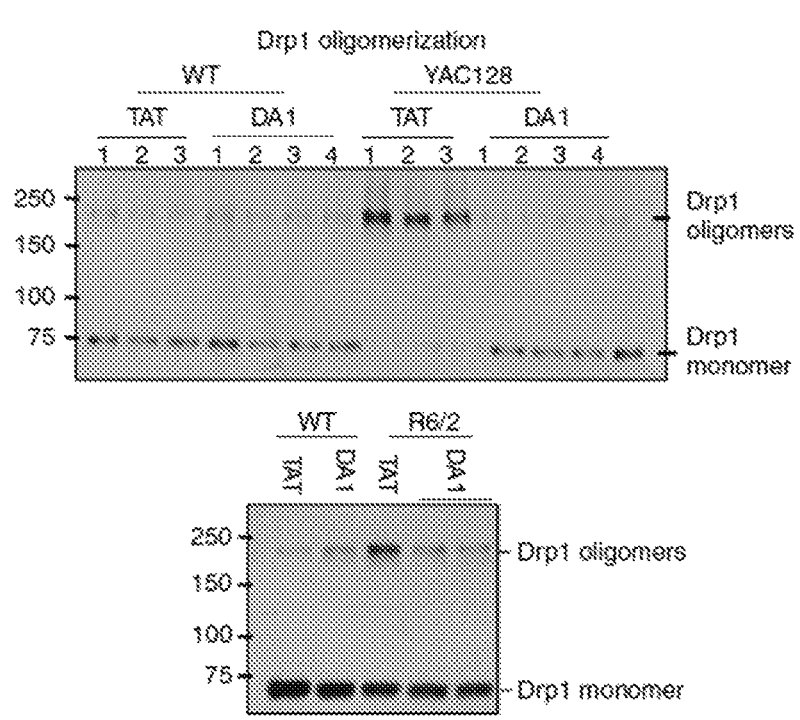
Figure 5J:
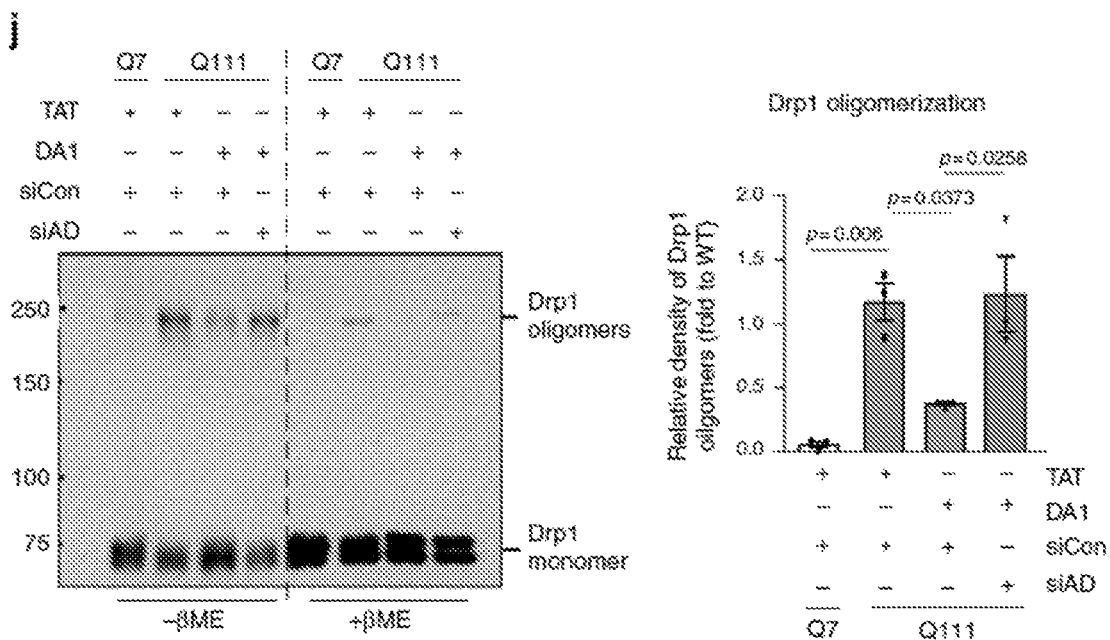
Figure 9E:
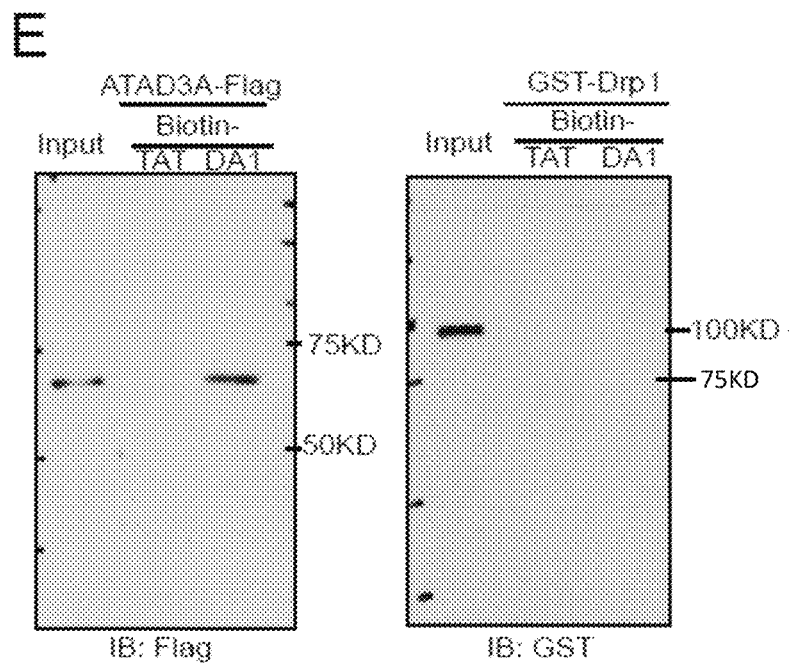
Figure 9F:
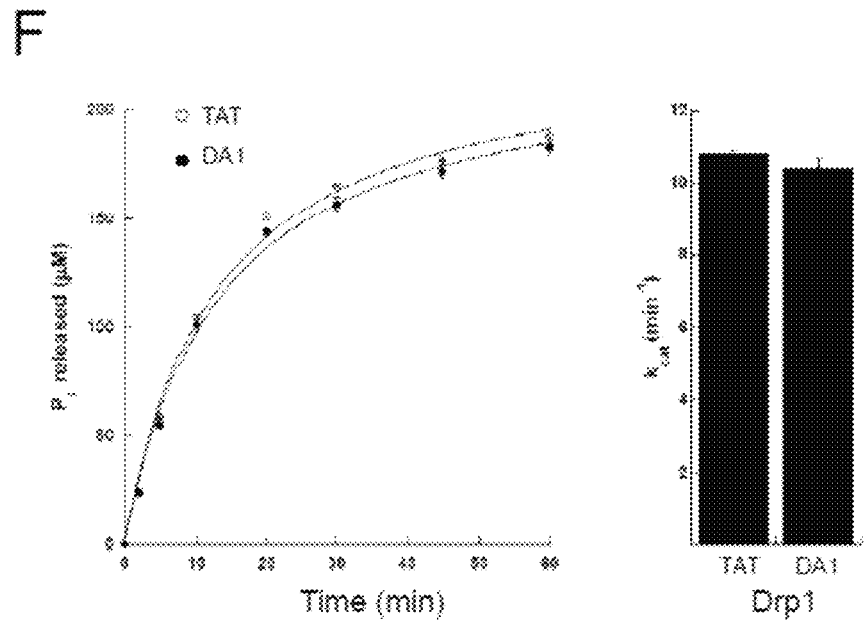
Figure 9G:
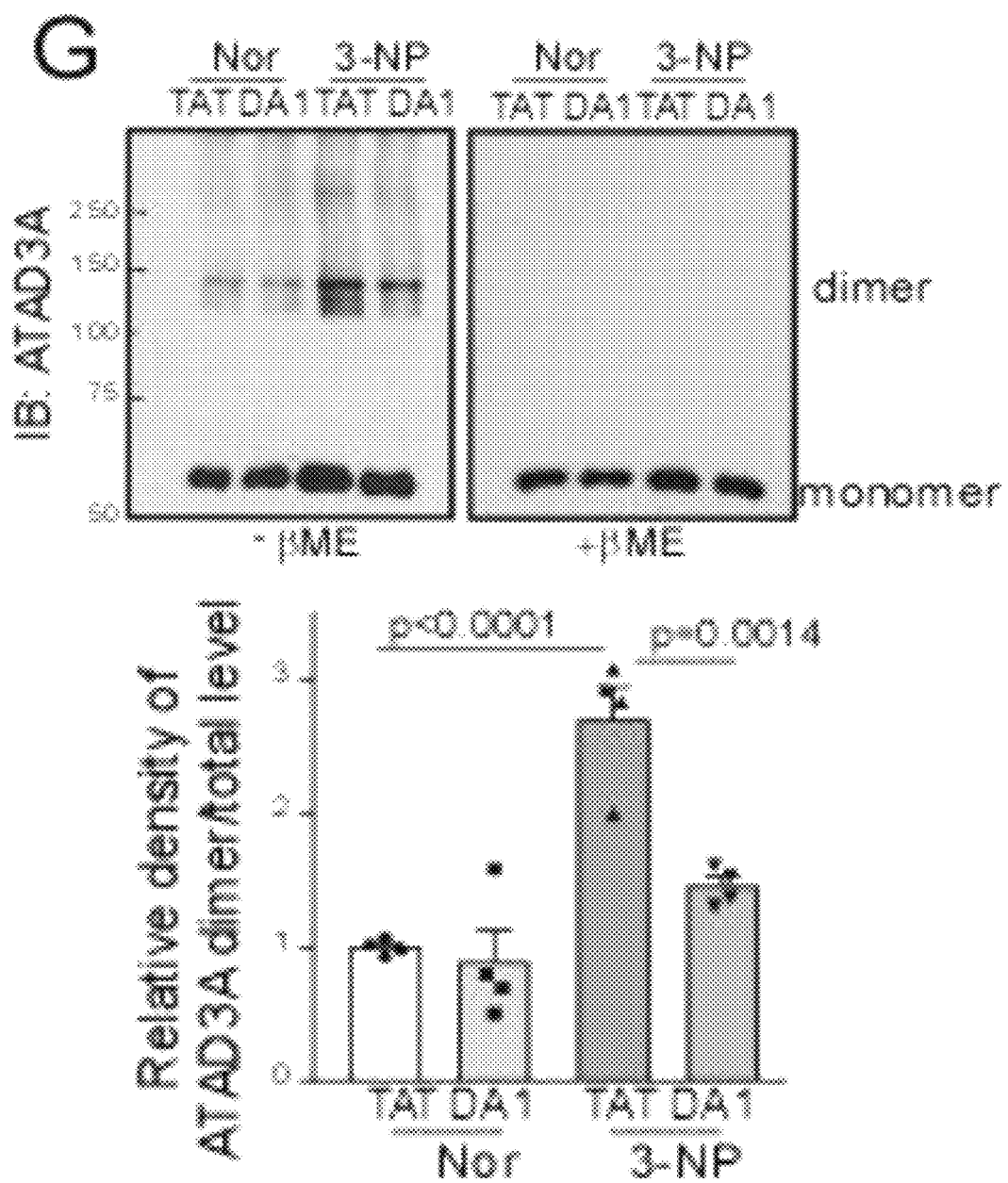
Figure 9H:
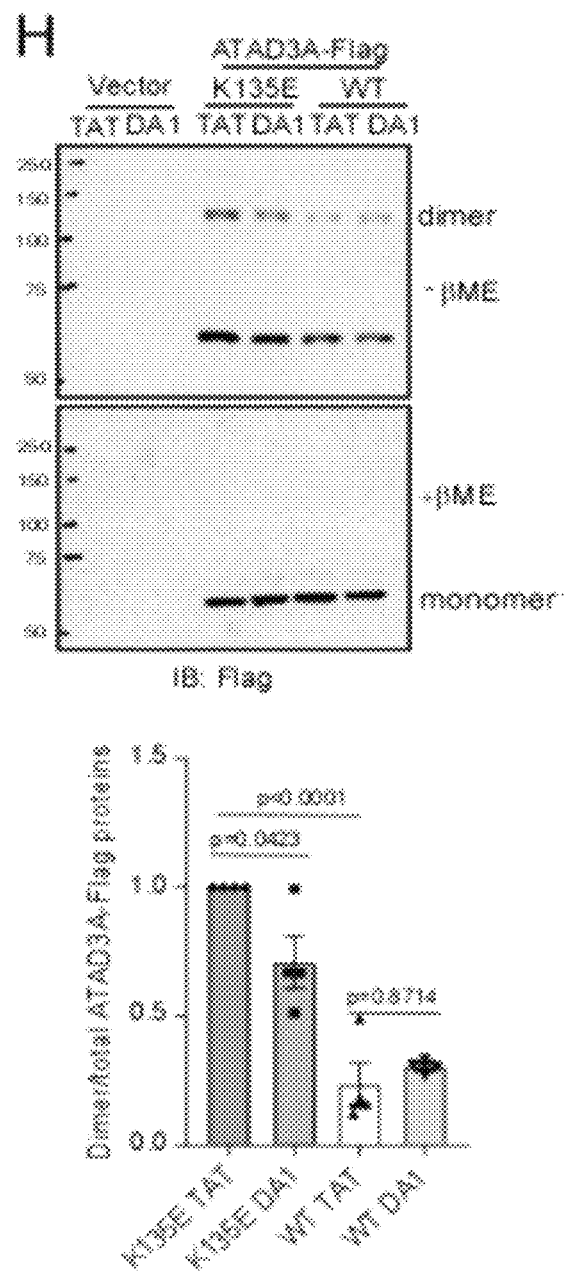
Figure 9I:
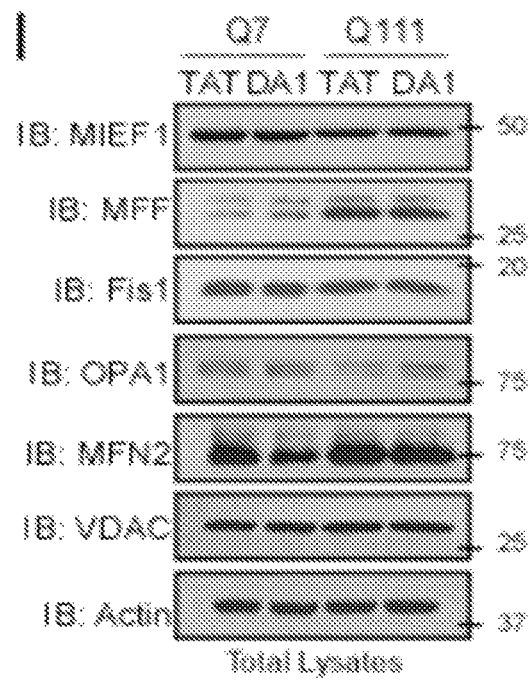

To examine the specificity of DA1, we incubated biotin-conjugated DA1 or TAT with total protein lysates of HD striatal cells followed by IP with streptavidin beads. Biotin-DA1 pulled down endogenous ATAD3A and not Drp1 (FIG. 5F). No detectable binding was observed between biotin-DA1 and the mitochondrial matrix protein ClpP or the OMM protein VDAC (FIG. 5F). Moreover, biotin-DA1 bound to ATAD3A-Flag and not to GST-Drp1 recombinant protein in vitro (FIG. 9E). DA1 had no effects on Drp1 oligomerization-induced GTPase activity in vitro, excluding a direct role on Drp1 (FIG. 9F). These results suggest that DA1 competes with Drp1 to bind to ATAD3A, which in turn interferes with the interaction of Drp1/ATAD3A. Furthermore, DA1 treatment abolished the dimerization of ATAD3A in cells exposed to 3-NP (FIG. 9G), and in cells expressing ATAD3A ΔN50 mutant (FIG. 5G) or ATAD3A acetyl-deficient mutant K135E (FIG. 9H), whereas it had minor effect on ATAD3A dimerization in normal cells or in cells expressing ATAD3A wildtype. Thus, DA1 preferentially prevents ATAD3A oligomerization induced under stress or diseased conditions, rather than that in control cells. This is likely due to the lower level of ATAD3A oligomers under normal conditions or the steady state of the wildtype protein.

DA1 treatment abrogated Drp1 translocation to the mitochondria and Drp1 polymerization in HD mouse striatal cells and striatum of HD YAC128 and R6/2 mice (FIG. 5H, I), but it did not affect other mitochondrial fusion and fission-related proteins (FIG. 15I). The inhibitory effect of DA1 on Drp1 tetramer formation was abolished upon ATAD3A knockdown (FIG. 5J), indicating that DA1 requires the presence of ATAD3A to suppress Drp1 activation. Together, our results support the hypothesis that DA1 peptide blocks ATAD3A and Drp1 interaction in HD by directly binding to ATAD3A, which in turn suppresses ATAD3A dimerization and inhibits the activation of both Drp1 and ATAD3A.

DA1 Improves Mitochondrial Function in HD Cells

Figure 6A:
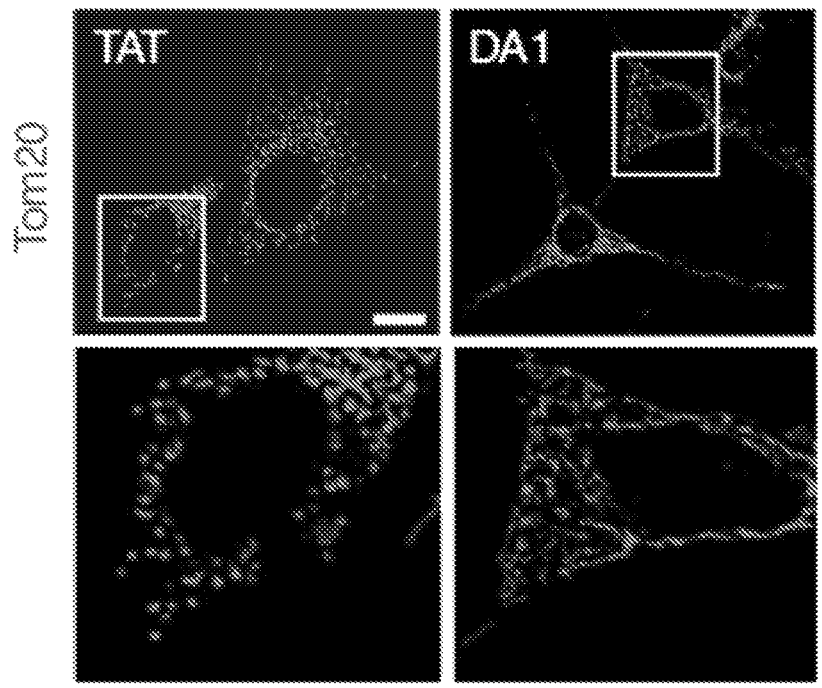
Figure 6A:
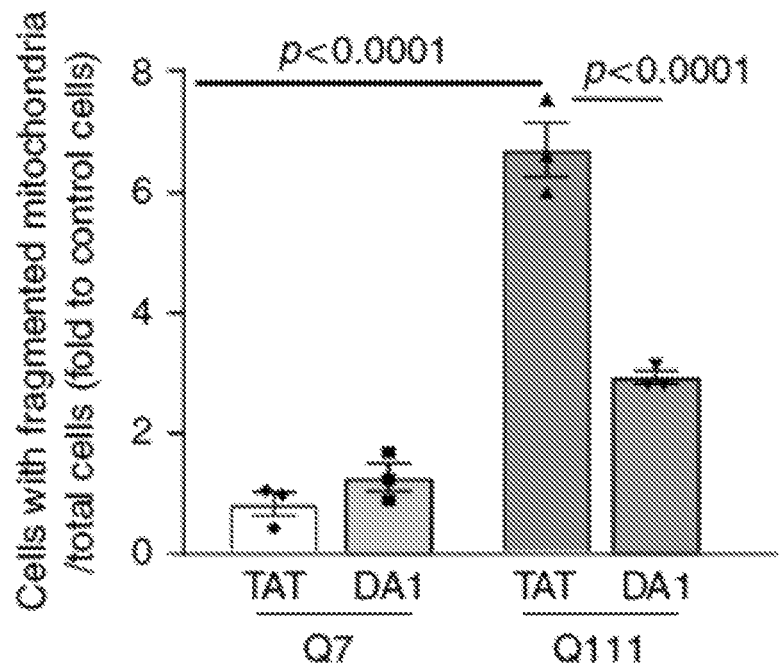
Figure 6B:
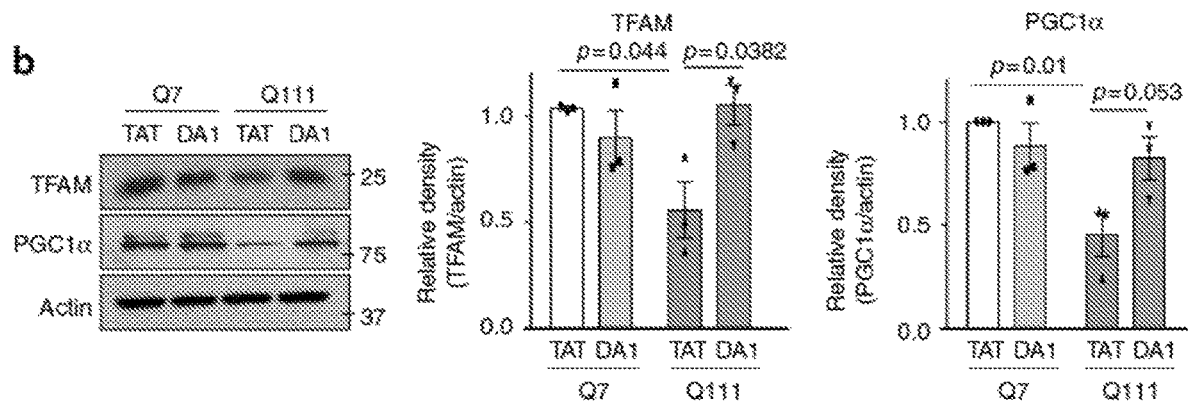
Figure 6C:
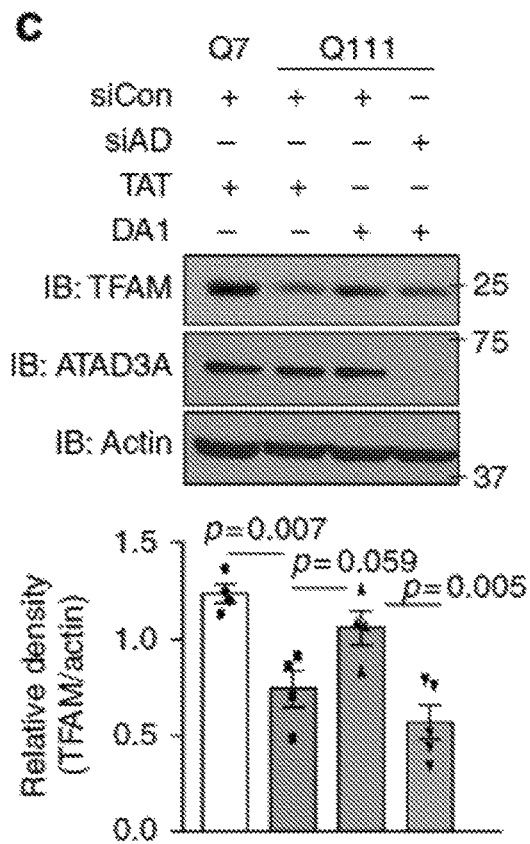
Figure 6D:
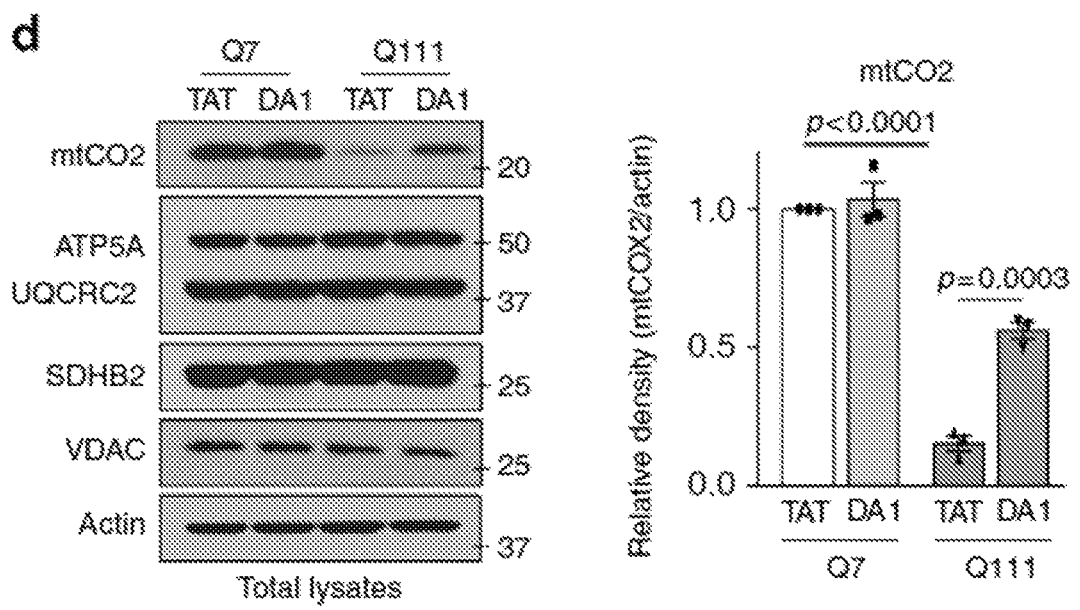
Figure 6E:
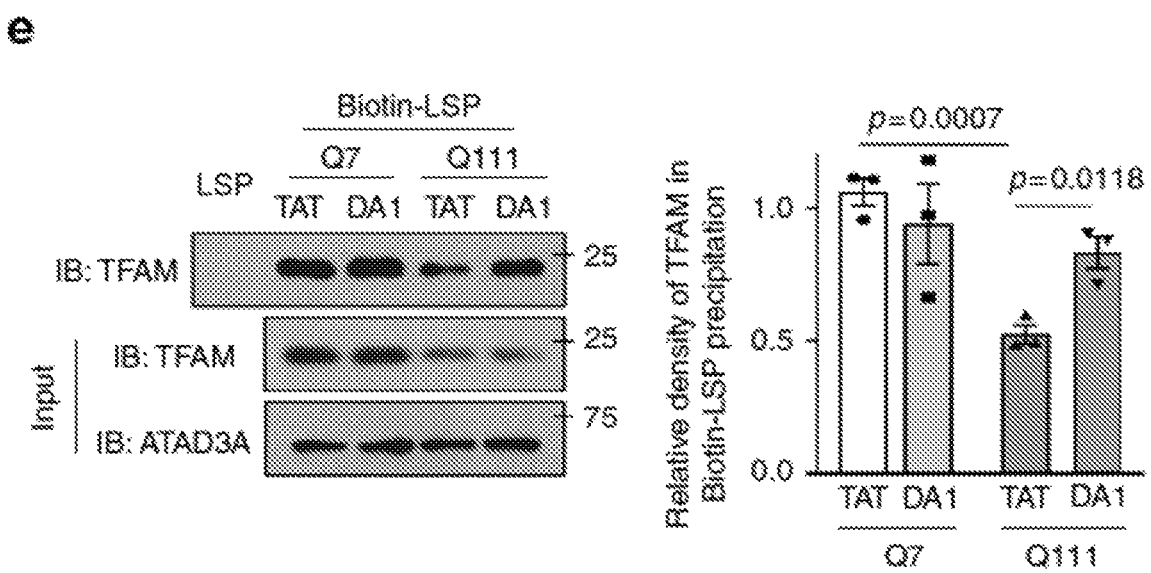
Figure 6F:
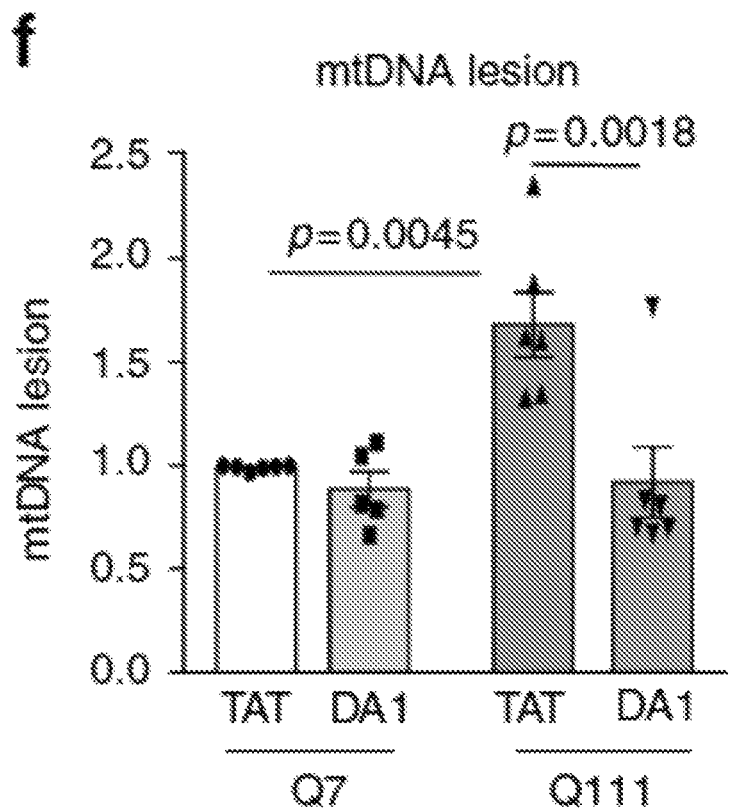
Figure 6G:
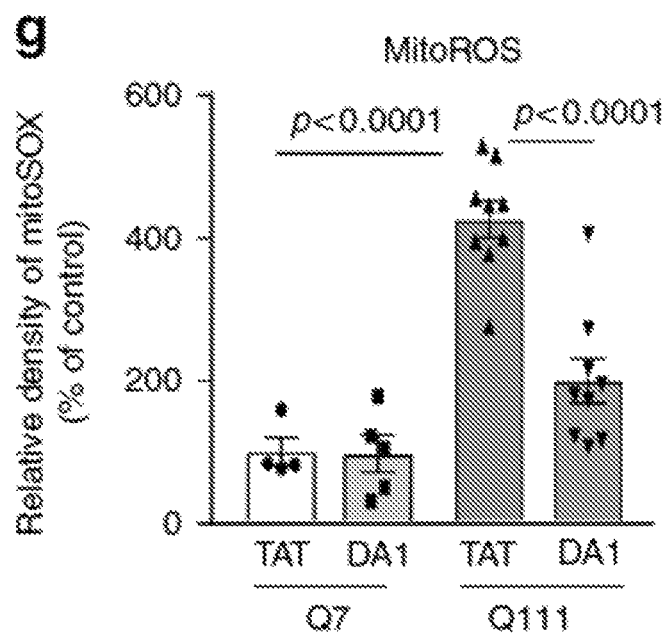
Figure 6H:
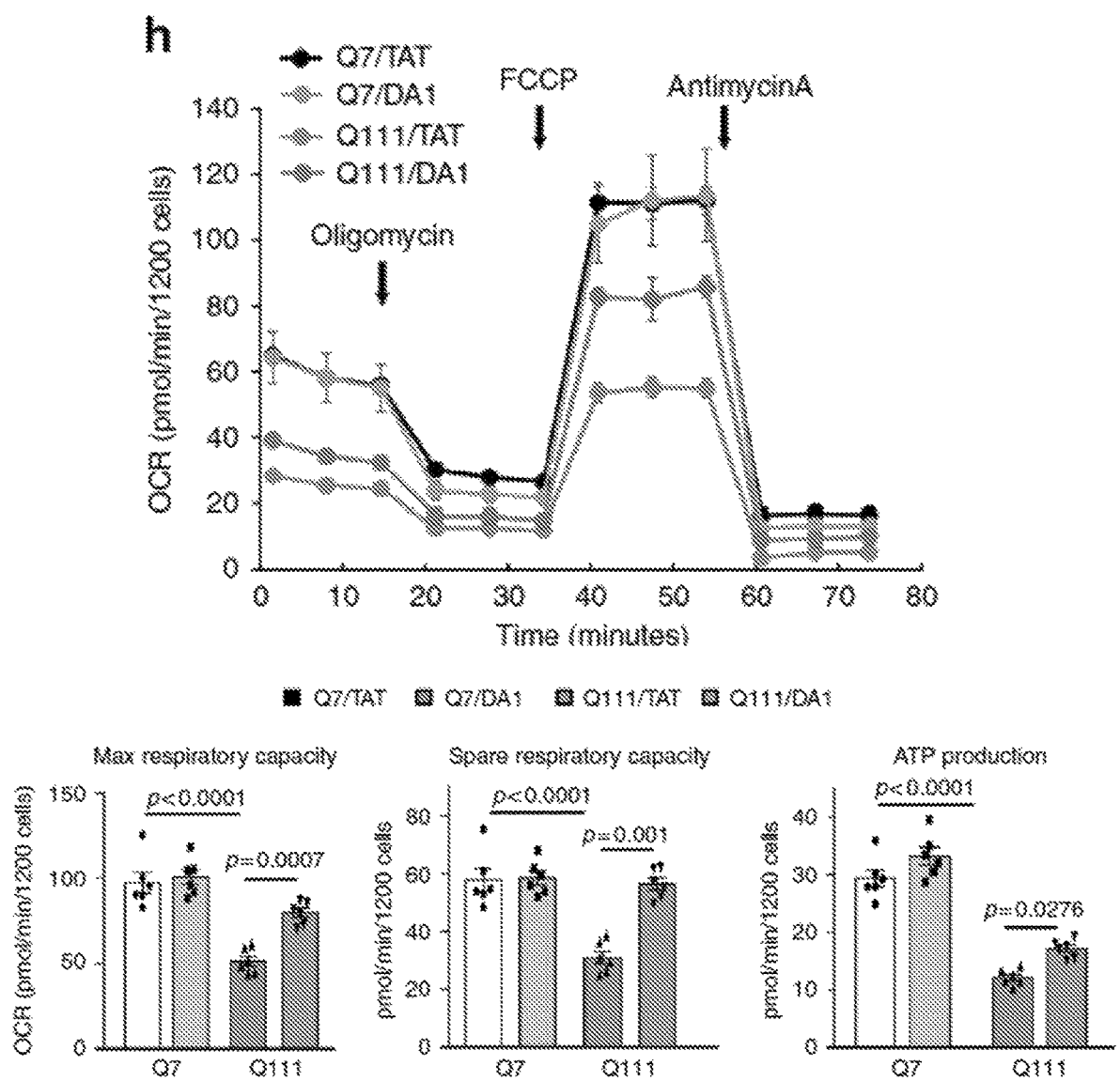
Figure 9J:
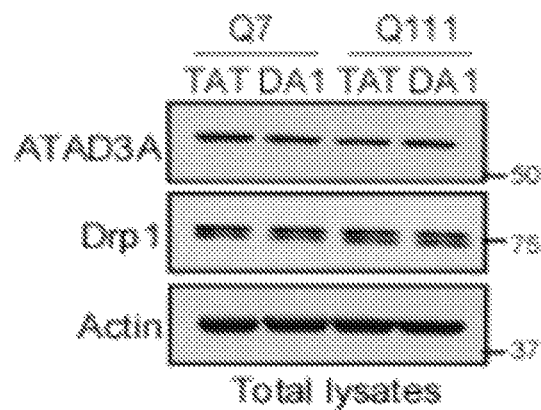
Figure 9J:
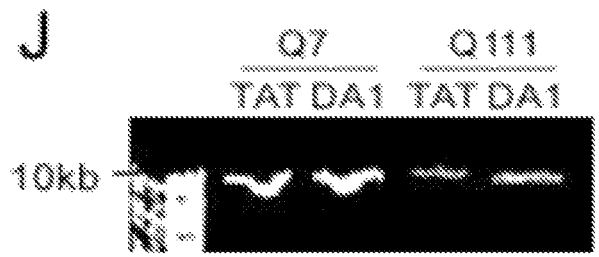

DA1 treatment reduced the number of cells with fragmented mitochondria in HdhQ111 cells relative to the cells treated with control peptide TAT (FIG. 6A). The levels of TFAM and PGC1α, reflecting mitochondrial bioenergetics activity, were decreased in HdhQ111 cells and were restored by DA1 treatment (FIG. 6B). The recovery of DA1 on mitochondrial biogenesis in HD mutant cells requires the presence of ATAD3A, as demonstrated by the finding that ATAD3A knockdown abolished the elevation of TFAM level by DA1 treatment (FIG. 6C). DA1 treatment corrected the decreased mtCO2 protein level in HdhQ111 cells, whereas it had no effect on nuclear-encoded mitochondrial respiratory chain components (FIG. 6D). Notably, treatment with DA1 restored the binding of TFAM and mtDNA (FIG. 6E), increased mtDNA copy number, diminished mtDNA lesion, and suppressed mitochondrial oxidative stress in HdhQ111 cells relative to cells treated with control peptide TAT (FIG. 6F, G and FIG. 9J). Furthermore, DA1 treatment attenuated mitochondrial respiratory defects in HdhQ111 cells; it improved maximal and spare respiratory capacity and ATP production, with minor effects on HdhQ7 cells (FIG. 6H).

Figure 7A:
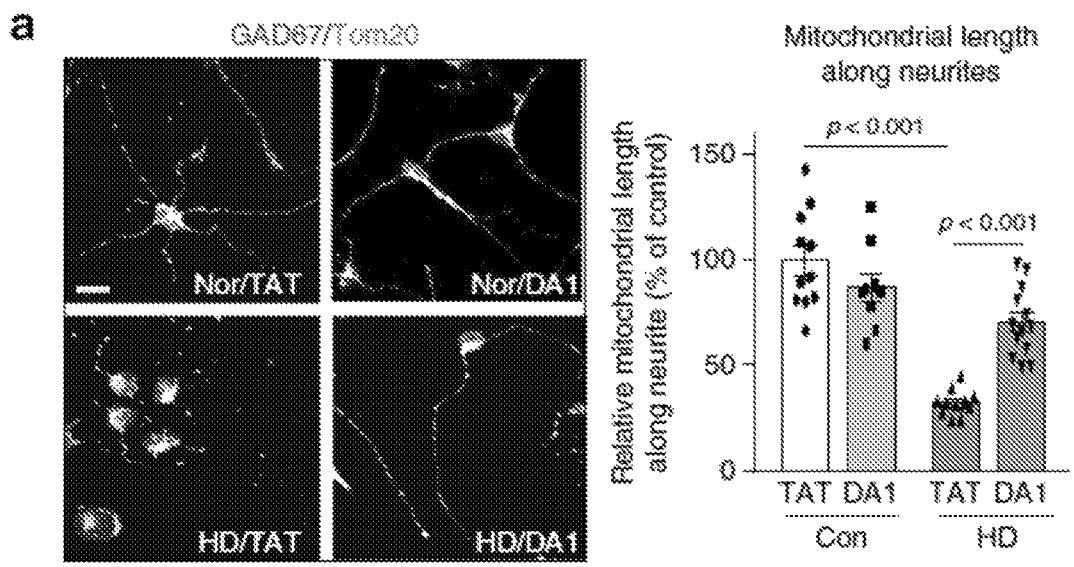
Figure 7C:
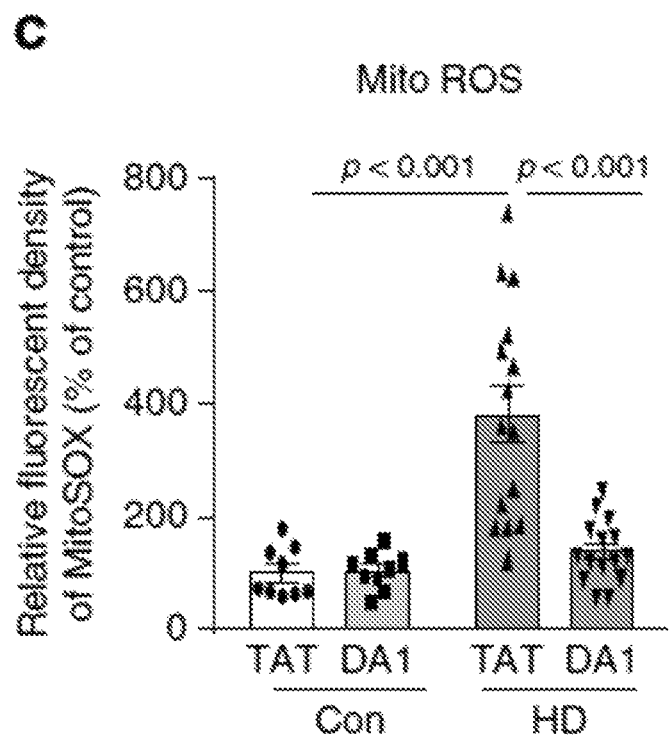
Figure 7B:
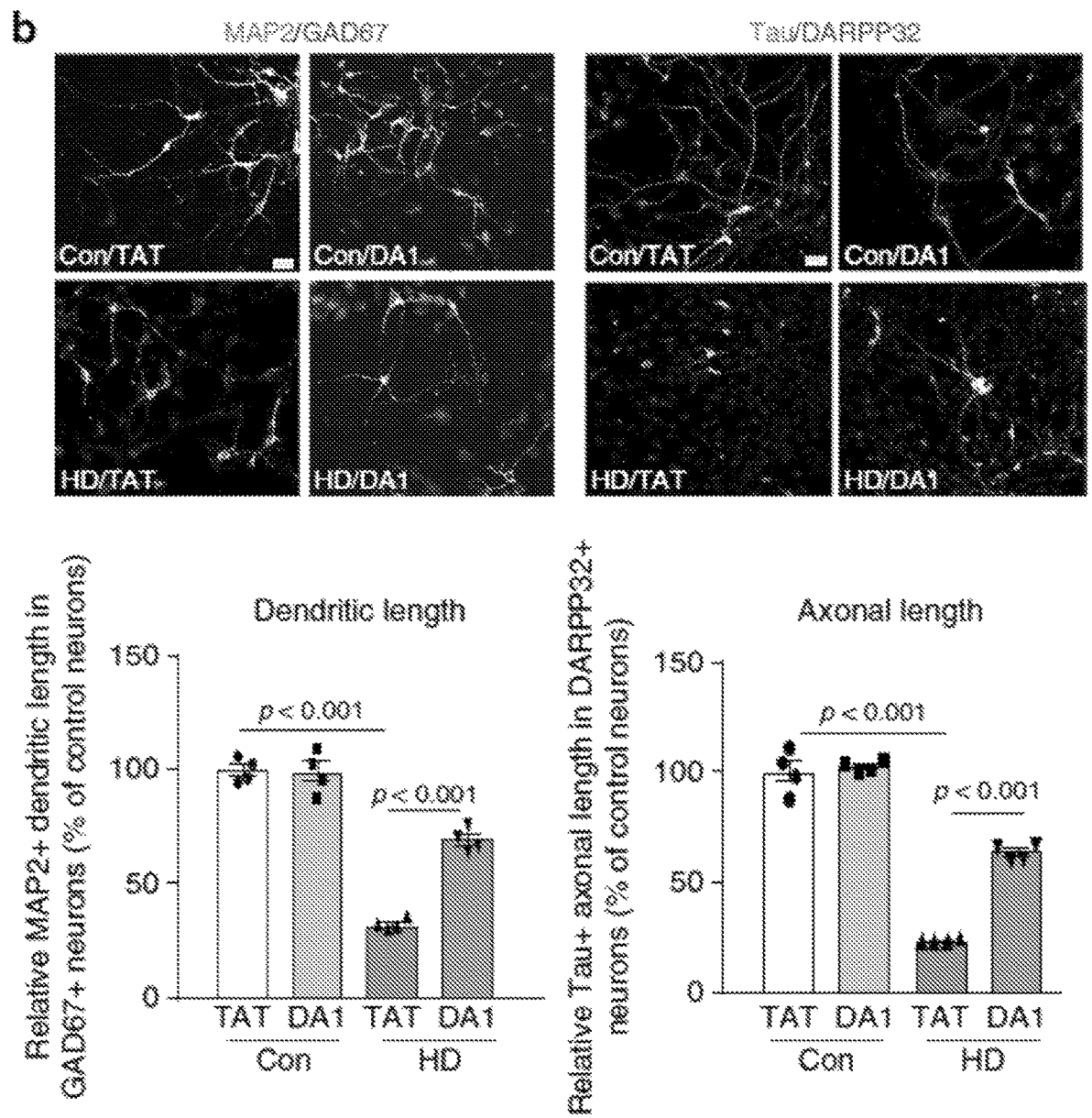
Figure 7D:
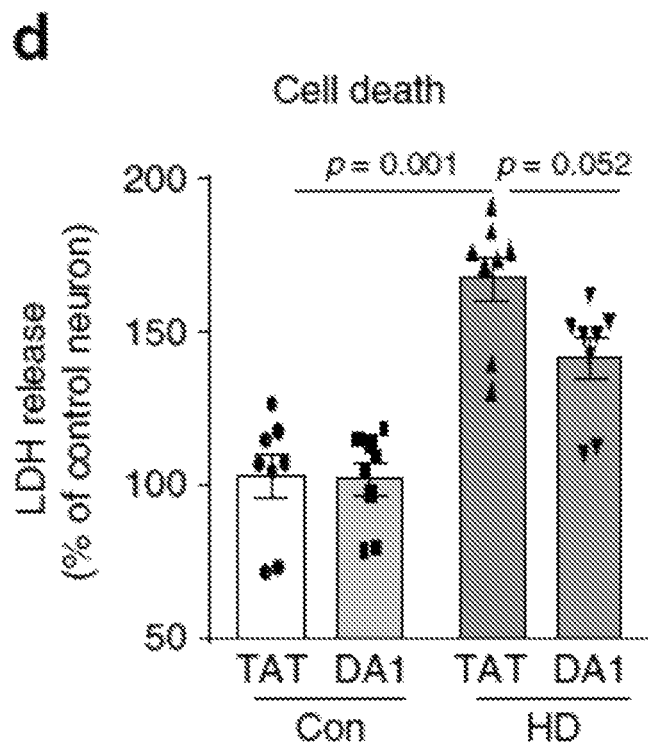
Figure 7E:
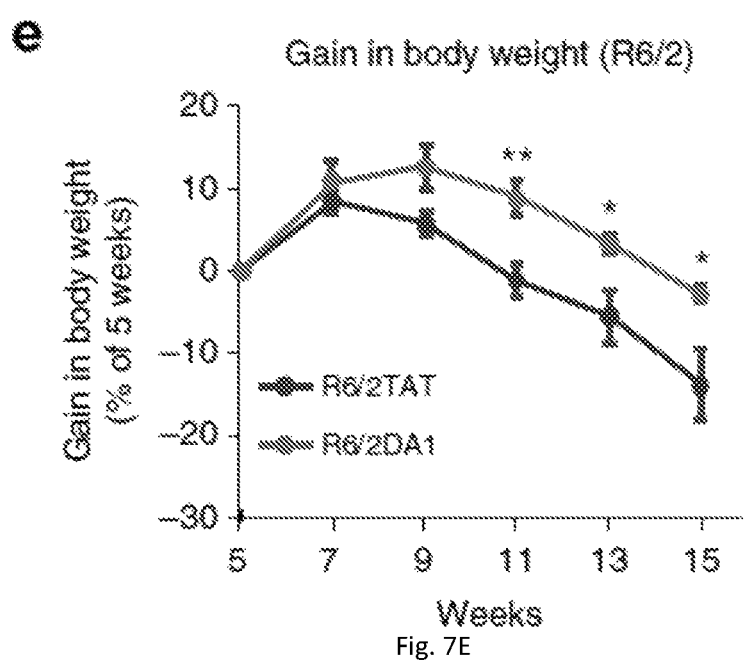
Figure 9K:
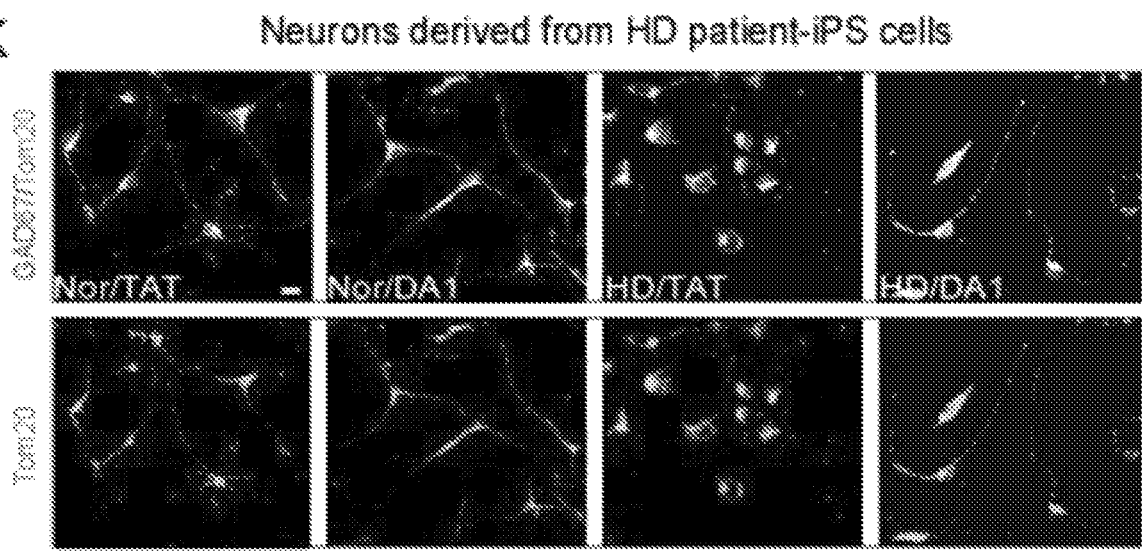

In neurons derived from HD patient-iPS cells, consistent with our previous study, mitochondria were extensively fragmented along the neurites of neurons immune-positive for anti-GAD67 (a marker of GABAergic striatal neurons). In contrast, DA1 treatment increased the length of mitochondria along the neurites of GAD67+-neurons (FIG. 7A and FIG. 9K). Moreover, DA1 treatment improved MAP2+ dendritic and Tau+ axonal outgrowth of striatal neurons derived from HD patient iPS cells (FIG. 7B). The improvement on mitochondrial and neuronal morphology by DA1 treatment was accompanied with decreased mitoROS and cell death in neurons derived from HD patients (FIG. 7C, D). DA1 treatment had no observed effects on mitochondrial morphology and neuronal survival in cells derived from iPS cells of normal subject (FIG. 7A-D). Thus, blocking Drp1/ATAD3A interaction by DA1 peptide inhibitor improves mitochondrial bioenergetics activity and reduces mitochondrial impairment in HD cells.

DA1 Reduces Behavioral Deficits in HD Mice

Figure 7F:
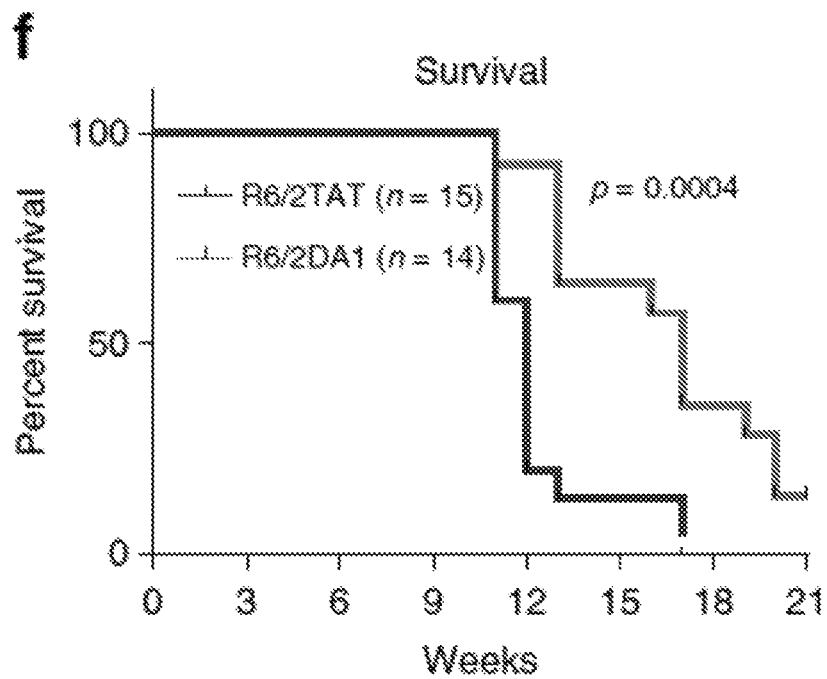
Figure 7G:
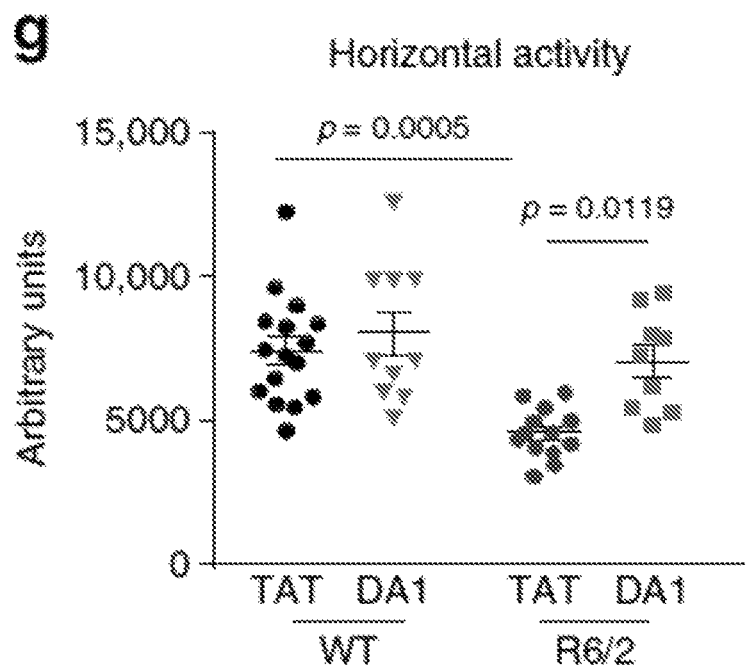
Figure 7H:
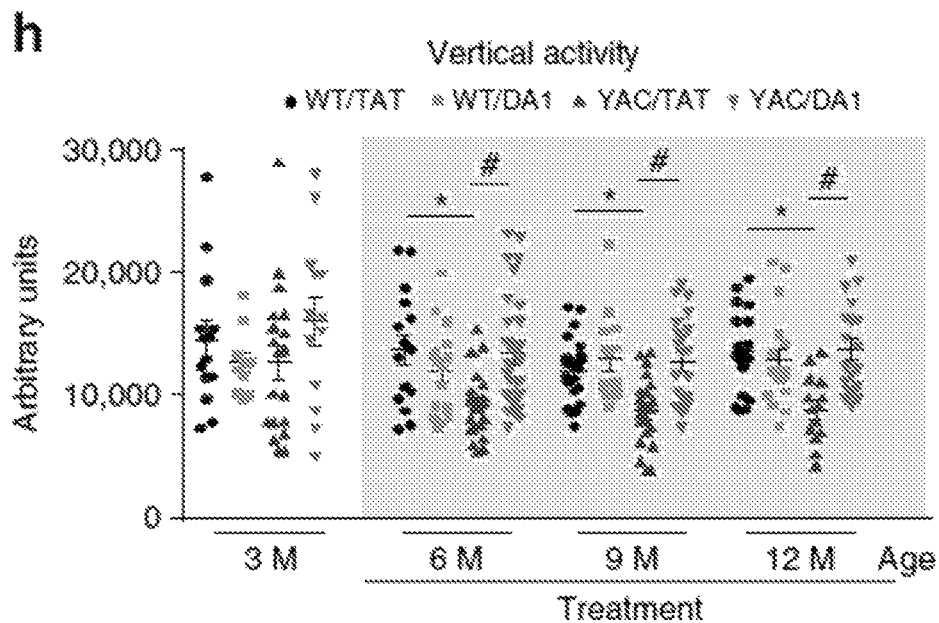
Figure 7J:
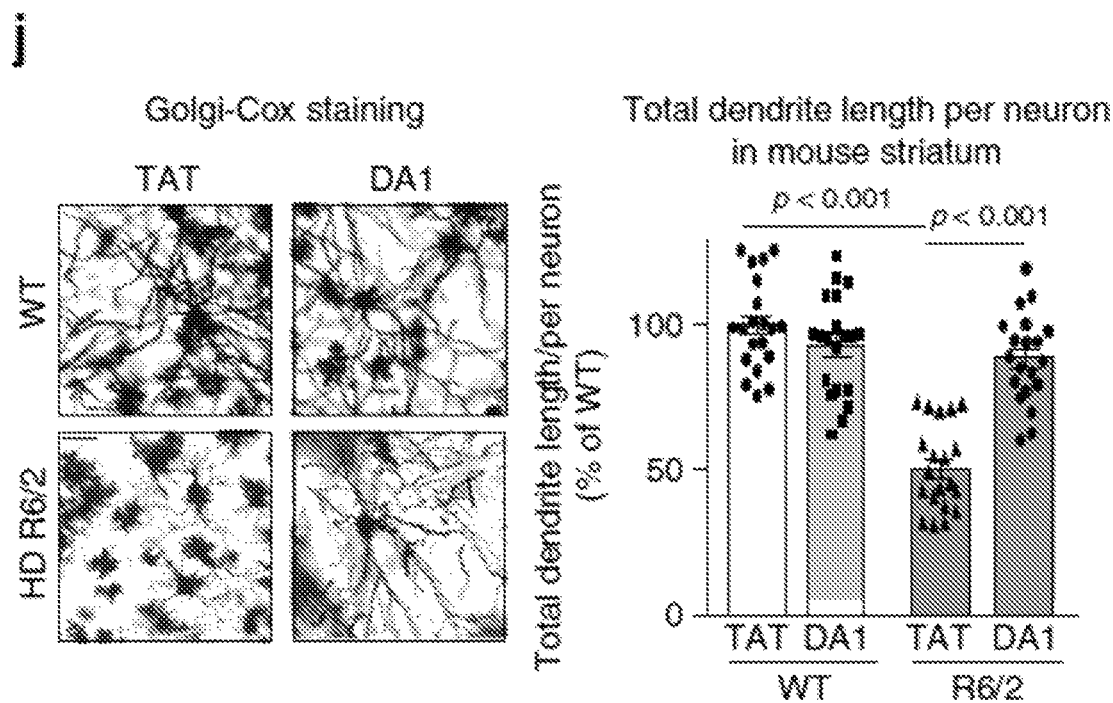
Figure 10A:
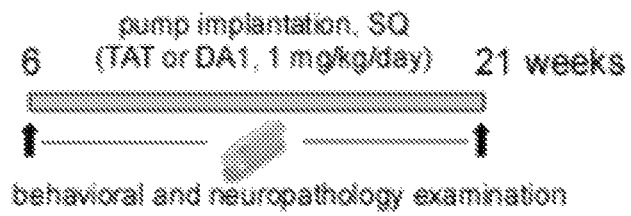
Figure 10A:
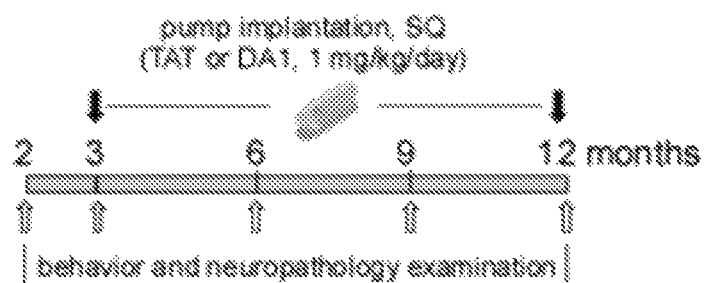
Figure 10B:
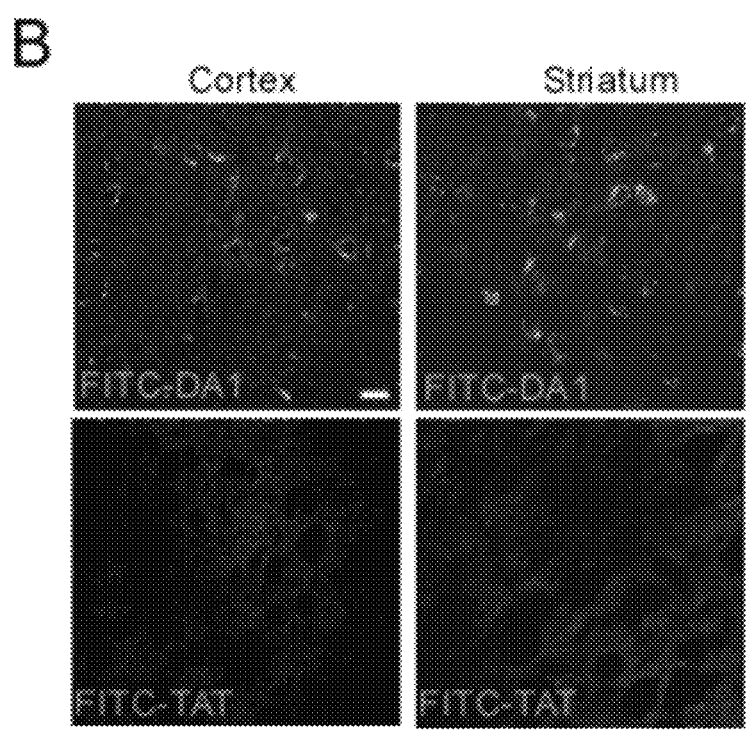
Figure 10C:
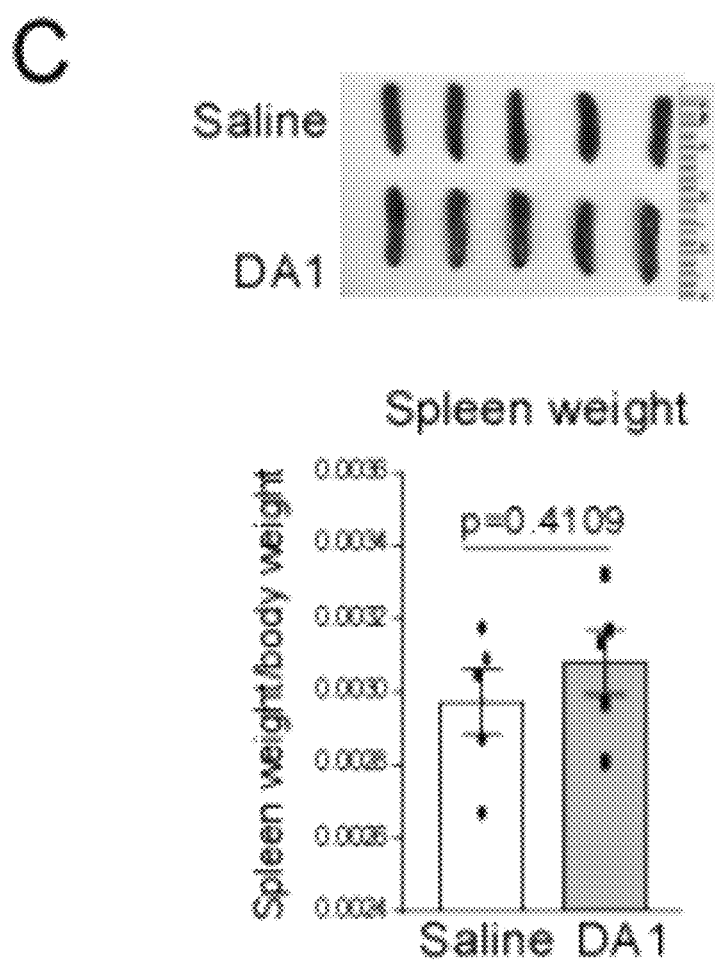
Figure 10D:
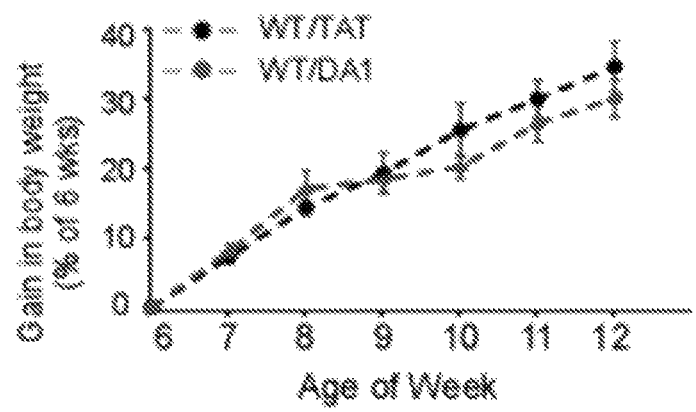
Figure 10E:
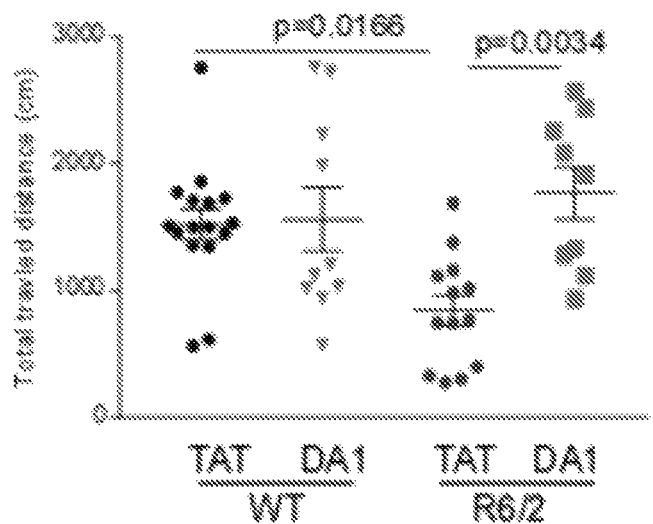
Figure 10F:
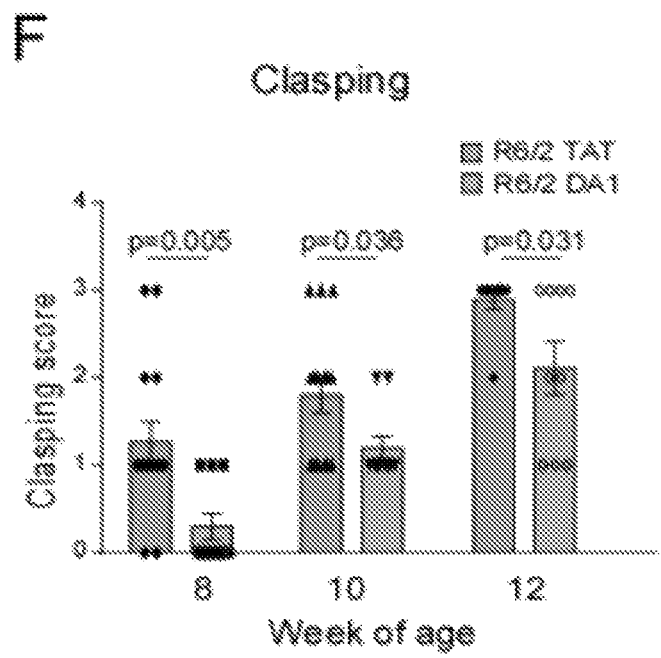
Figure 10H:
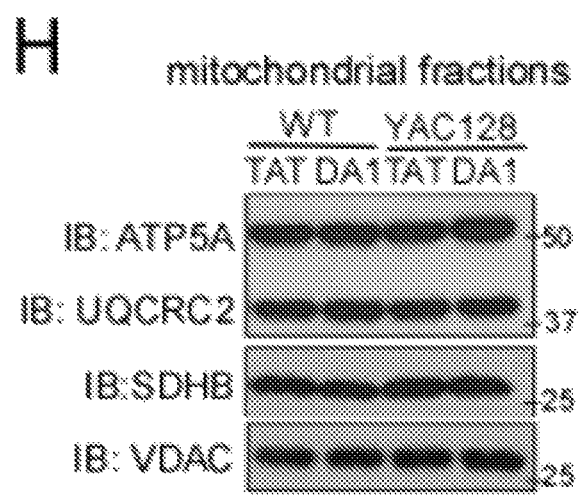
Figure 10G:
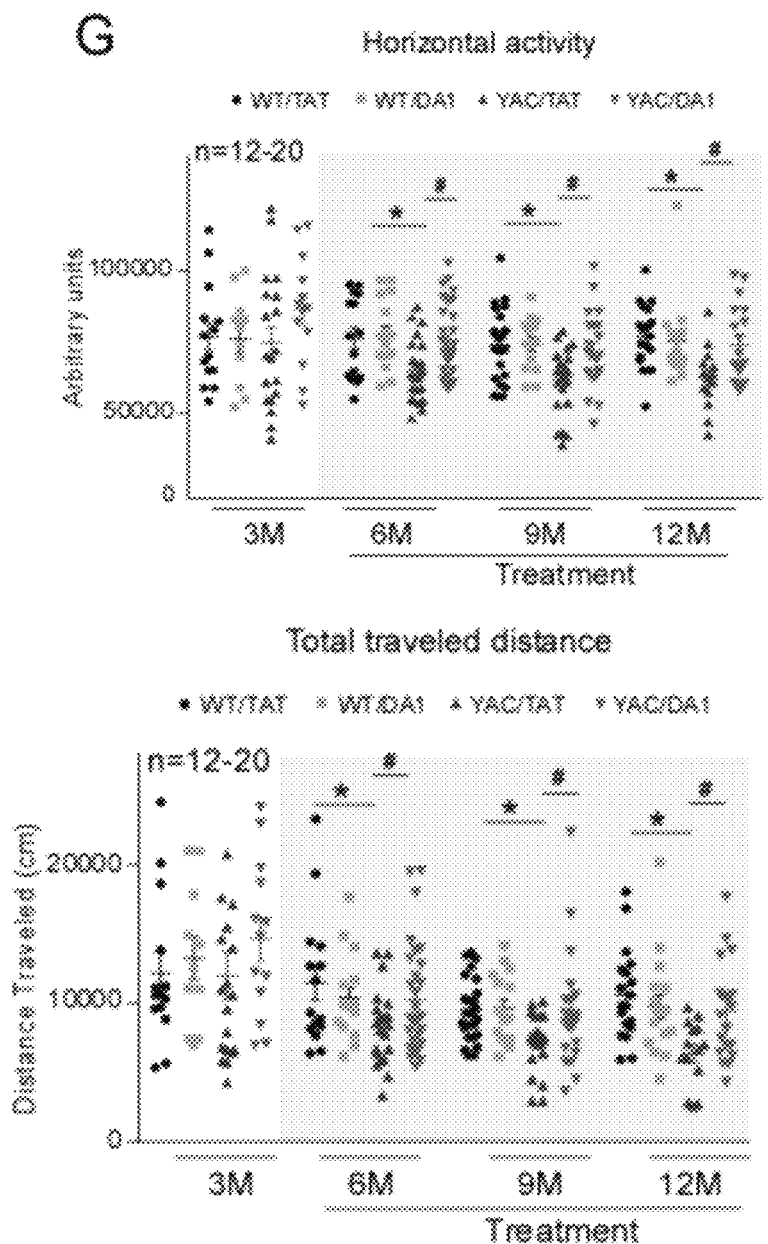
Figure 10G:
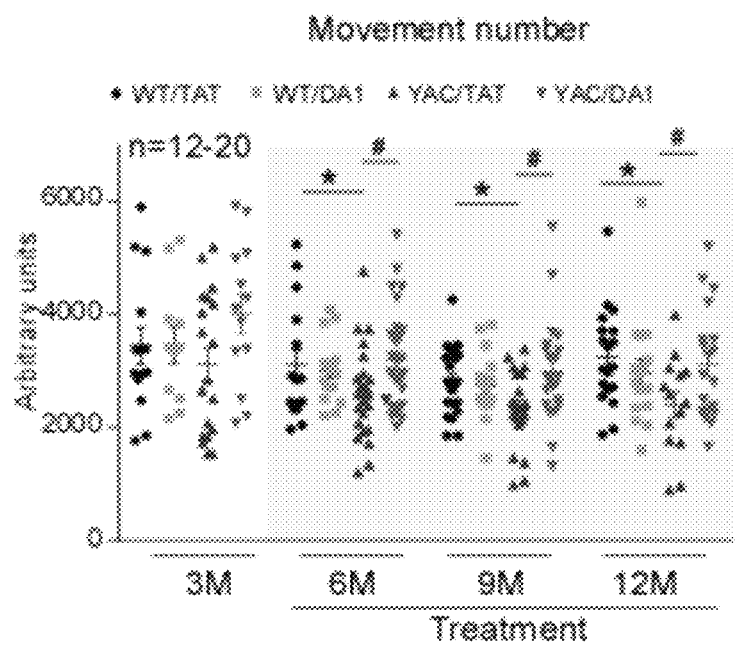

To test whether DA1 treatment improves the disease phenotypes in HD transgenic mice, we subcutaneously treated HD R6/2 from the age of 6 to 21 weeks, and YAC128 mice from the age of 3 to 12 months, with either control peptide TAT or peptide DA1 (1 mg/kg/day) (FIG. 10A). DA1, administered subcutaneously at 1 mg/kg/day, entered the brain (FIG. 10B), and did not cause weight loss or visible side effects in organs (FIG. 10C-D). In HD R6/2 mice, while sustained DA1 treatment moderately suppressed body weight loss (FIG. 7E), the treatment greatly prolonged the survival of mice (FIG. 7F). The treatment had no effect on lifespan of wildtype mice (FIG. 10D). DA1 treatment also increased R6/2 mice horizontal activity and total traveled distance at the age of 12 weeks (FIG. 7g and FIG. 10E), and reduced the severity of clasping behavior over a four-week observation period (FIG. 10F). In YAC128 mice that exhibit progressive deficits in movement activity, sustained treatment with DA1 improved general movement activity starting at the age of 6 months, and the protective effect lasted until the age of 12 months (FIG. 7h and FIG. 10G). In contrast, sustained treatment with DA1 had minor effects on behavioral status of wildtype mice through our studies.

DA1 Reduces HD Neuropathology in Mice

Figure 7I:
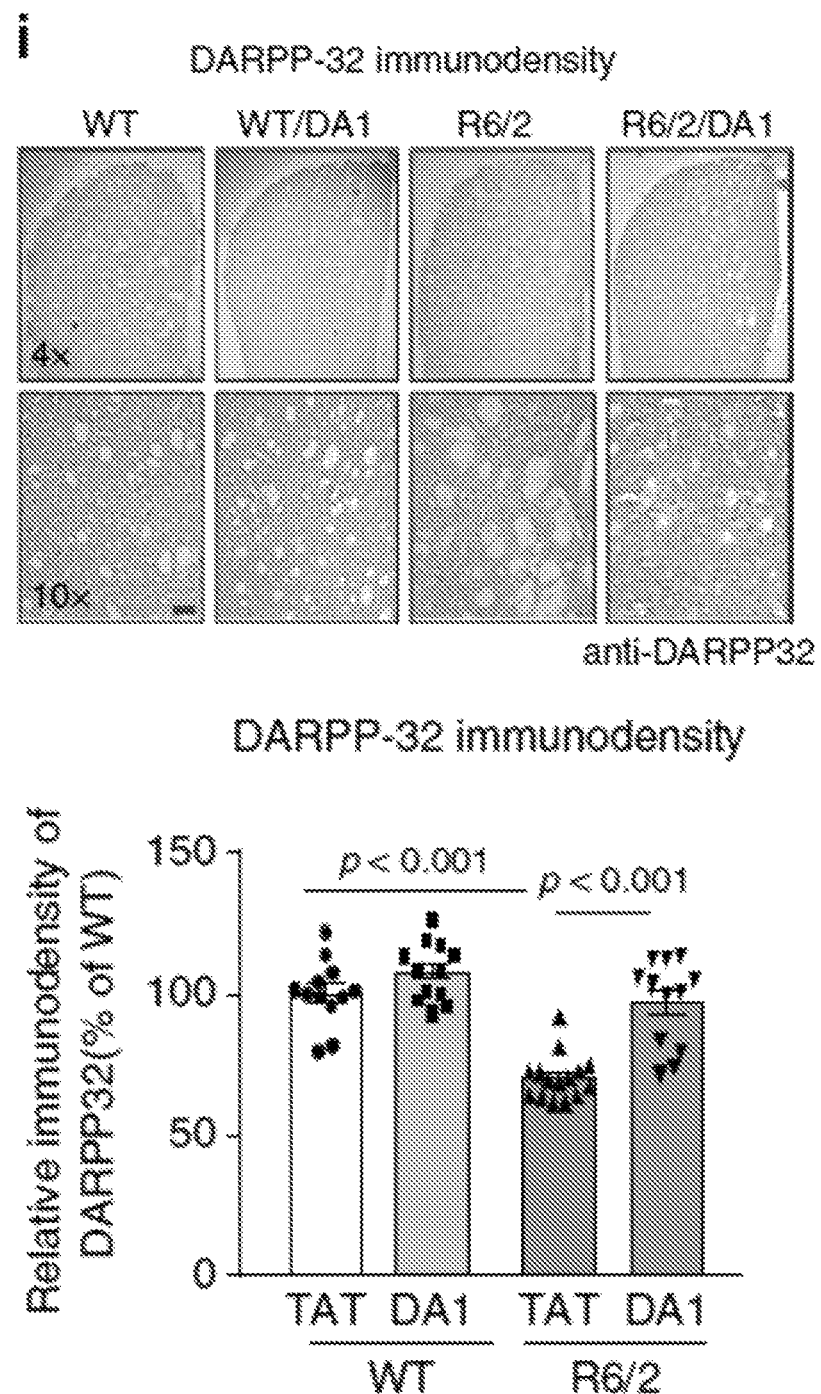
Figure 7K:
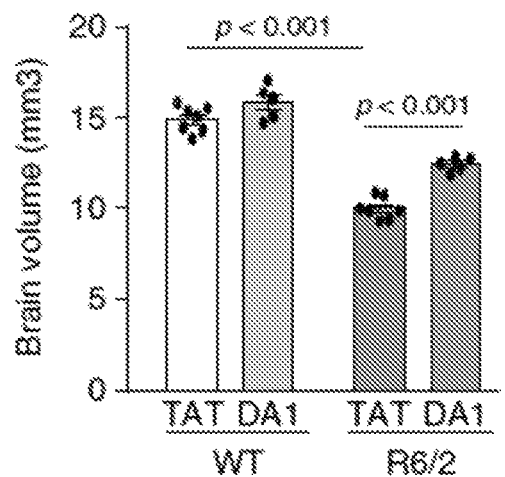
Figure 7L:
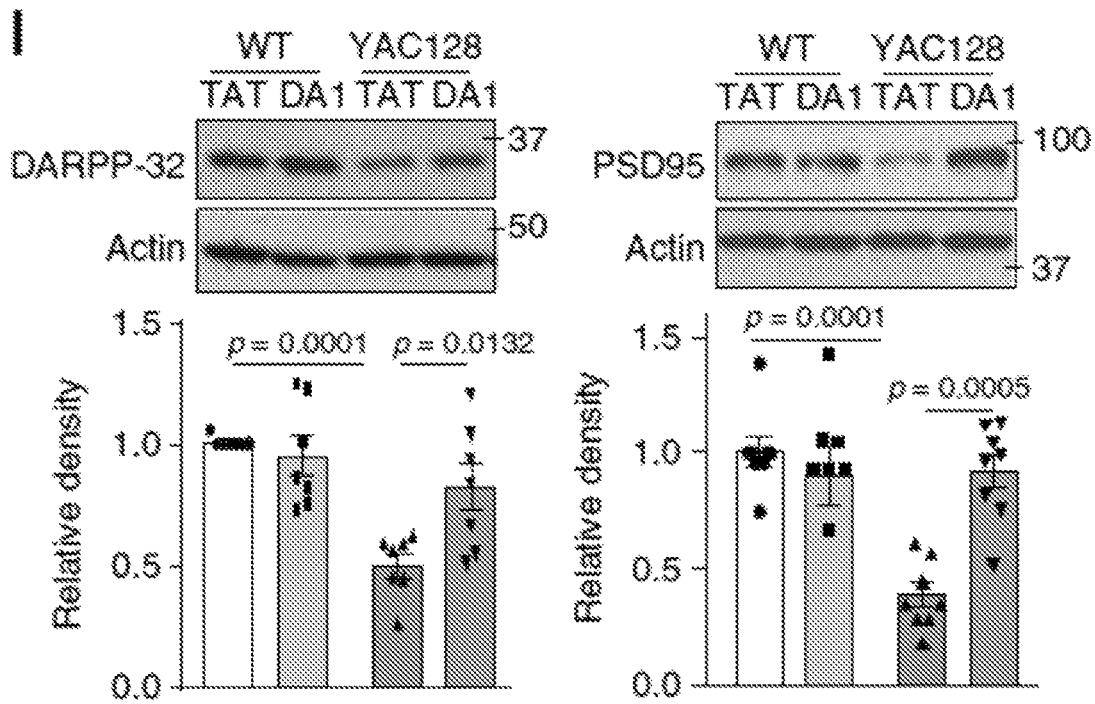

DARPP-32 is a marker of medium spiny neurons (MSN), the decreased level of which is used as a measure of striatal neuronal survival in HD. In R6/2 mice, we observed a decrease in the area occupied by DARPP-32-immunostained cells in the striatum, which was increased by DA1 (FIG. 7I). Treatment with DA1 also improved dendritic morphology of MSN in R6/2 mice, as assessed by Golgi-Cox staining (FIG. 7J), and increased striatum volume of R6/2 mice (FIG. 7K). In YAC128 mice, DA1 treatment increased the protein levels of DARPP-32 and PSD95 (a post-synaptic marker that maintains the postsynaptic density) (FIG. 7L). These results suggest that DA1 treatment improves striatal neuronal survival in vivo.

Figure 8A:
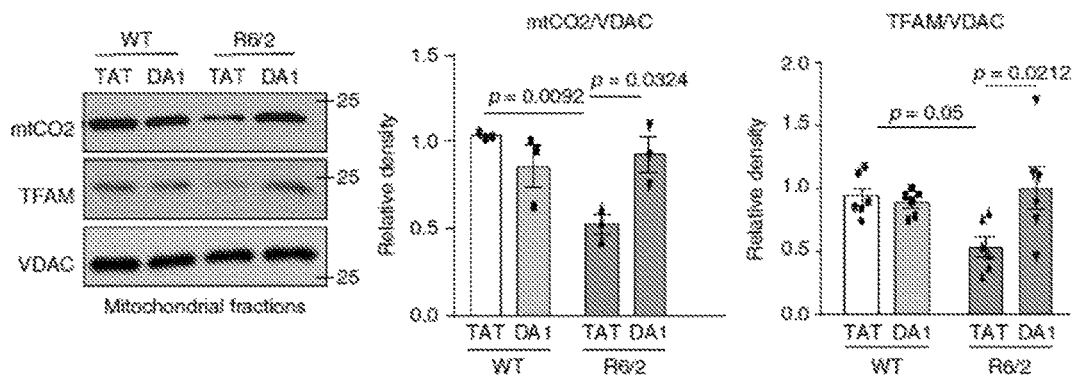
Figure 8B:
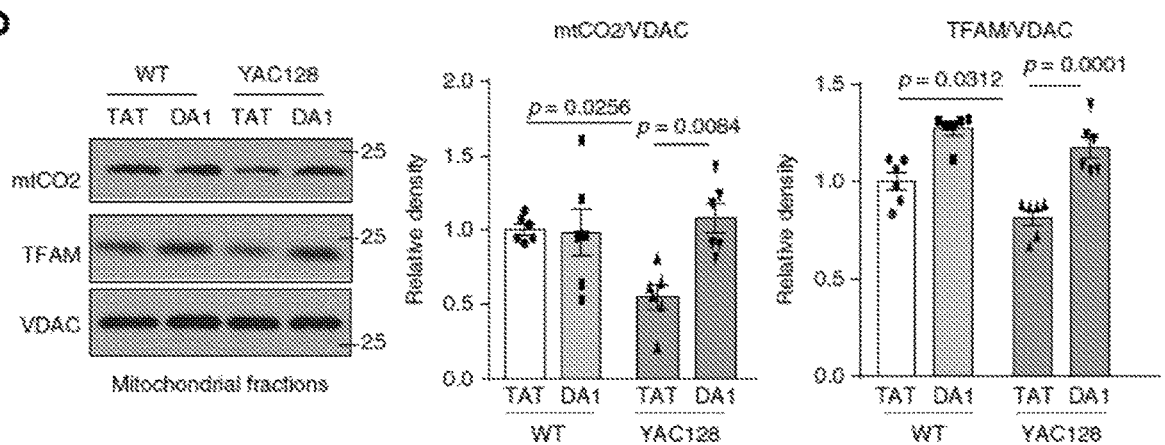
Figure 8C:
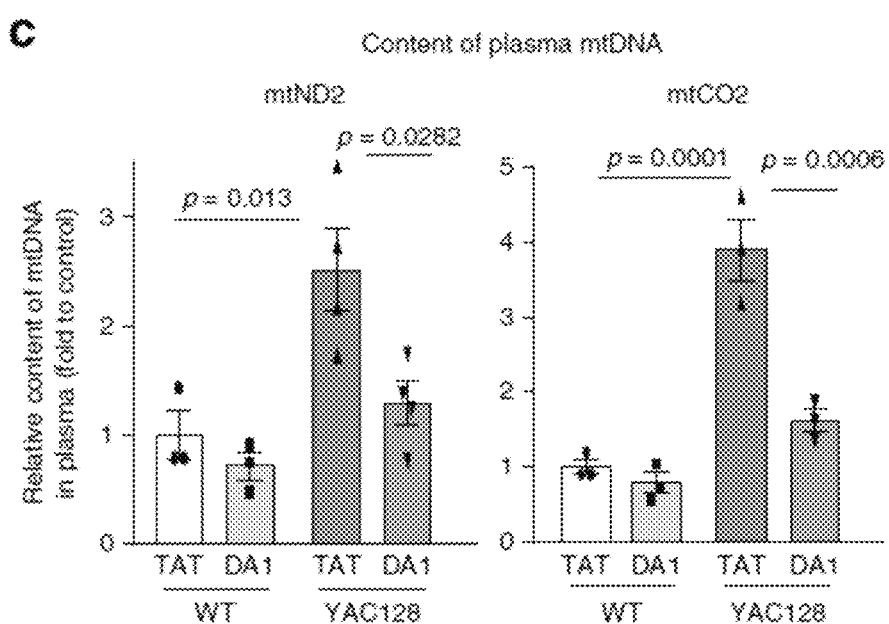
Figure 8D:
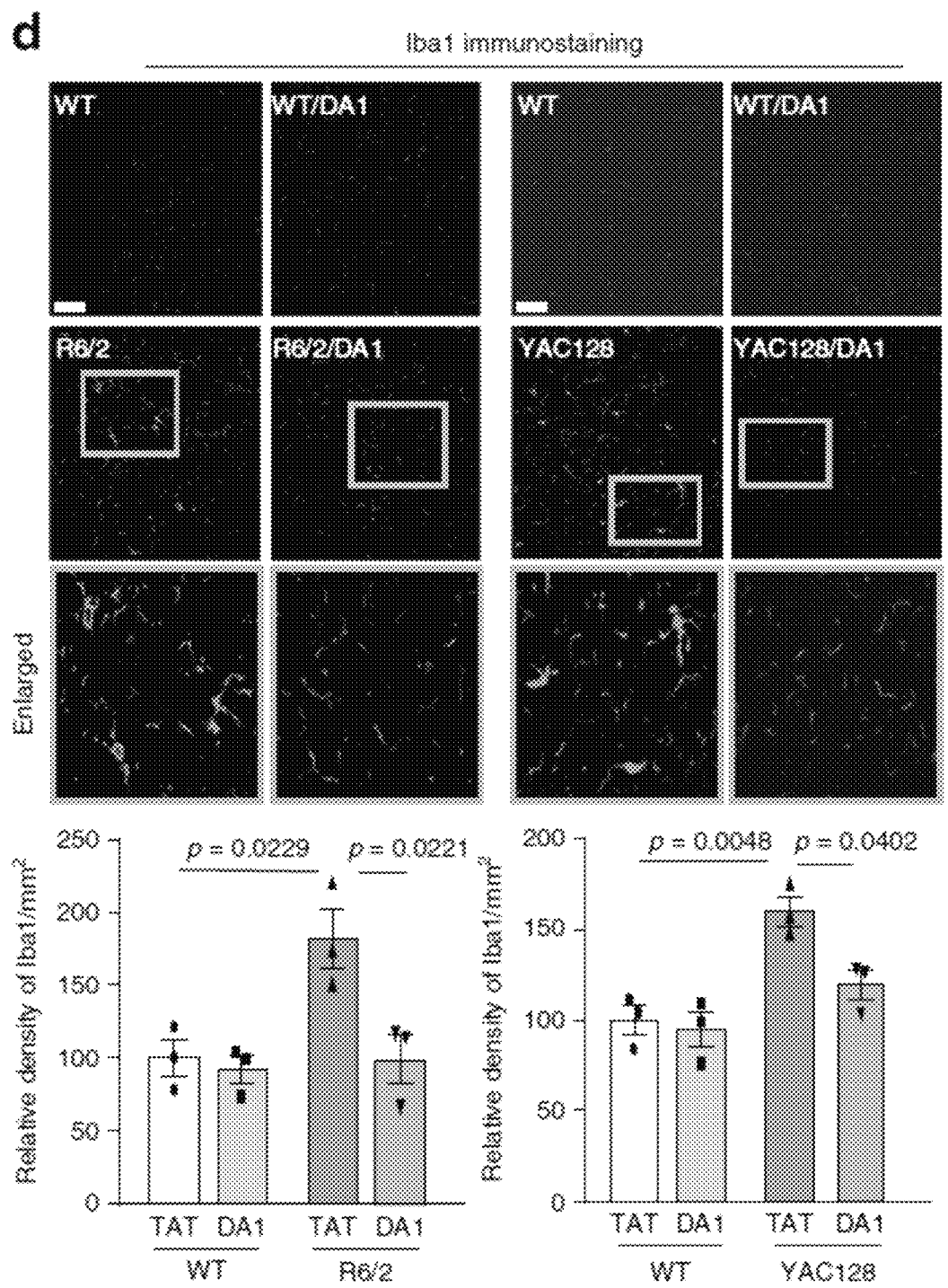
Figure 10I:
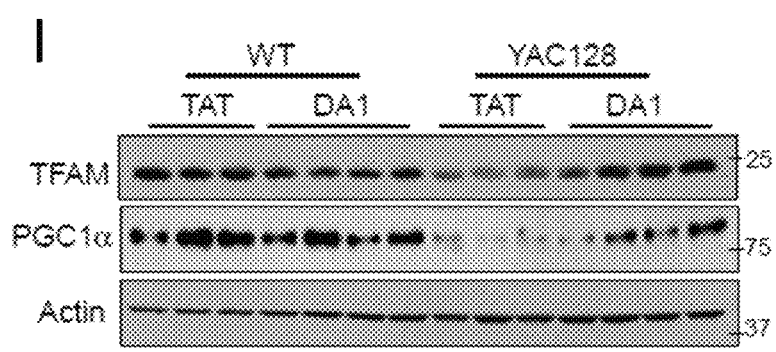
Figure 10I:
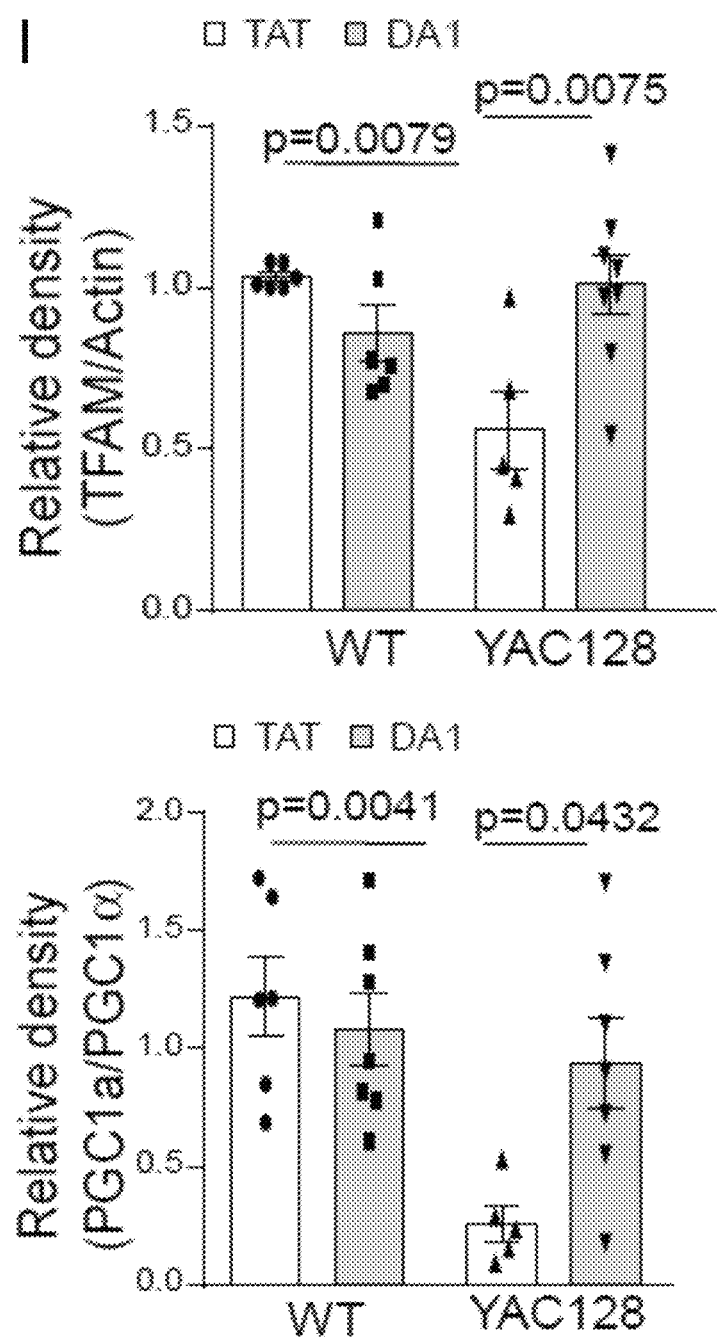

The protein levels of TFAM and mtDNA-coded protein mtCO2 were reduced in both R6/2 and YAC128 mice, which was corrected by DA1 treatment (FIG. 8A, B). Again, DA1 treatment had no observable effects on nuclear-encoded mitochondrial proteins (FIG. 10H). Treatment with DA1 increased PGC1α protein levels in YAC128 mouse striatum until 12 months of age (FIG. 10I). These results are consistent with our findings in culture and suggest that DA1 treatment improves mtDNA maintenance and bioenergetics activity in mouse models of HD. MtDNA detected in the plasma of HD mice and HD patients can serve as a biomarker that correlates with disease progression. In YAC128 mice, which exhibit chronic HD-like neurodegeneration with a year-long disease development, plasma mtDNA content was increased at the age of 6 months (FIG. 8C), an age prior to the onset of neurodegeneration. DA1 treatment abolished this increase (FIG. 8C), further indicating a protective effect on mitochondrial function in HD. Elevated plasma levels of mtDNA can act as cell damage-associated molecular pattern (DAMP), eliciting inflammation. In HD R6/2 and YAC128 mouse striatum, activated microglial cells marked by anti-Iba1 antibody indicated an induction of inflammation. Treatment with DA1 corrected this inflammatory response (FIG. 8D), which is likely the result of suppression of mtDNA lesion.

Figure 8E:
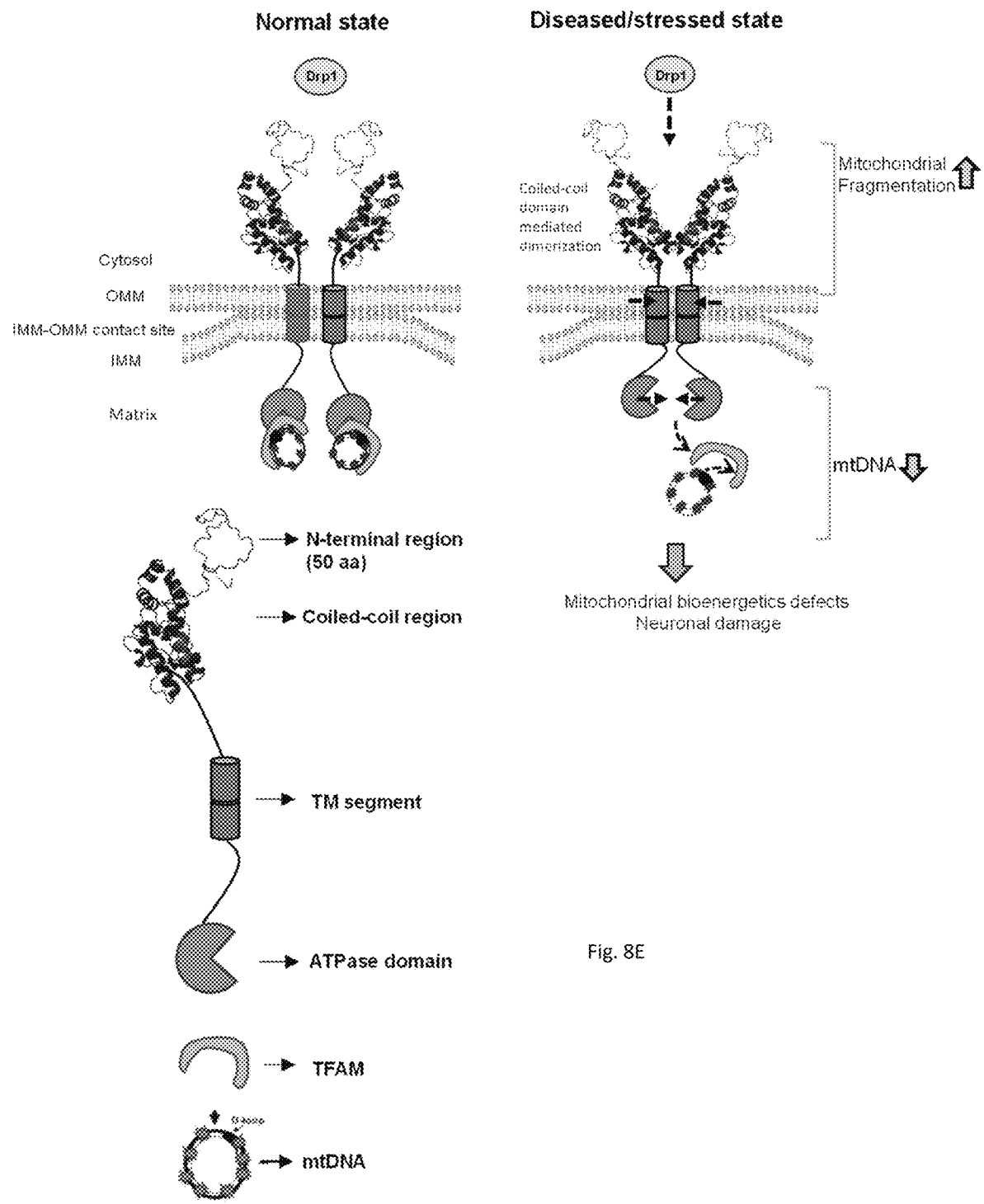

In this example, we found that under stressed conditions, such as in HD, ATAD3A, via pathological oligomerization, exhibits a gain-of-function that causes mitochondrial fragmentation and impairs mitochondrial biogenesis, resulting in neurodegeneration (FIG. 8E). This hypothesis is further supported by our results that the reduction of ATAD3A dimers and subsequent ATAD3A/Drp1 binding by treatment with DA1 suppressed mitochondrial fragmentation and mtDNA damage, and reduced HD neuropathology. Therefore, our findings, by providing evidence for a crucial role of ATAD3A in maintaining mitochondrial integrity and neuronal survival, reveal insights into the pathogenesis of HD, and therefore highlight a promising therapeutic strategy for HD.

ATAD3A has been suggested to locate in the contact sites between the IMM and the OMM, and to be enriched in mitochondria-associated membranes (MAMs). We showed that endogenous ATAD3A was more abundant in the contact sites of mitochondria in HD mutant cells. Thus, ATAD3A interacts with Drp1 on the mitochondrial contact sites of HD cells, where Drp1, upon translocation to the mitochondria, can have a great access to ATAD3A. Mitochondrial fission adaptors Mff, Fis1, and MiD49/51 have been shown to recruit Drp1 to the mitochondria via protein-protein interaction. ATAD3A does not seem to affect Mff, Fis1, and Mid49/51, and vice versa. However, either knockout or overexpression of ATAD3A elicits mitochondrial fragmentation.

AAA family proteins often function as hexameric rings via conserved ATPase domain. We found that the CC domain of ATAD3A is in fact required for ATAD3A oligomerization, as deletion of the CC domain abrogated ATADA3A oligomerization even when the ATPase domain is present. Moreover, ATAD3A oligomerization via the CC domain seems to be a key linking between mitochondrial fission and mtDNA stability. This conclusion is supported by our findings that the prevention of ATAD3A oligomerization by DA1 peptide corrected mitochondrial fragmentation and mtDNA depletion in HD models. Genetically defective ATP-binding in the ATPase domain reduces the ATPase activity of ATAD3A but does not affect ATAD3A steady state or mtDNA content. Though expression of the ATPase deficient mutants is associated with mitochondrial fragmentation, the deletion of the first 50 amino acids in ATAD3A enhances recruitment of Drp1 to the mitochondria. Thus, the CC domain rather than the ATPase enzyme activity of ATAD3A functions as a linker, connecting signals between in and outside mitochondria. The first 50 amino acids are non-structured. Deletion of the 50 amino acids enhanced ATAD3A oligomerization and the binding of ATAD3A to Drp1, and disrupted TFAM/mtDNA complex. Thus, the first 50 amino acids may act as an inhibitory segment to retain the steady state of ATAD3A.

We found that ATAD3A deacetylation at residue K135 is required to its dimerization that is essential for induction of mitochondrial fragmentation and mtDNA lesion. Thus, our findings suggest a model in which in resting cells ATAD3A is acetylated at K135 to maintain its steady state, whereas deacetylation of ATAD3A at this specific site, such as under HD conditions, serves as a switch to promote its oligomerization via the CC domain, which results in a signaling-on conformation of ATAD3A, leading to aberrant activation of the protein.

Manipulation of ATAD3A selectively regulates TFAM, which influences the binding between TFAM and mtDNA. Thus, ATAD3A may act upstream of TFAM. Disturbance of ATAD3A steady state by oligomerization may break the molecular balance between ATAD3A and TFAM/mtDNA, which in turn impairs mtDNA stability and abundance. Interestingly, our proteomic analysis identified TFAM as one of interactors of Drp1 in HD. Similar to ATAD3A, TFAM can be detected on the contact sites of mitochondria. Thus, centered on ATAD3A, Drp1, ATAD3A, and TFAM may form a complex on mitochondria where membrane fission links with nucleoid dynamics Our findings show that ATAD3A is a therapeutic target for combating the mitochondrial damage and neurodegeneration underlying HD and other neurological disorders that feature mitochondrial fragmentation and bioenergetic failure. DA1 biological effects require the presence of ATAD3A, and DA1 influences neither the binding of Drp1 with its mitochondrial adaptors nor the levels of mitochondrial fusion/fission proteins. These characteristics of DA1 make it a unique inhibitor to modulate both mitochondrial fission impairment and bioenergetic defects under pathological conditions. Thus, DA1 peptide is a useful agent to prevent or slow the progression of neurodegeneration.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A method of inhibiting aberrant ATPase family AAA-domain containing protein 3A (ATAD3A) activation and/or oligomerization in mitochondria of a cell, the method comprising:
   administering to the cell a therapeutic peptide linked to a transport moiety, wherein
   the therapeutic peptide consists of about 6 to about 12 amino acids and has at least about 80% sequence identity to about 6 to about 12 consecutive amino acids of an interaction site of dynamin-related protein 1 (Drp1) with a first coiled-coil domain of ATAD3A, and inhibits binding or complexing of ATAD3A with Drp-1 in the mitochondria of the cell; and
   wherein the transport moiety facilitates uptake of the therapeutic peptide by a nerve cell.

2. The method of claim 1, wherein the cell is a nerve cell of a subject with a neurodegenerative disorder.

3. The method of claim 1, wherein the therapeutic peptide has an amino acid sequence that is at least about 80% identical to at least 6 consecutive amino acids of SEQ ID NO: 1.

4. The method of claim 3, wherein the therapeutic peptide has an amino acid sequence at least 80% identical to SEQ ID NO: 2.

5. The method of claim 1, wherein the transport moiety is an HIV Tat transport moiety.

6. The method of claim 1, wherein the cell is a nerve cell in a subject with neurodegenerative disorder and the therapeutic peptide is administered systemically to the subject.

7. The method of claim 1, wherein the therapeutic peptide has the amino acid sequence of SEQ ID NO: 2 and is linked to a HIV Tat transport moiety.

8. A method of treating a disorder associated with aberrant ATAD3A activation in mitochondria of nerves cells in a subject in need thereof, the method comprising:
   administering to the subject
   a therapeutic peptide linked to a transport moiety, wherein
      the therapeutic peptide consists of about 6 to about 12 amino acids and has at least about 80% sequence identity to about 6 to about 12 consecutive amino acids of an interaction site of Drp1 with a first coiled-coil domain of ATAD3A, and inhibits binding of ATAD3A with Drp1 in the mitochondria of the nerve cells, and
   wherein the transport moiety facilitates uptake of the therapeutic peptide by the nerve cell.

9. The method of claim 8, wherein the disorder is a neurodegenerative disorder.

10. The method of claim 8, wherein the disorder is Huntington's disease.

11. The method of claim 8, wherein the therapeutic peptide has an amino acid sequence that is at least about 80% identical to at least 6 consecutive amino acids of SEQ ID NO: 1.

12. The method of claim 11, wherein the therapeutic peptide has an amino acid sequence at least 80% identical to SEQ ID NO: 2.

13. The method of claim 8, wherein the transport moiety is an HIV Tat transport moiety.

14. The method of claim 8, wherein the therapeutic peptide is administered systemically to the subject.

15. The method of claim 8, wherein the therapeutic peptide has the amino acid sequence of SEQ ID NO: 2 and is linked to a HIV Tat transport moiety.

16. The method of claim 8, wherein the therapeutic peptide and the transport moiety together have the amino acid sequence of SEQ ID NO: 16.

\* \* \* \* \*